United States Patent
Panitch et al.

(10) Patent No.: US 10,772,931 B2
(45) Date of Patent: Sep. 15, 2020

(54) COLLAGEN BINDING SYNTHETIC PEPTIDOGLYCANS FOR TREATMENT OF ENDOTHELIAL DYSFUNCTION

(71) Applicant: Purdue Research Foundation, West Lafayette, IN (US)

(72) Inventors: Alyssa Panitch, Davis, CA (US); Rebecca Scott, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/306,656

(22) PCT Filed: Apr. 24, 2015

(86) PCT No.: PCT/US2015/027643
§ 371 (c)(1),
(2) Date: Oct. 25, 2016

(87) PCT Pub. No.: WO2015/164822
PCT Pub. Date: Oct. 29, 2015

(65) Prior Publication Data
US 2017/0043023 A1 Feb. 16, 2017

Related U.S. Application Data

(60) Provisional application No. 61/984,452, filed on Apr. 25, 2014.

(51) Int. Cl.
| A61K 38/16 | (2006.01) |
| A61K 45/06 | (2006.01) |
| A61K 38/17 | (2006.01) |
| A61K 38/14 | (2006.01) |
| A61K 47/61 | (2017.01) |
| A61K 9/00  | (2006.01) |

(52) U.S. Cl.
CPC .............. *A61K 38/16* (2013.01); *A61K 38/14* (2013.01); *A61K 38/1709* (2013.01); *A61K 45/06* (2013.01); *A61K 47/61* (2017.08); *A61K 9/0019* (2013.01)

(58) Field of Classification Search
CPC .................................................. A61K 38/16
See application file for complete search history.

(56) References Cited

U.S. PATENT DOCUMENTS

| 4,683,298 A | 7/1987 | Yalpani |
| 5,271,929 A | 12/1993 | Hashiguchi et al. |
| 5,342,830 A | 8/1994 | Scarborough |
| 5,547,936 A | 8/1996 | Ruoslahti et al. |
| 5,693,625 A | 12/1997 | Barritault et al. |
| 5,852,004 A | 12/1998 | Barritault et al. |
| 5,955,578 A | 9/1999 | Pierschbacher et al. |
| 5,997,895 A | 12/1999 | Narotam et al. |
| 6,703,491 B1 | 3/2004 | Homburger et al. |
| 6,822,071 B1 | 11/2004 | Stephens et al. |
| 6,864,235 B1 | 3/2005 | Turley et al. |
| 6,932,973 B2 | 8/2005 | Barritault et al. |
| 7,098,194 B2 | 8/2006 | Chenite et al. |
| 7,534,436 B2 | 5/2009 | Courty et al. |
| 7,592,009 B2 | 9/2009 | Hubbell et al. |
| 7,597,889 B1 | 10/2009 | Armour et al. |
| 7,671,018 B2 | 3/2010 | Carson et al. |
| 7,709,439 B2 | 5/2010 | Helmus et al. |
| 7,732,427 B2 | 6/2010 | Kiick et al. |
| 7,737,131 B2 | 6/2010 | Kiick et al. |
| 7,803,905 B2 | 9/2010 | Farach-Carson et al. |
| 7,842,667 B2 | 11/2010 | Seliktar et al. |
| 7,851,445 B2 | 12/2010 | Stupp et al. |
| 7,855,187 B1 | 12/2010 | Prestwich et al. |
| 7,862,831 B2 | 1/2011 | Wang et al. |
| 7,897,165 B2 | 3/2011 | Elisseeff et al. |
| 7,919,111 B2 | 4/2011 | Chudzik et al. |
| 8,007,774 B2 | 8/2011 | Seliktar et al. |
| 8,114,834 B2 | 2/2012 | Hsu et al. |
| 8,188,220 B2 | 5/2012 | Ruoslahti et al. |
| 8,268,950 B2 | 9/2012 | Elisseeff |
| 8,283,414 B2 | 10/2012 | Yu et al. |
| 8,304,388 B2 | 11/2012 | Chettibi et al. |
| 8,314,195 B2 | 11/2012 | Elisseeff |
| 8,329,673 B2 | 12/2012 | Prestwich et al. |
| 8,338,390 B2 | 12/2012 | Kiick et al. |
| 8,343,764 B2 | 1/2013 | Abad et al. |

(Continued)

FOREIGN PATENT DOCUMENTS

| CA | 2299687 A1 | 2/1999 |
| EP | 0462194 A1 | 12/1991 |

(Continued)

OTHER PUBLICATIONS

Sharrock, Damage control—trauma care in the first hour and beyond: a clinical review of relevant developments in the field of trauma care, Ann R Coll Surg Engl 2013; 95: 177-183.* van Hinsbergh, Endothelium—role in regulation of coagulation and inflammation, Semin Immunopathol 2012, 34:93-106, epublished Aug. 4, 2011 (Year: 2012).*

Lievens, Platelets in atherosclerosis, Thromb Haemost 2011; 106: 827-838 (Year: 2011).*

Kolářová, Modulation of Endothelial Glycocalyx Structure under Inflammatory Conditions, Mediators of Inflammation 2014 (Year: 2014).*

(Continued)

*Primary Examiner* — Marcela M Cordero Garcia

(74) *Attorney, Agent, or Firm* — Sheppard Mullin Richter & Hampton LLP

(57) ABSTRACT

Compositions and methods are provided for treating a patient suffering from a disease associated with endothelial dysfunction by administering to the patient a pharmaceutical composition containing an effective amount of a synthetic collagen binding peptidoglycan.

7 Claims, 6 Drawing Sheets

Specification includes a Sequence Listing.

(56) References Cited

U.S. PATENT DOCUMENTS

| | | |
|---|---|---|
| 8,343,942 B2 | 1/2013 | Oottamasathien et al. |
| 8,367,639 B2 | 2/2013 | Kilck et al. |
| 8,389,467 B2 | 3/2013 | Chaput et al. |
| 8,415,325 B2 | 4/2013 | Kiick et al. |
| 8,431,146 B2 | 4/2013 | Harley et al. |
| 8,431,226 B2 | 4/2013 | Huerta et al. |
| 8,450,271 B2 | 5/2013 | Shah et al. |
| 8,470,780 B2 | 6/2013 | Ruoslahti et al. |
| 8,476,220 B2 | 7/2013 | Barritault et al. |
| 8,557,774 B2 | 10/2013 | Vandroux et al. |
| 8,673,333 B2 | 3/2014 | Elisseeff et al. |
| 8,703,740 B2 | 4/2014 | Cho et al. |
| 8,790,631 B2 | 7/2014 | Barritault et al. |
| 8,846,003 B2 | 9/2014 | Panitch et al. |
| 8,883,182 B2 | 11/2014 | Ratcliffe et al. |
| 8,883,964 B2 | 11/2014 | Yu et al. |
| 9,173,919 B2 | 11/2015 | Paderi et al. |
| 9,200,039 B2 | 12/2015 | Panitch et al. |
| 9,217,016 B2 | 12/2015 | Panitch et al. |
| 9,474,782 B2 | 10/2016 | Kichler et al. |
| 9,512,192 B2 | 12/2016 | Panitch et al. |
| 2002/0098153 A1 | 7/2002 | Allen et al. |
| 2002/0183282 A1 | 12/2002 | Dahricorreia et al. |
| 2003/0087255 A1 | 5/2003 | Barritault et al. |
| 2003/0124705 A1 | 7/2003 | Berry et al. |
| 2003/0149173 A1 | 8/2003 | Rhee et al. |
| 2003/0199615 A1 | 10/2003 | Chaput et al. |
| 2004/0091540 A1 | 5/2004 | Desrosiers et al. |
| 2004/0127416 A1 | 7/2004 | Massia et al. |
| 2004/0214272 A1 | 10/2004 | La Rosa et al. |
| 2004/0236092 A1 | 11/2004 | Dziarski et al. |
| 2005/0043221 A1 | 2/2005 | Fallon et al. |
| 2005/0069572 A1 | 3/2005 | Williams et al. |
| 2005/0108791 A1 | 5/2005 | Edgerton |
| 2005/0113297 A1 | 5/2005 | Francois et al. |
| 2005/0147679 A1 | 7/2005 | Petito et al. |
| 2005/0187146 A1 | 8/2005 | Helmus et al. |
| 2005/0196377 A1 | 9/2005 | Ratcliffe et al. |
| 2005/0208114 A1 | 9/2005 | Petito et al. |
| 2006/0024696 A1 | 2/2006 | Kapur et al. |
| 2006/0075522 A1 | 4/2006 | Cleveland et al. |
| 2006/0123505 A1 | 6/2006 | Kikuchi et al. |
| 2006/0241022 A1 | 10/2006 | Bowen et al. |
| 2006/0252692 A1 | 11/2006 | Lasser et al. |
| 2007/0071676 A1 | 3/2007 | Gonzales et al. |
| 2007/0098675 A1 | 5/2007 | Elisseeff et al. |
| 2007/0124833 A1 | 5/2007 | Abad et al. |
| 2007/0141020 A1 | 6/2007 | Barritault et al. |
| 2007/0167441 A1 | 7/2007 | Halbrook et al. |
| 2007/0218102 A1 | 9/2007 | Chudzik et al. |
| 2007/0224247 A1 | 9/2007 | Chudzik et al. |
| 2007/0298071 A1 | 12/2007 | Harley et al. |
| 2008/0069774 A1 | 3/2008 | Liotta et al. |
| 2008/0090998 A1 | 4/2008 | Abad et al. |
| 2008/0131466 A1 | 6/2008 | Reed et al. |
| 2008/0247995 A1 | 10/2008 | Decarlo et al. |
| 2008/0248569 A1 | 10/2008 | Mata et al. |
| 2008/0293640 A1 | 11/2008 | Brophy et al. |
| 2009/0022771 A1 | 1/2009 | Lynn et al. |
| 2009/0030525 A1 | 1/2009 | Desrosiers et al. |
| 2009/0075281 A1 | 3/2009 | Hristova et al. |
| 2009/0092674 A1 | 4/2009 | Ingram et al. |
| 2009/0100536 A1 | 4/2009 | Adams et al. |
| 2009/0158452 A1 | 6/2009 | Johnson et al. |
| 2009/0162436 A1 | 6/2009 | Carson et al. |
| 2009/0183270 A1 | 7/2009 | Adams et al. |
| 2009/0202616 A1 | 8/2009 | Chong et al. |
| 2009/0324722 A1 | 12/2009 | Elisseeff |
| 2010/0003329 A1 | 1/2010 | Elisseeff |
| 2010/0004196 A1 | 1/2010 | De Agostini et al. |
| 2010/0017904 A1 | 1/2010 | Abad et al. |
| 2010/0021545 A1 | 1/2010 | Chaput et al. |
| 2010/0029549 A1 | 2/2010 | Chaput et al. |
| 2010/0111842 A1 | 5/2010 | Boyden et al. |
| 2010/0119577 A1 | 5/2010 | Min et al. |
| 2010/0137510 A1 | 6/2010 | Seliktar et al. |
| 2010/0166830 A1 | 7/2010 | Harley et al. |
| 2010/0210509 A1 | 8/2010 | Oh et al. |
| 2010/0227836 A1 | 9/2010 | Elisseeff et al. |
| 2011/0020298 A1* | 1/2011 | Panitch .......... A61L 27/24 424/93.7 |
| 2011/0038828 A1 | 2/2011 | Seliktar et al. |
| 2011/0087152 A1 | 4/2011 | David et al. |
| 2011/0207669 A1 | 8/2011 | Vandroux et al. |
| 2011/0214206 A1 | 9/2011 | La Rosa et al. |
| 2011/0238000 A1 | 9/2011 | Seliktar et al. |
| 2011/0258734 A1 | 10/2011 | Adams et al. |
| 2011/0269208 A1 | 11/2011 | Burdick et al. |
| 2012/0020911 A1 | 1/2012 | Seliktar et al. |
| 2012/0034164 A1 | 2/2012 | Ruoslahti et al. |
| 2012/0058943 A1 | 3/2012 | Werner et al. |
| 2012/0100106 A1 | 4/2012 | Panitch et al. |
| 2012/0227131 A1 | 9/2012 | Abad et al. |
| 2012/0246748 A1 | 9/2012 | Guo et al. |
| 2012/0258068 A1 | 10/2012 | Seliktar et al. |
| 2012/0294925 A1 | 11/2012 | Lynn et al. |
| 2013/0035307 A1 | 2/2013 | Prestwich et al. |
| 2013/0045926 A1 | 2/2013 | Devore et al. |
| 2013/0052155 A1 | 2/2013 | Marcolongo et al. |
| 2013/0074202 A1 | 3/2013 | Adams et al. |
| 2013/0101628 A1 | 4/2013 | Webber et al. |
| 2013/0109808 A1 | 5/2013 | Elisseeff |
| 2013/0116405 A1 | 5/2013 | Yu et al. |
| 2013/0152224 A1 | 6/2013 | Abad et al. |
| 2013/0190246 A1 | 7/2013 | Paderi et al. |
| 2013/0196896 A1 | 8/2013 | Komatsu et al. |
| 2013/0323311 A1 | 12/2013 | Paderi et al. |
| 2013/0333061 A1 | 12/2013 | Wu et al. |
| 2014/0011978 A1 | 1/2014 | Hubbell et al. |
| 2014/0170683 A1 | 6/2014 | Ling et al. |
| 2014/0288002 A1* | 9/2014 | Panitch .......... C07K 9/00 514/17.1 |
| 2014/0288022 A1 | 9/2014 | Elisseeff et al. |
| 2014/0301972 A1 | 10/2014 | Barritault et al. |
| 2014/0301983 A1 | 10/2014 | Panitch et al. |
| 2014/0369975 A1 | 12/2014 | Lee et al. |
| 2015/0031619 A1 | 1/2015 | Panitch et al. |
| 2015/0038425 A1 | 2/2015 | Paderi et al. |
| 2015/0038427 A1 | 2/2015 | Panitch et al. |
| 2015/0111308 A1 | 4/2015 | Yu et al. |
| 2016/0065083 A1 | 3/2016 | Mizutani et al. |
| 2016/0129076 A1 | 5/2016 | Panitch et al. |
| 2016/0166654 A1 | 6/2016 | Paderi et al. |
| 2016/0222064 A1 | 8/2016 | Panitch et al. |
| 2016/0229895 A1 | 8/2016 | Paderi et al. |
| 2016/0244495 A1 | 8/2016 | Panitch et al. |
| 2016/0331841 A1 | 11/2016 | Prestwich et al. |
| 2017/0043023 A1 | 2/2017 | Panitch et al. |
| 2017/0112941 A1 | 4/2017 | Panitch et al. |
| 2017/0275345 A1 | 9/2017 | Panitch et al. |
| 2017/0368192 A1 | 12/2017 | Paderi et al. |
| 2018/0030091 A1 | 2/2018 | Paderi et al. |
| 2018/0326077 A1 | 11/2018 | Panitch et al. |
| 2019/0022175 A1 | 1/2019 | Panitch et al. |
| 2020/0078469 A1* | 3/2020 | Prestwich .......... A61K 31/727 |

FOREIGN PATENT DOCUMENTS

| | | |
|---|---|---|
| EP | 1586652 A1 | 10/2005 |
| EP | 1677807 A2 | 7/2006 |
| EP | 2292773 A1 | 3/2011 |
| EP | 2295582 A2 | 3/2011 |
| JP | 2000-109500 | 4/2000 |
| JP | 2005185101 | 7/2005 |
| WO | WO-1992/012175 A1 | 7/1992 |
| WO | WO-1999/027105 A2 | 6/1999 |
| WO | WO-2001/019386 | 3/2001 |
| WO | WO-2005/055800 A2 | 6/2005 |
| WO | WO-2005/061018 A1 | 7/2005 |
| WO | WO-2005/082430 A1 | 9/2005 |
| WO | WO-2005/116066 A1 | 12/2005 |
| WO | WO-2006/047758 A1 | 5/2006 |
| WO | WO-2006/130974 A1 | 12/2006 |
| WO | WO-2007/044026 A2 | 4/2007 |

(56) References Cited

FOREIGN PATENT DOCUMENTS

| WO | WO-2007071448 | 6/2007 |
|---|---|---|
| WO | WO-2007-138291 A2 | 12/2007 |
| WO | WO-2008/034648 A1 | 3/2008 |
| WO | WO-2008/066816 A2 | 6/2008 |
| WO | WO-2008/070179 A2 | 6/2008 |
| WO | WO-2008/126092 A2 | 10/2008 |
| WO | WO-2008/152639 A2 | 12/2008 |
| WO | WO-2009/120995 A2 | 10/2009 |
| WO | WO-2010/033564 A1 | 3/2010 |
| WO | WO-2010/115156 A2 | 10/2010 |
| WO | WO-2010/122232 A1 | 10/2010 |
| WO | WO-2010/129547 A1 | 11/2010 |
| WO | WO-2010/139953 A1 | 12/2010 |
| WO | WO-2011/057286 A1 | 5/2011 |
| WO | WO-2011/094149 A1 | 8/2011 |
| WO | WO-2011/156445 A1 | 12/2011 |
| WO | WO-2011/163492 A1 | 12/2011 |
| WO | WO-2012/112767 A2 | 8/2012 |
| WO | WO-2012/162534 A2 | 11/2012 |
| WO | WO-2013/110056 A1 | 7/2013 |
| WO | WO-2014/028209 A1 | 2/2014 |
| WO | WO-2014/038866 A1 | 3/2014 |
| WO | WO-2014/040591 A2 | 3/2014 |
| WO | WO-2014/063102 A1 | 4/2014 |
| WO | WO-2014/071132 A1 | 5/2014 |
| WO | WO-2014/099997 A1 | 6/2014 |
| WO | WO-2014/144969 A1 | 9/2014 |
| WO | WO-2015/022326 A1 | 2/2015 |
| WO | WO-2015/078880 A1 | 6/2015 |
| WO | WO-2015/164822 A1 | 10/2015 |
| WO | WO-2015/175565 A2 | 11/2015 |
| WO | WO-2016/061145 A1 | 4/2016 |
| WO | WO-2016/061147 A1 | 4/2016 |
| WO | WO-2016/065083 A1 | 4/2016 |
| WO | WO-2016/161333 | 10/2016 |
| WO | WO-2016/168743 | 10/2016 |
| WO | WO-2017/066349 | 4/2017 |

OTHER PUBLICATIONS

Gresele, Platelets in Thrombotic and Non-thrombotic Disorders, 2002 (Year: 2002).*
Kolálová (Modulation of Endothelial Glycocalyx Structure under Inflammatory Conditions, Mediators of Inflammation 2014, of record) (Year: 2014).*
van Hinsbergh (Endothelium—role in regulation of coagulation and inflammation, Semin Immunopathol 2012, 34:93-106, epublished Aug. 4, 2011, of record) (Year: 2011).*
Gresele (Platelets in Thrombotic and Non-thrombotic Disorders, 2002, of record). (Year: 2002).*
Lievens (Platelets in atherosclerosis, Thromb Haemost 2011; 106: 827-838, of record) (Year: 2011).*
van Hinsbergh (Endothelium—role in regulation of coagulation and inflammation, Semin Immunopathol 2012, 34:93-106, epublished Aug. 4, 2011, of record). (Year: 2012).*
International Search Report and Written Opinion for PCT/US2015/027643 dated Sep. 29, 2015, 10 pages.
Scott et al., "Decorin Mimic Inhibits Vascular Smooth Muscle Proliferation and Migration", Plos One, vol. 8, Iss. 11, pp. 1-12, 2013.
Scott et al., "Water Soluble Polymer Films for Intravascular Drug Delivery of Antithrombotic Biomolecules", Eur J Pharm Biopharm, vol. 84, No. 1, pp. 125-131, 2013.
Stuart et al., "Collagen-Binding Peptidoglycans Inhibit MMP Mediated Collagen Degradation and Reduce Dermal Scarring", Plos One, vol. 6, Iss. 7, pp. 1-8, 2011.
A National Public Health Agenda for Osteoarthritis 2010, www.cdc.gov/arthritis/docs/OAagenda.pdf (2010).
Adiquzel et al., "Collagens in the progression and complications of atherosclerosis" Vascular Medicine. 14, 73-89. (2009).
Allaire et al., "Endothelial Cell Injury in Cardiovascular Surgery: The Intimal Hyperplastic Response" National Center for Biotechnology Information Ann Thorac Surg, 63(2). 582-91, (1997).

Ando, "Opinion Statement of the Effect of Mechanical Stress on Carilage Tissue Engineering" The Open Bone Journal, 2, 32-37 (2010).
Armstrong et al., "The Role of Matrix Metalloproteinases in Wound Healing" J Am Podiatr Med Assoc, 92(1), 12-18 (2002).
Ashcroft et al.; "Aging alters the inflammatory and endothelial cell adhesion molecule profiles during human cutaneous wound healing" Laboratory Investigation 78(1). 47-58, (1998).
Basser et al., "Mechanical Properties of the Collagen Network in Human Articular Cartilage as Measured by Osmotic Stress Technique" Archives of Biochemistry and Biophysics, 351(2), 207-219 (1998).
Bernhard et al,. "Synthesis and characterization of an aggrecan mimic" Acta Biomaterialia 8(4).1543-1550, (2012).
Bhide et al., "Collagen Phagocytosis by Fibroblasts Is Regulated by Decorin" J. Biol. Chem., 280(24), 23103-23113 (2005).
Bierbaum et al., "Collageneous Matrix Coatings on Titanium Implants Modified with Decorin and Chondroitin Sulfate: Characterization and Influence on Osteoblastic Cells" Journal of Biomedical Materials Research, 77A, 551-562. (2006).
Birch et al., "Animal Models for Adult Dermal Wound Healing" Methods in Molecular Medicine, 117, 223-235 (2005).
Braunwald et al., "The Problem of Persistent Platelet Activation in Acute Coronary Syndromes and Following Percutaneous Coronary Intervention" Clinical Cardiology. 31(3 Suppl. 1), I17-I20 ( 2008).
Brem et al., "Cellular and molecular basis of wound healing in diabetes," The Journal of Clinical Investigation, 117(5), 1219-22 (2007).
Broughton et al; "The basic science of wound healing." Plastic and Reconstructive Surgery 117(7S), 12S-34S (2006).
Business Wire "ZymoGenetics Reports New Findings on Anti-thrombotic Activities of CTRP1; Novel Protein Prevents Platelet Thrombosis without Causing Bleeding", www.thefreelibrary.com/ZymoGenetics+Reports+New+Findings+on+Anti-thrombotic+Activities+of+a0105542135, pp. 1-3 (2003).
Carney et al., "The Structure and Function of Cartilage Proteoglycans" Physiological Reviews, 68(3), 858-910 (1988).
Chiang et al., "A Synthetic Peptide Derived from the Sequence of a Type I Collagen Receptor Inhibits Type I Collagen-Mediated Platelet Aggregation" The Journal of Clinical Investigation, 100(8), 2079-2084 (1997).
Chiang et al., "Cloning, Characterization, and Functional Studies of a 47-kDa Platelet Receptor for Type III Collagen" The Journal of Biological Chemistry, 277( 38), 34896-34901 (2002).
Chiang et al., Cloning, Characterization, and Functional Studies of a Nonintegrin Platelet Receptor for Type I Collagen, J. Clin. Invest., vol. 100, No. 3, pp. 514-521, 1997.
Chiang et al., "Peptides Derived From Platelet Non-Integrin Collagen-Receptors or Types I and III Collagen Inhibit Collagen-Platelet Interaction" Cardiovascular & Haematological Disorders-Drug Targets, 7(1), 71-75 (2007).
Christner, "Studies on the properties of the inextricable proteoglycans from bovine nasal cartilage" J. Biol. Chem. 258, 14335-14341 (1983).
Chung et al., "Influence of gel properties on neocatilage formation by auricular chondrocytes photoencapsulated in hyaluronic acid networks" Journal of Biomedical Materials Research Part A, 77(3), 518-25 (2006).
Chung et al. "The influence of degradation characteristics of hyaluronic acid hydrogels on in vitro neocartilage formation by mesenchymal stem cells" Biomaterials, 30(26), 4287-96 (2009).
Chupa et al., "Vascular Cell Responses to Polysaccharide Materials: In Vitro and In Vivo Evaluations" Biomaterials, 21, 2315-2322 (2000).
Cremer, "The cartilage collagens: a review of their structure, organization and role in the pathogenesis of experimental arthritis in animals and in human rheumatic disease", J Mol Med, 76, 275-288, 1998.
Danielson et al., "Targeted Disruption of Decorin Leads to Abnormal Collagen Fibril Morphology and Skin Fragility" The Journal of Cell Biology, 136, 729-743 (1997).

(56) References Cited

OTHER PUBLICATIONS

Demling et al., "Small Intestinal Submucosa Wound Matric and Full-thickness Venous Ulcers: Preliminary Results" Wounds Research, 16(1), 18-22 (2004).
Di Mario et al. "The "Dark Side" of Percutaneous Coronary Interventions" Journal of the American College of Cardiology Interventions, 1(3):277-278 (2008).
Drachman et al., "Inflammation As a Mechanism and Therapeutic Target for In-stent Restenosis" Current Atherosclerosis Reports; 7(1), 44-49 (2005).
Extended European Search Report for EP11798931, completed Dec. 4, 2013.
Falanga, " Wound healing and its impairment in the diabetic foot," Lancet, 366 , 1736-43 (2005).
Farb et al. "Pathology of Acute and Chronic Coronary Stenting in Humans" Circulation, 99, 44-52 (1999).
FDA, "Guidance for Industry Chronic Cutaneous Ulcer and Burn Wounds Developing Products for Treatment" (Jun. 2006).
Flaumenhaft et al., "Extracellular Matrix Regulation of Growth Factor and Protease Activity" 1991, Current Opinion in Cell Biology, 3, 817-23 (1991).
Fransson et al., "Periodate Oxidation and Alkaline Degradation of Heparin-Related Glycans" Carbohydrate Research, 80, 131-145 (1980).
Fraser et al., "Hyaluronan: its nature, distribution, functions and turnover" Journal of Internal Medicine, 242, 27-33 (1997).
Fulzele et al., "Study of the Biodegradation and in Vivo Biocompatibility of Novel Biomaterials," European Journal of Pharmaceutical Sciences, vol. 20, 2003, pp. 53-61.
Gallant et al., "Cytokine and Growth Factor mRNA Expression Patterns Associated with the Hypercontracted, Hyperpigmented Healing Phenotype of Red Duroc Pigs: A Model of Abnormal Human Scar Development?" J Cutan Med Surg, 9(4), 165-177 (2005).
Gallant et al., "Molecular, histologic, and gross phenotype of skin wound healing in red Duroc pigs reveals an abnormal healing phenotype of hypercontracted, hyperpigmented scarring" Wound Rep Reg, 12, 305-319 (2004).
Geng et al., "SLRP interaction can protect collagen fibrils from cleavage by collagenases" Matrix Biology, 25, 484-491 (2006).
Gercken et al., "Results of the Jostent Coronary Stent Graft Implantation in Various Clinical Settings: Procedural and Follow-Up Results." Catheterization and Cardiovascular Interventions 56:353-360 (2002).
Gerwin, "Intraarticular drug delivery in osteoarthritis" Advanced Drug Delivery Reviews, 58, 226-242 (2006).
Ghosh et al., "The Effects of Intraarticular Administration of Hyaluronan in a Model of Early Osteoarthritis in Sheep I. Gait Analysis and Radiological and Morphological Studies" Seminarsin Arthritisand Rheumatism, 22(6), 18-30 (1993).
Goldoni et al; "Biologically active decorin is a monomer in solution." J. Bio. Chem. 279(8), 6606-6612 (2004).
Grassl et al., "Fibrin as an Alternative Biopolymer to Type-1 Collagen for the Fabrication of a Media Equivalent" Journal of Biomedical Materials Research, 60(4), 607-612, (2002).
Griese et al., "Isolation and Transplantation of Autologous Circulating Endothelial Cells Into Denuded Vessels and Prosthetic Grafts: Implications for Cell-Based Vascular Therapy," Circulation. 2003;108:2710-2715.
Griffey et al., "Particulate Dermal Matrix as an Injectable Soft Tissue Replacement Material" J. Biomed. Mater. Res., 58, 10-15 (2001).
Gutman et al., "Liposomal alendronate for the treatment of restenosis" Journal of Controlled Release, 161, 619-627 (2012).
Hantgan et al., "Platelets Interact With Fibrin Only After Activation," Blood, vol. 65, No. 6 (June). 1985: pp. 1299-1311.
Helms et al. "High affinity peptide based collagen targeting using synthetic phage mimics: from phage display to dendrimerdisplay." J. Am. Chem. Soc. 131, 11683-11685 (2009).

Hemmer et al; "Minimal peptide length requirements for cd4+ t cell clones—implications for molecular mimicry and t cell survival." Int. Immunol., 12(3) 375-383 (2000).
Henn et al; "CD40 lignd on activated platelets triggers an inflammatory reaction of endothelial cells." Nature, 391 591-594 (1998).
Henrotin et al., "Intra-articular use of a medical device composed of hyaluronic acid and chondroitin sulfate (Structovial CS): effects on clinical, ultrasonographic and biological parameters" BMC Research Notes, 5(407), 1-7 (2012).
Hermanson, "Zero-Length Cross-Linkers" Academic Press, 169-186 (1996).
Hollander et al., "Increased Damage to Type II Collagen in Osteoarthritic Articular Cartilage Detected by a New Immunassay" J. Clin. Invest., 93, 1722-1732 (1994).
Huang et al., "Aggrecanase and Aggrecan Degradation in Osteoarthritis: a Review" The Journal of International Medical Research, 36, 1149-1160 (2008).
Huizinga et al., "Crystal structure of the A3 domain of human von Willebrand factor: implications for collagen binding," Structure 1997, vol. 5 No. 9, pp. 1147-1156.
Hunt et al., "Respiratory Gas Tensions and pH in Healing Wounds" American Journal of Surgery, 114, 302-307, (1967).
International Search Report and Written Opinion for PCT/US2010/033543 dated Oct. 8, 2010.
International Preliminary Examination Report and Written Opinion for PCT/US2012/039404 dated Nov. 26, 2013.
International Preliminary Examination Report issued in International PCT application No. PCT/US2009/038624 dated Sep. 28, 2010.
International Preliminary Report on Patentability for International Application No. PCT/US2015/027643, dated Oct. 25, 2016. (6 pages).
International Search Report and Written Opinion for PCT/US2011/041654, dated Oct. 26, 2011.
International Search Report and Written Opinion issued in International Application No. PCT/US2012/039404 dated Nov. 29, 2012.
International Search Report Opinion for PCT/US2014/029596, dated Jul. 28, 2014.
Järveläinen et al., "A role for decorin in cutaneous wound healing and angiogenesis" Wound Rep Reg, 14, 443-452 (2006).
Järvinen et al., "Target-seeking antifibrotic compound enhances wound healing and suppresses scar formation in mice" PNAS, 107(50), 21671-21676 (2010).
Julienne, et al., "Topical Treatment with a New Matrix Therapy Agent (RGTA, CACICOL-20) Improves Epithelial Wound Healing After Penetrating Keratoplasty," Acta Ophthalmologica, 2014, 92(s253).
Kalamajski et al., "The Decorin Sequence SYIRIADTNIT Binds Collagen Type 1" Journal of Biological Chemistry, 282(22), 16062-16067 (2007).
Kalamajski, "The role of small leucine-rich proteoglycans in collagen fibrillogenesis" Matrix Biology, 29(4), 248-253 (2010).
Kapoor, "Role of proinflammatory cytokines in the pathophysiology of osteoarthritis" Nat. Rev. Rheumatol, 7, 33-42 (2011).
Khorramizadeh et al., "Aging differentially modulates the expression of collagen and collagenase in dermal fibroblasts" Molecular and Cellular Biochemistry, 194, 99-108 (1999).
Kiani et al., "Review: Structure and function of aggrecan" Cell Research 12(1), 19-32 (2002).
Kipshidze et al., "Role of the Endothelium in Modulating Neointimal Formation" Journal of the American College of Cardiology, 44(4), 733-739 (2004).
Kirker, et al., "Glycosaminoglycan Hydrogel Films as Biointeractive Dressings for Wound Healing," Biomaterials, 23(17):3661-3671.
Kitov, "On the nature of the multivalency effect: a thermodynamic model." J. Am. Chem. Soc., 125, 16271-16284 (2003).
Klatt, "A Critical Role for Collagen II in Cartilage Matrix Degradation: Collagen II Induces Pro-Inflammatory Cytokines and MMPs in Primary Human Chondrocytes" J. Orthop Res (27) 65-70 (2009).
Knudson, "Cartilage Proteoglycans" Cell & Developmental Biology, 12, 69-78 (2001).

(56) References Cited

OTHER PUBLICATIONS

Kraus et al., "The OARSI Histopathology Initiative—Recommendations for Histological Assessments of Osteoarthritis in the Guinea Pig" Osteoarthritis Cartilage, 18(Suppl. 3), S35-S52 (2010).
Kraut et al., "Challenges in Enzyme Mechanism and Energetics," Annu. Rev. Biochem., 72, 2003, pp. 517-571.
Larroque et al. (2013), "New matrix therapy in chronic corneal ulcers resistant to conventional therapies," Acta Ophthalmologica, 91(5252):0.
Lasser, Blood, 2006, 107, 423-430.
Lazic et al., "Bioengineered Skin Constructs and Their Use in Wound Healing" 2010, Plastic and Reconstructive Surgery, 127(1S), 75S-90S (2010).
Le Tourneau et al., "Dose Escalation Methods in Phase I Cancer Clinical Trials," J Natl Cancer Inst 2009;101:708-720.
Lee et al., "Dark Quenched Matrix Metalloproteinase Fluorogenic Probe for Imaging Osteoarthritis Development In Vivo" Bioconjugate Chemistry, 19(9), 1743-1747 (2008).
Lee et al. "Enhanced chondrogenesis of mesenchymal stem cells in collagen mimetic peptide-mediated microenvironment" Tissue Engineering Part A, 14(11) 1843-51 (2008).
Lee et al., "Injectable gel with synthetic collagen-binding peptide for enhanced osteogenesis in vitro and in vivo," Biochemical and Biophysical Research Communications 357 (2007) 68-74.
Lee et al., "Effect of glucosamine or chondroitin sulfate on the osteoarthritis progression: a meta-analysis" Rheumatol Int., 30, 357-363 (2010).
Lee et al., "Polymeric Nanoparticle-Based Activatable Near-Infrared Nanosensor for Protease Determination In Vivo" Nano Lett., 9(12), 4412-4416 (2009).
Lemon et al., "Immunoprecipitation and Virus Neutralization Assays Demonstrate Qualitative Differences between Protective Antibody Responses to Inactivated Hepatitis A Vaccine and Passive Immunization with Immune Globulin," The Journal of Infectious Diseases 1997;176:9-19.
Libby et al. "A Cascade Model for Restenosis—A Special Case of Atherosclerosis Progression" Circulation., 86(6), III-47-III-52 (1992).
Lynn, et al., "Design of a Multiphase Osteochondral Scaffold. I. Control of Chemical Composition," J Biomed Mater Res A, 2010, 92(3):1057-1065.
Madry et al., "Biological aspects of early osteoarthritis" Knee Surg Sports Traumator Arthrosc, 20, 407-422 (2012).
Madsen et al., "Aggrecanase- and matrix metalloproteinase-mediated aggrecan degradation is associated with different molecular characteristics of aggrecan and separated in time ex vivo," Biomarkers, 2010; 15(3): 266-276.
Mammen et al., "Polyvalent interactions in Biological Systems: Implications for Design and Use of Multivalent Ligands and Inhibitors" Angew. Chem. Int. Ed., 37, 2754-2794 (1998).
Maroudas, "Balance between Swelling pressure and collagen tension in normal and degenerate cartilage" Nature, 260, 808-809 (1976).
Martil-Pelletier, "Review: Future therapeutics for osteoarthritis", Bone, 51, 297-311, 2012.
Martin, "Wound Healing-Aiming for Perfect Skin Regeneration," Science, vol. 276, 1997.
Masuko et al., "Anti-inflammatory effects of hyaluronan in arthritis therapy: Not just for viscosity" International Journal of General Medicine, 2, 77-81 (2009).
Moustafa et al., "A new autologous keratinocyte dressing treatment for non-healing diabetic neuropathic foot ulcers," Diabet. Med. 21, 786-789 (2004).
Mummert et al., "Development of a Peptide Inhibitor of Hyaluronan-mediated Leukocyte Trafficking" J. Exp. Med., 192(6), 769-779 (2000).
Mummert, "Immunological Roles of Hyaluronan" Immunologic Research, 31 (3), 189-205 (2005).
Nagase et al., "Review: Aggrecanases and cartilage matrix degradation" Arthritis Research & Therapy, 5(2) 94-103 (2003).

Nia et al., "High-Bandwidth AFM-Based Rheology Reveals that Cartilage is Most Sensitive to High Loading Rates at Early Stages of Impairment" Biophysical Journal, 104, 1529-1537 (2013).
Nili et al., "Decorin inhibition of PDGF-stimulated vascular smooth muscle cell function: potential mechanism for inhibition of intimal hyperplasia after balloon angioplasty" The American Journal of Pathology, 163(3), 869-878 (2003).
O'Brien, et al., "The Effect of Pore Size on Cell Adhesion in Collagen-GAG Scaffolds," Biomaterials, 2005, 26(4):433-441.
Ogden, "Clinical responses to new and reprocessed hemodialyzers." Guide to Reprocessing of Hemodialyzers 87-97 (1986).
Orbusneich, "About the Combo Dual Therapy Stent".
Oyama et al., "Isolation of lung tumor specific peptides from a random peptide library: generation of diagnostic and cell-targeting reagents," Cancer Letters 202 (2003) 219-230.
Paderi et al., "Collagen-Binding Peptidoglycans: A Biomimetic Approach to Modulate Collagen Fibrillogenesis for Tissue Engineering Applications" Tissue Engineering Part A, 15(10), 2991-2999 (2009).
Paderi et al., "Design of a Synthetic Collagen-Binding Peptidoglycan that Modulates Collagen" Fibrillogenesis. Biomacromolecules 9, 2562-2566 (2008).
Paderi, "Design of collagen binding proteoglycan mimics." Thesis (Aug. 2008).
Paderi, et al., "The Inhibition of Platelet Adhesion and Activation on Collagen During Balloon Angioplasty by Collagen-Binding Peptidoglycans" Biomaterials, 32, 2516-2523 (2011).
Penc et al., "Dermatan Sulfate Released after Injury Is a Potent Promoter of Fibroblast Growth Factor-2 Function" The Journal of Biological Chemistry, 273(43), 28116-28121 (1998).
Pentikainen et al; "The proteoglycan decorin links low density lipoproteins with collagen type I." J. Bio. Chem. 272(12), 7633-7638 (1997).
Pieper et al., "Development of Tailor-Made Collagen-Giycosaminoglycan Matrices: EDC/NHS Crosslinking, and Ultrastructural Aspects" Biomaterials, 21, 581-593 (2000).
Pierce Biotechnology catalog (2005/2006).
Pignatelli et al; "Hydrogen peroxide is involved in collagen induced platelet activation" Blood, 91 (2) 484-490 (1998).
Pizzo et al., "Extracellular Matrix (ECM) Microstructural Composition Regulates Local Cell-ECM Biomechanics and Fundamental Fibroblast Behavior: A Multidimensional Perspective" Journal Appl. Physiol, 98, 1909-1921 (2005).
Place et al., (2014), "Aggrecan-mimetic, glycosaminoglycan-containing nanoparticles for growth factor stabilization and delivery," Biomacromolecules, 15(2):680-689.
Place et al., (2014), "Synthesis and characterization of proteoglycan-mimetic graft copolymers with tunable glycosaminoglycan density," Biomacromolecules, 15(10):3772-3780.
Pratta et al., "Aggrecan Protects Cartilage Collagen from Proteolytic Cleavage" J. Biol. Chem., 278(46), 45539-45545 (2003).
Puig et al., "A new decorin-like tetrapeptide for optimal organization of collagen fibres" International Journal of Cosmetic Science, 30, 97-104 (2008).
Radek et al., "FGF-10 and specific structural elements of dermatan sulfate size and sulfation promote maximal keratinocyte migration and cellular proliferation" Wound Rep Reg, 17, 118-126 (2009).
Ratcliffe, Anthony, "Tissue engineering of vascular grafts," Matrix Biology 19 (2000) 353-357.
Reed et al., "The role of decorin in collagen fibrillogenesis and skin homeostasis" Glycoconjugate Journal, 19, 249-255 (2003).
Roeder et al., "Tensile Mechanical Properties of Three-Dimensional Type I Collagen Extracellular Matrices With Varied Microstructure," Transactions of the ASME vol. 124, 2002, pp. 214-222.
Romijn et al., "Mapping the Collagen-Binding Site in the Von Willebrand Factor-A3 Domain" The Journal of Biological Chemistry, 278(17), 15035-15039 (2003).
Roseborough et al; "Prevention and treatment of excessive dermal scarring." J. Natl. Med. Assoc., 96,108-116(2004).
Rosenblum et al., "Diminished Benefits of Drug-Eluting Stents versus Bare Metal Stents in Patients with Severe Renal Insufficiency" Nephron Clinical Practice, 113, c198-c202, (2009).

(56) References Cited

OTHER PUBLICATIONS

Rossi et al; "Decontamination of surfaces by low pressure plasma discharges" Plasma Process. Polym. 3, 431-442 (2006).
Roth et al; "Localization of binding sites within human von willebrand factor for monomeric type III collagen." Biochemistry 25, 8357-8361 (1986).
Roy-Chaudhury et al. "Hemodialysis Vascular Access Dysfunction: A Cellular and Molecular Viewpoint" J AM Sco Nephrol, 17(4),1112-1127 (2006).
Rudbach et al., "Physical Aspects of Reversible Inactivation of Endotoxin," Annals New York Academy of Sciences, (1966) 133, pp. 629-643.
Rutjes et al., "Viscosupplementation for Osteoarthritis of the Knee: A Systematic Review and Meta-analysis" Ann Intern Med., (157), 180-191 (2012).
Santa Cruz Biotechnology listing for phosphate buffered saline (http://www.scbt.com/datasheet-362182.html, downloaded Feb. 10, 2014).
Saxena, et al., "Enhancing the survival of tunneled haemodialysis catheters using an antibiotic lock in the elderly: a randomized, double blind clinical trial." Nephrology 11, 299-305 (2006).
Schilling et al., "Wound Healing: A Comparative Study of the Histochemical Changes in Granulation Tissue Contained in Stainless Steel Wire Mesh and Polyvinyl Sponge Cylinders" Surgery, 46(4), 702-710 1959.
Schmitz et al., "Hyaluronan oligosaccharide treatment of chondrocytes stimulates expression of both HAS-2 and MMP-3, but by different signaling pathways" Osteoarthritis Cartilage 18(3) 447-454 (2010).
Schonherr et al., "Decorin Core Protein Fragment LEU 155-Val260 Interacts with TGF-Beta But Does Not Compete for Decorin Binding to Type I Collagen" Arch. Biochem. Biophys., 355(2), 241-248 (1998). Abstract Only.
Schultz et al., "Interactions between extracellular matrix and growth factors in wound healing," Wound Rep Reg (2009) 17, 153-162.
Scott et al., "Molecular and Cellular Aspects of Fibrosis Following Thermal Injury" Thermal Injuries, 16(2), 271-287 (2000).
Scott et al., "Chemical characterization and quantification of proteoglycans in human post-burn hypertrophic and mature scars" Clinical Science, 90(5), 417-25 (1996).
Scott et al., "Decorin mimic inhibits vascular smooth muscle proliferation and migration" PLOS One, 8(11): e82456. (2013).
Scott et al., "Dermatan sulphate-rich proteoglycan associates with rat tail-tendon collagen at the d band in the gap region" Biochem. J., 197(1), 213-216 (1981).
Scott et al., "Proteoglycan-fibrillar collagen interactions" Biochem. J, 252, 313-323 (1988).
Sharma et al., "Biomimetic Aggrecan Reduces Cartilage Extracellular Matrix From Degradation and Lowers Catabolic Activity in Ex Vivo and In Vivo Modelsa" Macromolecular Bioscience, DOI 10.1002, 1-10 (2013).
Shin et al., "A novel collagen-binding peptide promotes osteogenic differentiation via Ca2+/calmodulin-dependent protein kinase II/ERK/AP-1 signaling pathway in human bone marrow-derived mesenchymal stem cells," Cellular Signalling 20 (2008) 613-624.
Singer et al., "Cutaneous Wound Healing" The New England Journal of Medicine, 341(10), 738-46 (1999).
Sini et al; "Role of decorin on in vitro fibrillogenesis of type 1 collagen." Glycoconj. J. 14, 871-874 (1997).
Smith Jr. et al., "Effect of Intraarticular Hyaluronan Injection in Experimental Canine Osteoarthritis" Arthritis & Rheumatism, 41(6), 976-985 (1998).
Suki et al., "Biomechanics of the lung parenchyma: critical roles of collagen and mechanical forces," J Appl Physiol 98: 1892-1899, 2005.
Svensson et al., "Decorin-binding Sites for Collagen Type I Are Mainly Located in Leucine-rich Repeats 4-5," vol. 270, No. 35, pp. 20712-20716, 1995.
Taylor et al., "Structural and Sequence Motifs in Dermatan Sulfate for Promoting Fibroblast Growth Factor-2 (FGF-2) and FGF-7 Activity" The Journal of Biological Chemistry, 280(7), 5300-5306 (2005).
Tenni et al., "Interaction of Decorin with CNBr Peptides from Collagens I and II Evidence for Multiple Binding Sites and Essential Lysyl Residues in Collagen" Eur. J. Biochem., 269, 1428-1437 (2002).
The USRDS Coordinating, "Incidence, prevalence, patient characteristics, and treatment modality" Center United States Renal Data System, 2, 215-228 (2013).
Tollefsen, "Vascular Dermatan Sulfate and Heparin Cofactor II" Progress in Molecular Biology and Translational Science, 93, 351-372 (2010).
Trengove et al., "Analysis of the acute and chronic wound environments: the role of proteases and their inhibitors" Wound Rep Reg, 7(6), 442-452 (1999).
Trowbridge et al., "Dermatan Sulfate Binds and Potentiates Activity of Keratinocyte Growth Factor (FGF-7)" The Journal of Biological Chemistry, 277(45), 42815-42820 (2002).
Trowbridge et al., "Dermatan sulfate: new functions from an old glycosaminoglycan," Glycobiology vol. 12 No. 9 pp. 117R-125R, 2002.
Umlauf et al., "Cartilage biology, pathology, and repair" Cell. Mol. Life Sci., 67, 4197-4211 (2010).
Uniprot/Trembl Q7Z4J1, "Nonintegrin Platelet Receptor for Type I Collagen", Last Modified Feb. 10, 2009, Available on the Internet <URL: http://www.uniprot.org/uniprot/Q7Z4J1 &format=html.
UniProtKB—P21793, Decorin precursor Bos taurus (Bovine), Jul. 5, 2005. Available on the Internet http://www.uniprot.org/uniprot/P21793.
Uniprotkb, "Decorin Precursor-Bas Taurus (Bovine)", Last Modified Sep. 1, 2009, Available on the Internet <URL: http://www. uniprot.org/uniprot/P21793>.
UniProtKB/TrEMBL Q7Z4J1, Nonintegrin platelet receptor for type I collagen, Oct. 1, 2003. Available on the internet http://www.uniprot.org/uniprot/Q7Z4J1&format=html.
Van Neck et al., (2012), "Heparan Sulfate Proteoglycan Mimetics Promote Tissue Regeneration: An Overview," Chapter 4 in J Davies (Ed.), Tissue Regeneration—From Basic Biology to Clinical Application, 69-92, InTech—Open Access Publisher, doi: 10.5772/25622.
Velander et al., "Impaired wound healing in an acute diabetic pig model and the effects of local hyperglycemia" Wound Rep Reg, 16, 288-93 (1999).
Vogel et al., "Specific. inhibition of type I and type II collagen fibrillogenesis by the small proteoglycan of tendon," Biochem. J. (1984) 223, 587-597.
Wang et al., "Deep dermal fibroblasts contribute to hypertrophic scarring" Laboratory Investigation, 88, 1278-1290 (2008).
Wang et al., "Venous stenosis in a pig arteriovenous fistula model-anatomy, mechanisms and cellular phenotypes" Nephrol Dial Transplace, 23:525-533 (2008).
Wang, et al., "Platelet, Not Endothelial, P-Selection is Required for Neointimal Formation After Vascular Injury," Arterioscler Thromb. Vase. Biol., 25, 2005, pp. 1584-1589.
VVidgerow et al., "Multimodality Scar Management Program," Aesth Plast Surg (2009) 33:533-543.
Williams, et al., "Collagen Fibril Formation," J. Biol. Chem., 253(18), 1978, pp. 6578-6585.
Vvysocki et al., "Wound Fluid from Chronic Leg Ulcers Contains Elevated Levels of Metalloproteinases MMP-2 and MMP-9" The Society for Investigative Dematology, Inc., 101(1), 64-68 (1993).
Yampolsky, et al., "The Exchangeability of Amino Acids in Proteins." Genetics (2005) 170, p. 1459-1472.
Zhang et al., (2014), "Preservation of the structure of enzymatically-degraded bovine vitreous using synthetic proteoglycan mimics," Invest Ophthalmol Vis Sci, 55:8153-8162.
Zhu et al., "Further similarities between cutaneous scarring in the female, red Duroc pig and human hypertrophic scarring," Burns 30 (2004) 518-530.
Zhu et al., "The female, red Duroc pig as an animal model of hypertrophic scarring and the potential role of the cones of skin" Burns, 29, 649-664 (2003).

(56) References Cited

OTHER PUBLICATIONS

Zhu et al., "Review of the female Duroc/Yorkshire pig model of human fibroproliferative scarring" Wound Rep. Reg., 15, S32-S39 (2007).
Zustiak et al., "Influence of Cell-Adhesive Peptide Ligands on Poly(ethylene glycol) Hydrogel Physical, Mechanical and Transport Properties," Acta Biomater. 2010; 6(9): 3404-3414.
Kadler et al., Collagen fibril formation, Biochem. J. 1996, 316, pp. 1-11.
Ruotsalainen et al., Glycosylation catalyzed by lysyl hydroxylase 3 is essential for basement membranes, Journal of Cell Science 2006, 119, pp. 625-635.
Winterton et al. (1986) Heparin Interaction with Protein-Adsorbed Surfaces, J. Colloid Interface Sci., vol. 111, pp. 314-342.

* cited by examiner

SEQUENCE LISTING

```
<160> NUMBER OF SEQ ID NOS: 58

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Gly
1

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Ala Asn Ala Ala Leu Lys Ala Gly Glu Leu Tyr Lys Ser Ile
1               5                   10                  15

Leu Tyr

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Leu Asp Gly Asn Glu Ile Lys Arg
1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala His Glu Glu Ile Ser Thr Thr Asn Glu Gly Val Met
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Glu Leu Tyr Lys Ser Ile Leu Tyr
1               5

<210> SEQ ID NO 6
<211> LENGTH: 28
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 6

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln
            20                  25

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gln Asp Ser Glu Thr Arg Thr Phe Tyr
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Lys Lys Thr Leu Arg Thr
1               5

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met
            20                  25

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gln Asn Pro Val Gln Pro
1               5

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Ser Tyr Ile Arg Ile Ala Asp Thr Asn Ile Thr
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Glu Leu Asn Leu Val Tyr Thr
1               5

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Ile Thr Thr Ile Asp Val Pro Trp Asn Val Gly Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Ile Thr Thr Ile Asp Val Pro Trp Asn Val
1               5                   10

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Ala Asn Ala Ala Leu Lys Ala Gly Glu Leu Tyr Lys Cys Ile
1               5                   10                  15

Leu Tyr

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Glu Leu Tyr Lys Cys Ile Leu Tyr
1               5
```

```
<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Ala Asn Ala Ala Leu Lys Ala Gly Glu Leu Tyr Lys Ser Ile
1               5                   10                  15

Leu Tyr Gly Cys
            20

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Leu Asp Gly Asn Glu Ile Lys Arg Gly Cys
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala His Glu Glu Ile Ser Thr Thr Asn Glu Gly Val Met Gly Cys
1               5                   10                  15

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln Gly Cys
            20                  25                  30

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Lys Lys Thr Leu Arg Thr Gly Cys
1               5

<210> SEQ ID NO 22
<211> LENGTH: 30
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 22

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met Gly Cys
            20                  25                  30

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gln Asn Pro Val Gln Pro Gly Cys
1               5

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Tyr Ile Arg Ile Ala Asp Thr Asn Ile Thr Gly Cys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Glu Leu Asn Leu Val Tyr Thr Gly Cys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Glu Leu Tyr Lys Ser Ile Leu Tyr Gly Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gly Cys Gly Gly Glu Leu Tyr Lys Ser Ile Leu Tyr
1               5                  10
```

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Trp Arg Glu Pro Ser Phe Cys Ala Leu Ser
1               5                  10
```

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (16)..(16)
<223> OTHER INFORMATION: Bip

<400> SEQUENCE: 29

```
Ala Trp His Cys Thr Thr Lys Phe Pro His His Tyr Cys Leu Tyr Xaa
1               5                  10                  15
```

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (17)..(17)
<223> OTHER INFORMATION: Bip

<400> SEQUENCE: 30

```
Ala His Lys Cys Pro Trp His Leu Tyr Thr Thr His Tyr Cys Phe Thr
1               5                  10                  15

Xaa
```

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 31

Ala His Lys Cys Pro Trp His Leu Tyr Thr His Tyr Cys Phe Thr
1               5                   10                  15

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline

<400> SEQUENCE: 32

Gly Arg Xaa Gly Glu Arg
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline

<400> SEQUENCE: 33

Gly Met Xaa Gly Glu Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline

<400> SEQUENCE: 34

Gly Leu Xaa Gly Glu Asn
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline

<400> SEQUENCE: 35

Gly Leu Xaa Gly Glu Arg
1               5

<210> SEQ ID NO 36
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 36

Gly Leu Lys Gly Glu Asn
1               5

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline
<220> FEATURE:
<221> NAME/KEY: MOD_RES
<222> LOCATION: (12)..(12)
<223> OTHER INFORMATION: 4-hydroxyproline

<400> SEQUENCE: 37

Gly Phe Xaa Gly Glu Arg Gly Val Glu Gly Pro Xaa Gly Pro Ala
1               5                   10                  15

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His Val Trp Met Gln Ala Pro Gly Gly Gly Lys
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Tyr Arg Gly Arg Leu
1               5

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Thr Cys Ser Gly Asp Glu Tyr Thr Trp His Cys
1               5                   10

<210> SEQ ID NO 41
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 41

Trp Thr Cys Val Gly Asp His Lys Thr Trp Lys Cys
1               5                   10

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Trp His Cys Thr Thr Arg Phe Pro His His Tyr Cys Leu Tyr Gly
1               5                   10                  15

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Thr Trp Thr Trp Asn Gly Ser Ala Trp Thr Trp Asn Glu Gly Gly
1               5                   10                  15

Lys

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Thr Trp Thr Trp Asn Gly Thr Asn Trp Thr Arg Asn Asp Gly Gly
1               5                   10                  15

Lys

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Val Trp Leu Trp Glu Gln Cys
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46
```

Cys Met Thr Ser Pro Trp Arg Cys
1               5

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Pro Gly Arg Val Met His Gly Leu His Leu Gly Asp Asp Glu Gly
1               5                   10                  15

Pro Cys

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Leu Trp Leu Leu Pro Lys
1               5

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Tyr Pro Ile Ser Arg Pro Arg Lys Arg Gly Ser Gly
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Gln Asp Ser Glu Thr Arg Thr Phe Tyr Gly Cys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Cys Gly Gly Glu Leu Tyr Lys Ser Ile Leu Tyr Gly Cys
1               5                   10

<210> SEQ ID NO 52
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Arg Arg Ala Asn Ala Ala Leu Lys Ala Gly Glu Leu Tyr Lys Ser
1               5                   10                  15

Ile Leu Tyr Gly Cys
            20

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Tyr Ile Arg Ile Ala Asp Thr Asn Ile Thr
1               5                   10

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Gly
1

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Gly Gly Gly
1               5

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Ser Gly Cys
1

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 57

Gly Ser Gly Ser Gly
1               5

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Gly Cys
1
```

COLLAGEN BINDING SYNTHETIC PEPTIDOGLYCANS FOR TREATMENT OF ENDOTHELIAL DYSFUNCTION

CROSS-REFERENCE TO RELATED APPLICATIONS

This application is a U.S. national stage application of PCT/US2015/027643, filed Apr. 24, 2015, which application claims the benefit of U.S. Application No. 61/984,452, filed Apr. 25, 2014, the contents of which are incorporated by their entirety herein by reference.

STATEMENT AS TO FEDERALLY SPONSORED RESEARCH OR DEVELOPMENT

This invention was made with government support under HL106792 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Apr. 5, 2017, is named 44JR-209736-US_SL.txt and is 15,738 bytes in size.

TECHNICAL FIELD

The present disclosure generally relates to synthetic peptidoglycan compositions and related methods for treating diseases associated with endothelial dysfunction.

BACKGROUND

This section introduces aspects that may help facilitate a better understanding of the disclosure. Accordingly, these statements are to be read in this light and are not to be understood as admissions about what is or is not prior art.

Intimal hyperplasia forms as a result of blood vessel damage and disease. In damaged vessels, platelets bind to and become activated on exposed collagen within the blood vessel. The activated platelets support thrombus formation, release inflammatory cytokines and recruit monocytes from the blood into the vessel tissue. The monocytes then secrete factors including cytokines that stimulate smooth muscle cell (SMC) migration into the intimal layer, and extracellular matrix (ECM) secretion, culminating in intimal hyperplasia. Dysfunctional endothelium, which is present in all diabetic patients due to uremia and other metabolic disorders, support platelet binding and activation similar to exposed collagen. In addition, dysfunctional and damaged endothelium supports leukocyte migration from blood into the blood vessel wall. Dysfunctional endothelium also loosens cell-cell junctions, causing them to become leaky due to gaps between the cell membranes, and potentially exposes underlying collagen in these gaps, which is then accessible to platelet binding. Thus, exposed collagen present due to loss of endothelial cells (ECs), as a result of mechanical vessel damage during handling, and dysfunctional and damaged ECs, supports intimal hyperplasia.

Loss of glycocalyx, the anionic glycosaminoglycan layer covering the endothelium is a hallmark of dysfunctional endothelium and inflammation. Loss of the glycocalyx unmasks cell surface receptors including ICAM and VCAM, which are expressed in chronic inflammation and endothelial cell (EC) dysfunction. Glycocalyx loss also exposes receptors P-selectin and E-selectin, which are transiently expressed on the cell surface due to damage and inflammation, and chronically expressed in dysfunctional endothelium as is the case in diabetic patients. The selectins facilitate leukocyte rolling on the ECs, which is the first step to monocyte and neutrophil migration into the vessel wall. Following rolling, the leukocytes bind more firmly to ICAM and VCAM. They then migrate into the tissue where they release cytokines, and stimulate SMC migration to the intima and ECM synthesis. The end result is intimal hyperplasia, which prevents outward remodeling and can promote long-term thrombosis.

SUMMARY OF THE DISCLOSURE

The present disclosure, in one embodiment, provides methods for treating a patient suffering from a disease associated with endothelial dysfunction. Also provided, in one embodiment, is a method for treating or inhibiting endothelial dysfunction in a patient in need thereof.

In some aspects, the method entails administering to the patient a pharmaceutical composition comprising an effective amount of a synthetic peptidoglycan. In some aspects, the synthetic peptidoglycan comprises a glycan having from about 1 to about 80 collagen binding peptide(s) bonded to the glycan.

Non-limiting examples of diseases associated with endothelial dysfunction include atherosclerosis, coronary artery disease, diabetes mellitus, hypertension, hypercholesterolemia, rheumatoid arthritis, systemic lupus erythematosus, glaucoma, uremia, sepsis, and organ failure.

In some aspects, the administration is intravenous, intraperitoneal, topical or through an implanted device.

In some aspects, the patient is not undergoing or recovering from a vascular intervention procedure. In some aspects, the vascular intervention procedure comprises a percutaneous coronary intervention (PCI) procedure. In some aspects, the vascular intervention procedure comprising denuding a blood vessel.

In some aspects, the endothelial dysfunction is characterized by permeated endothelial lining or damaged endothelial cells. In some aspects, the endothelial dysfunction is characterized by loss of glycocalyx. In some aspects, the endothelial dysfunction is characterized by a selectin protein expressed on the surface of endothelial cells and exposed to circulation. In some aspects, the site suffers from inflammation.

In some aspects, the glycan is dextran, chondroitin, chondroitin sulfate, dermatan, dermatan sulfate, heparan sulfate, heparin, keratin, keratan sulfate, or hyaluronic acid. In some aspects, the peptide(s) are covalently bonded to the glycan via a linker. In some aspects, the linker is N-[β-maleimidopropionic acid]hydrazide (BMPH), 3-(2-pyridyldithio)propionyl hydrazide (PDPH) or the peptide GSG (SEQ ID NO: 1). In some aspects, the synthetic peptidoglycan comprises from about 5 to about 40 peptides. In some aspects, the collagen binding peptide comprises an amino acid sequence selected from: i) RRANAALKAGELYKSILY (SEQ ID NO: 2), RLDGNEIKR (SEQ ID NO: 3), AHEEISTTNEGVM (SEQ ID NO: 4), GELYKSILY (SEQ ID NO: 5), NGVFKYRPRYFLYKHAYFYPPLKRFPVQ (SEQ ID NO: 6), CQDSETRTFY (SEQ ID NO: 7), TKKTLRT (SEQ ID NO: 8), GLRSKSKKFRRPDIQYPDATDEDITSHM (SEQ ID NO: 9), SQNPVQP (SEQ ID NO: 10), SYIRIADTNIT (SEQ ID NO: 11), KELNLVYT (SEQ ID NO: 12), GSITTIDVPWNVGC (SEQ ID NO: 13), GSITTIDVPWNV (SEQ ID NO: 14), RRANAALKAGELYKCILY (SEQ ID NO: 15), or GELYKCILY (SEQ ID NO: 16); or ii)

a peptide comprising a sequence with at least about 80% sequence identity to the amino acid sequence of i) and capable of binding to collagen.

In some aspects, the synthetic peptidoglycan is administered to achieve a plasma concentration of collagen binding peptide from 20 μM to 1000 μM proximate the dysfunctional endothelium. In some aspects, the synthetic peptidoglycan is administered to achieve a plasma concentration of collagen binding peptide from 100 μM to 400 μM proximate the dysfunctional endothelium.

Also provided, in one embodiment, is a method for preventing or reducing inflammation at a vascular site in a patient, wherein the site (a) comprises permeated endothelial lining or damaged endothelial cells, and (b) is not undergoing to recovering from a vascular intervention procedure, the method comprising administering to the patient a pharmaceutical composition comprising an effective amount of a synthetic peptidoglycan comprising a glycan having from about 1 to about 80 collagen binding peptide(s) bonded to the glycan.

In some aspects, the vascular intervention procedure comprises a percutaneous coronary intervention (PCI) procedure.

In one embodiment, the disclosure provides a method of inhibiting endothelial cell dysfunction comprising providing a collagen-binding synthetic peptidoglycan; and administering the collagen-binding synthetic peptidoglycan to at least one dysfunctional endothelial cell, wherein the collagen-binding peptidoglycan is administered to inhibit production of selectin molecules on the dysfunctional endothelial cell.

In some aspects, the collagen-binding synthetic peptidoglycan inhibits inflammatory responses in the cell. In some aspects, the collagen-binding synthetic peptidoglycan inhibits platelet binding. In some aspects, the collagen-binding synthetic peptidoglycan inhibits intimal hyperplasia. In some aspects, the collagen-binding synthetic peptidoglycan inhibits chronic inflammation. In some aspects, the collagen-binding synthetic peptidoglycan inhibits multiple system organ failure. In some aspects, the collagen-binding synthetic peptidoglycan treats glaucoma. In some aspects, the collagen-binding synthetic peptidoglycan stimulates endothelial cell proliferation. In some aspects, the collagen-binding synthetic peptidoglycan binds to exposed collagen.

In some aspects, the collagen-binding synthetic peptidoglycan is a compound of formula $P_nG_x$ wherein n is 1 to 50; x is 1 to 60, P is a synthetic peptide of about 5 to about 40 amino acids comprising a sequence of a collagen-binding domain; and G is a glycan.

In some aspects, the collagen-binding synthetic peptidoglycan is a compound of formula $(P_nL)_xG$ wherein n is 1 to 7; x is 1 to 60; P is a synthetic peptide of about 5 to about 40 amino acids comprising a sequence of a collagen-binding domain; L is a linker; and G is a glycan.

In some aspects, the collagen-binding synthetic peptidoglycan is a compound of formula $P(LG_n)_x$ wherein n is 1 to 5; x is 1 to 60; P is a synthetic peptide of about 5 to about 40 amino acids comprising a sequence of a collagen-binding domain; L is a linker; and G is a glycan.

In some aspects, the collagen-binding synthetic peptidoglycan is a compound of formula $P_nG_x$ wherein n is MWG/1000 wherein MWG is the molecular weight of G rounded to the nearest 1 kDa; wherein x is 1 to 10; wherein P is a synthetic peptide of about 5 to about 40 amino acids comprising a sequence of a collagen-binding domain; and wherein G is a glycan.

In some aspects, the collagen-binding synthetic peptidoglycan is a compound of formula $(P_nL)_xG$ wherein n is 1 to 7; wherein x is MWG/1000 wherein MWG is the molecular weight of G rounded to the nearest 1 kDa; wherein P is a synthetic peptide of about 5 to about 40 amino acids comprising a sequence of a collagen-binding domain; wherein L is a linker; and wherein G is a glycan.

In some aspects, the glycan is a glycosaminoglycan or a polysaccharide. In some aspects, the glycan component of the peptidoglycan is selected from the group consisting of alginate, agarose, dextran, chondroitin, dermatan, dermatan sulfate, heparan, heparin, keratin, and hyaluronan. In some aspects, the glycan component of the peptidoglycan is selected from the group consisting of dermatan sulfate, dextran, hyaluronan, and heparin. In some aspects, the glycan is dermatan sulfate.

In some aspects, the peptide component of the peptidoglycan comprises an amino acid sequence selected from the group consisting of RRANAALKAGELYKSILYGC (SEQ ID NO: 17), RLDGNEIKRGC (SEQ ID NO: 18), AHEEISTTNEGVMGC (SEQ ID NO: 19), NGVFKYRPRYFLYKHAYFYPPLKRFPVQGC (SEQ ID NO: 20), CQDSETRTFY (SEQ ID NO: 7), TKKTLRTGC (SEQ ID NO: 21), GLRSKSKKFRRPDIQYPDATDEDITSHMGC (SEQ ID NO: 22), SQNPVQPGC (SEQ ID NO: 23), SYIRIADTNITGC (SEQ ID NO: 24), SYIRIADTNIT (SEQ ID NO: 11), KELNLVYT (SEQ ID NO: 12), KELNLVYTGC (SEQ ID NO: 25), GELYKSILYGC (SEQ ID NO: 26), GSITTIDVPWNV (SEQ ID NO: 14), GCGGELYKSILY (SEQ ID NO: 27), GSITTIDVPWNVGC (SEQ ID NO: 13), and RRANAALKAGELYKSILY (SEQ ID NO: 2).

In some aspects, the peptide component of the peptidoglycan comprises an amino acid sequence of RRANAALKAGELYKSILYGC (SEQ ID NO: 17). In some aspects, the collagen-binding synthetic peptidoglycan is dermatan sulfate with 20 peptides of the sequence RRANAALKAGELYKSILYGC (SEQ ID NO: 17) linked to the glycan (i.e., DS-SILY$_{20}$).

In some aspects, the collagen-binding synthetic peptidoglycan is administered to a patient parenterally. In some aspects, the parenteral administration is through a route selected from the group consisting of intravascular, intravenous, intraarterial, intramuscular, cutaneous, subcutaneous, percutaneous, intradermal, and intraepidermal. In some aspects, the collagen-binding synthetic peptidoglycan is administered parenterally using a needle or a device for infusion. In some aspects, the collagen-binding synthetic peptidoglycan is administered to the patient with a catheter, as a coating on a balloon, through a porous balloon, or as a coating on a stent.

In one embodiment, the present disclosure provides a compound for use in vascular intervention in a patient, said compound comprising a collagen-binding synthetic peptidoglycan wherein the collagen-binding synthetic peptidoglycan binds to a denuded vessel in the patient. In some aspects, the collagen-binding synthetic peptidoglycan inhibits platelet activation. In some aspects, the collagen-binding synthetic peptidoglycan inhibits platelet binding to the denuded vessel. In some aspects, the collagen-binding synthetic peptidoglycan inhibits intimal hyperplasia. In some aspects, the collagen-binding synthetic peptidoglycan inhibits inflammation resulting from denuding of the vessel.

In some aspects, the collagen-binding synthetic peptidoglycan inhibits thrombosis. In some aspects, the collagen-binding synthetic peptidoglycan inhibits vasospasm. In some aspects, the collagen-binding synthetic peptidoglycan stimulates endothelial cell proliferation. In some aspects, the collagen-binding synthetic peptidoglycan binds to exposed collagen on the denuded vessel.

In some aspects, wherein the collagen-binding synthetic peptidoglycan is a compound of formula $P_nG_x$ wherein n is 1 to 50; x is 1 to 60; P is a synthetic peptide of about 5 to about 40 amino acids comprising a sequence of a collagen-binding domain; and G is a glycan.

In some aspects, the collagen-binding synthetic peptidoglycan is a compound of formula $(P_nL)_xG$ wherein n is 1 to 7; x is 1 to 60; P is a synthetic peptide of about 5 to about 40 amino acids comprising a sequence of a collagen-binding domain; L is a linker; and G is a glycan.

In some aspects, the collagen-binding synthetic peptidoglycan is a compound of formula $P(LG_n)_x$ wherein n is 1 to 5; x is 1 to 60; P is a synthetic peptide of about 5 to about 40 amino acids comprising a sequence of a collagen-binding domain; L is a linker; and G is a glycan.

In some aspects, the collagen-binding synthetic peptidoglycan is a compound of formula $P_nG_x$ wherein n is MWG/1000 wherein MWG is the molecular weight of G rounded to the nearest 1 kDa; wherein x is 1 to 60; wherein P is a synthetic peptide of about 5 to about 40 amino acids comprising a sequence of a collagen-binding domain; and wherein G is a glycan.

In some aspects, the collagen-binding synthetic peptidoglycan is a compound of formula $(P_nL)_xG$ wherein n is 1 to 7; wherein x is MWG/1000 wherein MWG is the molecular weight of G rounded to the nearest 1 kDa; wherein P is a synthetic peptide of about 5 to about 40 amino acids comprising a sequence of a collagen-binding domain; wherein L is a linker; and wherein G is a glycan.

In some aspects, the glycan is a glycosaminoglycan or a polysaccharide.

In some aspects, the glycan component of the peptidoglycan is selected from the group consisting of alginate, agarose, dextran, chondroitin, dermatan, dermatan sulfate, heparan, heparin, keratin, and hyaluronan. In some aspects, the glycan component of the peptidoglycan is selected from the group consisting of dermatan sulfate, dextran, hyaluronan, and heparin. In some aspects, the glycan is dermatan sulfate.

In some aspects, the peptide component of the peptidoglycan comprises an amino acid sequence selected from the group consisting of RRANAALKAGELYKSILYGC (SEQ ID NO: 17), RLDGNEIKRGC (SEQ ID NO: AHEEISTTNEGVMGC (SEQ ID NO: 19), NGVFKYRPRYFLYKHAYFYPPLKRFPVQGC (SEQ ID NO: 20), CQDSETRTFY (SEQ ID NO: 7), TKKTLRTGC (SEQ ID NO: 21), GLRSKSKKFRRPDIQYPDATDEDITSHMGC (SEQ ID NO: 22), SQNPVQPGC (SEQ ID NO: 23), SYIRIADTNITGC (SEQ ID NO: 24), SYIRIADTNIT (SEQ ID NO: 11), KELNLVYT (SEQ ID NO: 12), KELNLVYTGC (SEQ ID NO: 25), GELYKSILYGC (SEQ ID NO: 26), GSITTIDVPWNV (SEQ ID NO: 14), GCGGELYKSILY (SEQ ID NO: 27), GSITTIDVPWNVGC (SEQ ID NO: 13), and RRANAALKAGELYKSILY (SEQ ID NO: 2). In some aspects, the peptide component of the peptidoglycan comprises an amino acid sequence of RRANAALKAGELYKSILYGC (SEQ ID NO: 17). In some aspects, the collagen-binding synthetic peptidoglycan is dermatan sulfate with the sequence RRANAALKAGELYKSILYGC (SEQ ID NO: 17) linked to the glycan (i.e., DS-SILY).

In some aspects, the collagen-binding synthetic peptidoglycan is administered to the patient parenterally. In some aspects, the parenteral administration is through a route selected from the group consisting of intravascular, intravenous, intraarterial, intramuscular, cutaneous, subcutaneous, percutaneous, intradermal, and intraepidermal. In some aspects, the collagen-binding synthetic peptidoglycan is administered parenterally using a needle or a device for infusion. In some aspects, the collagen-binding synthetic peptidoglycan is administered to the patient with a catheter, as a coating on a balloon, through a porous balloon, or as a coating on a stent.

Also provided, in one embodiment, is a kit comprising a collagen-binding synthetic peptidoglycan; and a component selected from the group consisting of a catheter, a stent, a balloon, and a combination thereof. In some aspects, the collagen-binding synthetic peptidoglycan is a compound of formula $P_nG_x$ wherein n is 1 to 60; x is 1 to 60 P is a synthetic peptide of about 5 to about 40 amino acids comprising a sequence of a collagen-binding domain; and G is a glycan.

In some aspects, the collagen-binding synthetic peptidoglycan is a compound of formula $(P_nL)_xG$ wherein n is 1 to 7; x is 1 to 60; P is a synthetic peptide of about 5 to about 40 amino acids comprising a sequence of a collagen-binding domain; L is a linker; and G is a glycan.

In some aspects, the collagen-binding synthetic peptidoglycan is a compound of formula $P(LG_n)_x$ wherein n is 1 to 5; x is 1 to 60; P is a synthetic peptide of about 5 to about 40 amino acids comprising a sequence of a collagen-binding domain; L is a linker; and G is a glycan.

In some aspects, the collagen-binding synthetic peptidoglycan is a compound of formula $P_nG_x$ wherein n is MWG/1000 wherein MWG is the molecular weight of G rounded to the nearest 1 kDa; wherein x is 1 to 60; wherein P is a synthetic peptide of about 5 to about 40 amino acids comprising a sequence of a collagen-binding domain; and wherein G is a glycan.

In some aspects, the collagen-binding synthetic peptidoglycan is a compound of formula $(P_nL)_xG$ wherein n is 1 to 7; wherein x is MWG/1000 wherein MWG is the molecular weight of G rounded to the nearest 1 kDa; wherein P is a synthetic peptide of about 5 to about 40 amino acids comprising a sequence of a collagen-binding domain; wherein L is a linker; and wherein G is a glycan.

In some aspects, the glycan is a glycosaminoglycan or a polysaccharide. In some aspects, the glycan component of the peptidoglycan is selected from the group consisting of alginate, agarose, dextran, chondroitin, dermatan, dermatan sulfate, heparan, heparin, keratin, and hyaluronan.

In some aspects, the glycan component of the peptidoglycan is selected from the group consisting of dermatan sulfate, dextran, hyaluronan, and heparin. In some aspects, the glycan is dermatan sulfate.

In some aspects, the peptide component of the peptidoglycan comprises an amino acid sequence selected from the group consisting of RRANAALKAGELYKSILYGC (SEQ ID NO: 17), RLDGNEIKRGC (SEQ ID NO: 18), AHEEISTTNEGVMGC (SEQ ID NO: 19), NGVFKYRPRYFLYKHAYFYPPLKRFPVQGC (SEQ ID NO: 20), CQDSETRTFY (SEQ ID NO: 7), TKKTLRTGC (SEQ ID NO: 21), GLRSKSKKFRRPDIQYPDATDEDITSHMGC (SEQ ID NO: 22), SQNPVQPGC (SEQ ID NO: 23), SYIRIADTNITGC (SEQ ID NO: 24), SYIRIADTNIT (SEQ ID NO: 11), KELNLVYT (SEQ ID NO: 12), KELNLVYTGC (SEQ ID NO: 25), GELYKSILYGC (SEQ ID NO: 26), GSITTIDVPWNV (SEQ ID NO: 14), GCGGELYKSILY (SEQ ID NO: 27), GSITTIDVPWNVGC (SEQ ID NO: 13), and RRANAALKAGELYKSILY (SEQ ID NO: 2). In some aspects, the peptide component of the peptidoglycan comprises an amino acid sequence of RRANAALKAGELYKSILYGC (SEQ ID NO: 17). In some aspects, the collagen-binding synthetic peptidoglycan is DS-SILY$_{20}$.

In another embodiment, the present disclosure provides a compound the formula $P_nG_x$ wherein n is 10 to 25; x is 1 to 60, P is a synthetic peptide of about 5 to about 40 amino acids comprising a sequence of a collagen-binding domain; and G is a glycan. In some aspects, n is 15 to 25. In some aspects, n is 15 to 20. In some aspects, n is about 18. In some aspects, the formula is $P_{18}G_{1-10}$. In some aspects, the formula is $P_{18}G_1$. In some aspects, the compound is dermatan sulfate with 18 peptides of the sequence RRANAALKAGELYKSILYGC (SEQ ID NO: 17) linked to the glycan (i.e., DS-SILY$_{18}$).

In one aspect of any compound, method or kit of the present disclosure, the synthetic peptidoglycan inhibits blood cell binding to the denuded vessel. In some aspects, the peptide component of the peptidoglycan comprises or is an amino acid sequence selected from the group consisting of RRANAALKAGELYKSILY (SEQ ID NO: 2), RLDGNEIKR (SEQ ID NO: 3), AHEEISTTNEGVM (SEQ ID NO: 4), NGVFKYRPRYFLYKHAYFYPPLKRFPVQ (SEQ ID NO: 6), CQDSETRTFY (SEQ ID NO: 7), TKKTLRT (SEQ ID NO: 8), GLRSKSKKFRRPDIQYPDATDEDITSHM (SEQ ID NO: 9), SQNPVQP (SEQ ID NO: 10), SYIRIADTNIT (SEQ ID NO: 11), KELNLVYT (SEQ ID NO: 12), GELYKSILY (SEQ ID NO: 5), GSITTIDVPWNV (SEQ ID NO: 14), GCGGELYKSILY (SEQ ID NO: 27) and GSITTIDVPWNV (SEQ ID NO: 14).

DETAILED DESCRIPTION

1. Definitions

Figure 1A:
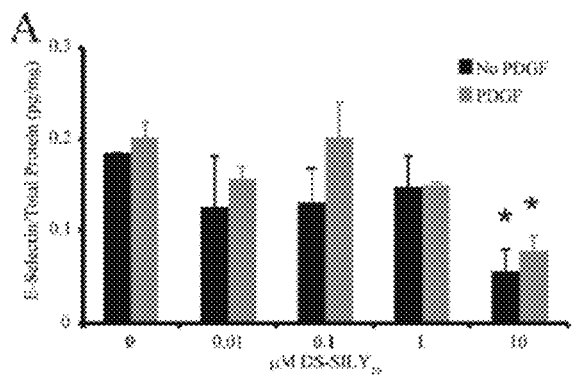
FIGS. 1A and 1B illustrate the production of E-selectin and P-selectin, respectively, in human aortic endothelial cells (HAECs) treated with DS-SILY$_{20}$ with (grey bars) and without PDGF (black bars), where E-selectin and P-selectin produced by cultured HAECs was measured twenty-four hours post-treatment following cell lysis.

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the internal surface of a vein.

As used herein, the term "formulated" or "formulation" refers to the process in which different chemical substances, including one or more pharmaceutically active ingredients, are combined to produce a dosage form. In certain embodiments, two or more pharmaceutically active ingredients can be coformulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "delivery" refers to approaches, formulations, technologies, and systems for transporting a pharmaceutical composition in the body as needed to safely achieve its desired therapeutic effect. In some embodiments, an effective amount of the composition is formulated for delivery into the blood vessels of a patient.

2. Methods

The present disclosure, in one embodiment, provides compositions and methods for treating a patient suffering from a disease associated with endothelial dysfunction. The compositions, in some embodiments, include a synthetic collagen binding peptidoglycan of the present disclosure.

It is discovered herein that collagen binding peptidoglycans can reduce the inflammatory impact of endothelial dysfunction or injury, in both acute and chronic diseases. It is contemplated that such peptidoglycans inhibit or reduce platelet binding to the dysfunctional endothelium and thus reduce platelet-mediated inflammation. Inflammation can be activated through platelet processes such as platelet-platelet binding, platelet-leukocyte binding, facilitation of leukocyte diapedesis, or simply release from platelets of local and regional cytokines.

Further, it is discovered that collagen binding peptidoglycans decrease pro-inflammatory cytokine secretion and the expression of E-selectin and P-selectin in the exposed endothelial cells. Moreover, these peptidoglycans can increase endothelial cell proliferation and migration, attenuate IL-6 secretion and the production of vascular injury markers, even in the presence of platelet-derived growth factor (PDGF). It is contemplated that some or all of these effects brought about by the administration of collagen binding peptidoglycans contribute to the reduction of inflammatory at dysfunctional endothelium.

Also provided, in some embodiments, is a method for preventing or reducing inflammation at a vascular site suffering from endothelial dysfunction. The method entails administering to the site a pharmaceutical composition that includes a synthetic collagen binding peptidoglycan of the present disclosure.

As described herein, the collagen-binding peptidoglycans can bind collagen with high affinity, where they remain bound during blood flow to prevent platelet binding to exposed collagen of the denuded endothelium and, consequently, to prevent platelet activation, thrombosis, inflammation resulting from denuding the endothelium, intimal hyperplasia, and vasospasm. Therefore, these collagen-binding peptidoglycans can inhibit inflammatory responses by inhibiting the production of selectins or ICAMs/VCAMs in dysfunctional endothelial cells. The collagen-binding proteoglycans of the present can also stimulate endothelial cell proliferation and can bind to collagen, thereby inhibiting the production of selectins on exposed endothelial cells.

The term "endothelial dysfunction" is also referred to as "endothelial cell (EC) dysfunction," "dysfunctional endothelium," or "dysfunctional endothelial cells." Endothelial dysfunction can be determined with unmasking or exposure of ICAM and VCAM receptors or selectin receptors on the cell surface of an endothelial cell. P-selectin and E-selectin are examples of selectin receptors exposed which are transiently expressed on the cell surface due to damage and inflammation, and chronically expressed in dysfunctional endothelium.

In some embodiments, endothelial dysfunction is characterized with permeated endothelial lining or damaged endothelial cells. In some embodiments, the endothelial dysfunction is characterized by loss of glycocalyx. In some embodiments, the endothelial dysfunction is characterized by a selectin protein expressed on the surface of endothelial cells and exposed to circulation. In some embodiments, the site suffers from inflammation.

In one aspect, the vascular site is not denuded by physical means, and is not undergoing to recovering from a vascular intervention procedure. Non-limiting examples of vascular intervention procedures include percutaneous coronary intervention (PCI).

A "disease associated with endothelial dysfunction," as used herein, refers to a human disease or condition that is at least in part caused by endothelial dysfunction or that induces endothelial dysfunction. Treating a disease associated with endothelial dysfunction, accordingly, refers to the treatment of the disease, recovering the dysfunctional endothelium, or preventing or ameliorating conditions or symptoms arising from dysfunctional endothelium, such as inflammation, intimal hyperplasia, and thrombosis.

As disclosed, in some embodiments, the collagen-binding peptidoglycans can inhibit dysfunctional endothelial cells to treat, inhibit, or attenuate inflammatory diseases. Dysfunctional endothelial cells are associated with inflammation and other inflammatory diseases as evidenced by Ley, "The role of selectins in inflammation and disease", Vol. 9, Elsevier Science, (2003). Examples of other inflammatory diseases and autoimmune diseases include atherosclerosis, coronary artery disease, diabetes mellitus, hypertension, hypercholesterolemia, rheumatoid arthritis, systemic lupus erythematosus, glaucoma, uremia, sepsis, and organ failure.

By inhibiting the production of selectin receptors and masking VCAM/ICAM receptors, the collagen-binding peptidoglycans can be used to treat patients suffering from these transient or chronic diseases. Evidence of selectin inhibition associated with inhibiting or attenuating these diseases is supported in Ridings et al., "A dual-binding antibody to E- and L-selectin attenuates sepsis-induced lung injury", Vol. 152, American Journal of Respiratory and Critical Care Medicine, (1995), Weyrich et al., "In Vivo Neutralization of P-Selectin Protects Feline Heart and Endothelium in Myocardial Ischemia and Reperfusion Injury", Vol. 91, The American Society for Clinical Investigation, (1993), each of which is incorporated herein by reference. It is known in the art that some cancers are also associated with inflammation and chronic inflammation, and therefore the collagen-binding peptidoglycans can be used to treat, inhibit, or attenuate neoplastic cell growth.

In an illustrative embodiment, these collagen-binding proteoglycans of the present disclosure can be used in vascular intervention procedures including, for example, to prevent any one or a combination of platelet binding to exposed collagen of the denuded endothelium, platelet activation, thrombosis, inflammation resulting from denuding the endothelium, intimal hyperplasia, and vasospasm. The collagen-binding peptidoglycans described herein can also inhibit inflammatory responses by inhibiting the production of selectins or ICAMs/VCAMs in dysfunctional endothelial cells.

It is contemplated that the synthetic peptidoglycans can be tailored with respect to the peptide identity, the number of peptides attached to the glycosaminoglycan (GAG) backbone, and the GAG backbone identity for optimized treatment depending on the disease to be treated and location of the affected dysfunctional endothelium. Thus, a number of molecular design parameters can be engineered to optimize the target effect.

In one embodiment, the molecule configuration consists of a dermatan sulfate (DS) GAG backbone with attached collagen binding peptide(s). DS may be useful because of its ability to promote epithelial cell migration and proliferation.

It is contemplated that other variants of GAG-peptide provided herein are also capable of inhibiting inflammation at dysfunctional endothelium. In one embodiment the synthetic peptidoglycans include a collagen binding peptide such as RRANAALKAGELYKSILY (SEQ ID NO: 2), referred to as "SILY".

In another embodiment, the synthetic peptidoglycan includes collagen binding peptide(s) (SILY) conjugated to GAG backbones comprising heparin (Hep-SILY), dermatan sulfate (DS-SILY), or dextran (Dex-SILY) (see, e.g., U.S. Pat. No. 8,846,003 and Publication 2013/0190246).

3. Synthetic Peptidoglycans

In one embodiment, the synthetic peptidoglycan comprises a glycan having from about 1 to about 80 collagen binding peptide(s) bonded to the glycan.

As used herein, the term "synthetic peptidoglycan" refers to a synthetic conjugate that comprises a glycan and one or more synthetic peptides covalently bonded thereto. The glycan portion can be made synthetically or derived from animal sources. The synthetic peptides can be covalently bonded directly to the glycan or via a linker. For methods of conjugating collagen binding peptides to glycans, see, e.g., US 2013/0190246, US 2012/0100106, and US 2011/0020298, the disclosures of which are incorporated herein by reference in their entirety. In some embodiments, the term synthetic peptidoglycan includes proteoglycans. In one embodiment, the molecular weight range for the synthetic peptidoglycan is from about 13 kDA to about 1.2 MDa, or from about 500 kDa to about 1 MDa, or from about 20 kDa to about 90 kDa, or from about 10 kDa to about 70 kDa.

As used herein, the term "glycan" refers to a compound having a large number of monosaccharides linked glycosidically. In certain embodiments, the glycan is a glycosaminoglycan (GAG), which comprise 2-aminosugars linked in an alternating fashion with uronic acids, and include polymers such as heparin, heparan sulfate, chondroitin, keratin, and dermatan. Accordingly, non-limiting examples of glycans which can be used in the embodiments described herein include alginate, agarose, dextran (Dex), chondroitin, chondroitin sulfate (CS), dermatan, dermatan sulfate (DS), heparan sulfate, heparin (Hep), keratin, keratan sulfate, and hyaluronic acid (HA). In one embodiment the molecular weight of the glycan is a key parameter in its biological function. In another embodiment the molecular weight of the glycan is varied to tailor the effects of the synthetic peptidoglycan mimic (see e.g., Radek, K. A., et al., Wound Repair Regen., 2009, 17: 118-126; and Taylor, K. R., et al., J. Biol. Chem., 2005, 280:5300-5306). In another embodiment, the glycan molecular weight is about 46 kDa. In another embodiment, the glycan is degraded by oxidation and alkaline elimination (see e.g., Fransson, L. A., et al., Eur. J. Biochem., 1980, 106:59-69) to afford degraded glycan having a lower molecular weight (e.g., from about 10 kDa to about 50 kDa). In some embodiments, the glycan is unmodified.

In one embodiment, the GAG is dermatan sulfate (DS). The biological functions of DS are extensive, and include the binding and activation of growth factors FGF-2, FGF-7, and FGF-10, which promote endothelial cell and keratinocyte proliferation and migration. In one embodiment, the DS molecular weight is about 46 kDa. In another embodiment, the DS is degraded by oxidation and alkaline elimination (see e.g., Fransson, L. A., et al., Eur. J. Biochem., 1980, 106:59-69) to afford degraded DS having a low molecular weight (e.g., 10 kDa). In some embodiments, the weight range of the DS is from about 10 kDa to about 70 kDa.

As used herein, the terms "bonded" and "covalently bonded" can be used interchangeably, and refer to the sharing of one or more pairs of electrons by two atoms. In one embodiment, the peptide is bonded to the glycan. In one embodiment the peptide is covalently bonded to the glycan, with or without a linker. In one embodiment the peptide is covalently bonded to the glycan via a linker. In one embodiment the peptide is directly bonded to the glycan.

In one embodiment, the synthetic peptidoglycans of the disclosure bind, either directly or indirectly to collagen. The terms "binding" or "bind" as used herein are meant to include interactions between molecules that may be detected using, for example, a hybridization assay, surface plasmon resonance, ELISA, competitive binding assays, isothermal titration calorimetry, phage display, affinity chromatography, rheology or immunohistochemistry. The terms are also meant to include "binding" interactions between molecules. Binding may be "direct" or "indirect". "Direct" binding comprises direct physical contact between molecules. "Indirect" binding between molecules comprises the molecules having direct physical contact with one or more molecules simultaneously. This binding can result in the formation of a "complex" comprising the interacting molecules. A "complex" refers to the binding of two or more molecules held together by covalent or non-covalent bonds, interactions or forces.

As used herein, the term "collagen binding peptide" refers to a peptide, which can be synthetic, comprising a "collagen binding unit." The term "collage binding unit" refers to an amino acid sequence capable of "collagen binding," an interaction with collagen that could include hydrophobic, ionic (charge), and/or Van der Waals interactions, such that the compound binds or interacts favorably with collagen. This binding (or interaction) is intended to be differentiated from covalent bonds and nonspecific interactions with common functional groups, such that the collagen binding unit would interact with any species containing that functional group to which the collagen binding unit binds on the collagen. Collagen binding units can be tested and assessed for binding to collagen using any method known in the art. See, e.g., Li, Y., et al., Current Opinion in Chemical Biology, 2013, 17: 968-975, Helmes, B. A., et al., J. Am. Chem. Soc. 2009, 131, 11683-11685, and Petsalaki, E., et al., PLoS Comput Biol, 2009, 5(3): e1000335. In one embodiment, the collagen binding peptide, or the collagen binding unit of the peptide, binds to collagen with a dissociation constant ($K_d$) of less than about 1 mM, or less than about 900 µM, or less than about 800 µM, or less than about 700 µM, or less than about 600 µM, or less than about 500 µM, or less than about 400 µM, or less than about 300 µM, or less than about 200 µM, or less than about 100 µM.

The collagen binding unit can have amino acid homology with a portion of a protein normally or not normally involved in collagen fibrillogenesis. In some embodiments, these units have homology or sequence identity to the amino acid sequence of a small leucine-rich proteoglycan, a platelet receptor sequence, or a protein that regulates collagen fibrillogenesis. In various embodiments, the collagen binding unit or the collagen binding peptide that includes the unit comprises an amino acid sequence selected from RRANAALKAGELYKSILY (SEQ ID NO: 2), GELYKSILY (SEQ ID NO: 5), RRANAALKAGELYKCILY (SEQ ID NO: 15), GELYKCILY (SEQ ID NO: 16), RLDGNEIKR (SEQ ID NO: 3), AHEEISTTNEGVM (SEQ ID NO: 4), NGVFKYRPRYFLYKHAYFYPPLKRFPVQ (SEQ ID NO: 6), CQDSETRTFY (SEQ ID NO: 7), TKKTLRT (SEQ ID NO: 8), GLRSKSKKFRRPDIQYPDATDEDITSHM (SEQ ID NO: 9), SQNPVQP (SEQ ID NO: 10), SYIRIADTNIT (SEQ ID NO: 11), KELNLVYT (SEQ ID NO: 12), or GSITTIDVPWNV (SEQ ID NO: 14); or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

In certain embodiments, the collagen binding unit or the collagen binding peptide that includes the unit comprises an amino acid sequence that has at least about 80%, or at least about 83%, or at least about 85%, or at least about 90%, or at least about 95%, or at least about 98%, or at least about 100% sequence identity with the collagen-binding domain(s) of the von Willebrand factor (vWF) or a platelet collagen receptor as described in Chiang, T. M., et al. J. Biol. Chem., 2002, 277: 34896-34901, Huizinga, E. G. et al., Structure, 1997, 5: 1147-1156, Romijn, R. A., et al., J. Biol. Chem., 2003, 278: 15035-15039, and Chiang, et al., Cardio. & Haemato. Disorders-Drug Targets, 2007, 7: 71-75, each incorporated herein by reference. A non-limiting example is WREPSFCALS (SEQ ID NO: 28), derived from vWF.

Various methods for screening amino acid sequences for collagen-binding affinity (or a collagen-binding domain) are routine in the art. Other amino acid sequences shown to have collagen-binding affinity (or a collagen-binding domain) which can be used in the peptidoglycans and methods disclosed herein include but are not limited to, βAWHCTTKFPHHYCLYBip (SEQ ID NO: 29), βAHKCPWHLYTTHYCFTBip (SEQ ID NO: 30), βAHKCPWHLYTHYCFT (SEQ ID NO: 31), etc., where Bip is biphenylalanine and βA is beta-alanine (see, Abd-Elgaliel, W. R., et al., Biopolymers, 2013, 100(2), 167-173), GROGER (SEQ ID NO: 32), GMOGER (SEQ ID NO: 33), GLOGEN (SEQ ID NO: 34), GLOGER (SEQ ID NO: 35), GLKGEN (SEQ ID NO: 36), GFOGERGVEGPOGPA (SEQ ID NO: 37), etc., where O is 4-hydroxyproline (see, Raynal, N., et al., J. Biol. Chem., 2006, 281(7), 3821-3831), HVWMQAPGGGK (SEQ ID NO: 38) (see, Helms, B. A., et al., J. Am. Chem. Soc. 2009, 131, 11683-11685), WREPSFCALS (SEQ ID NO: 28) (see, Takagi, J., et al., Biochemistry, 1992, 31, 8530-8534), WYRGRL (SEQ ID NO: 39), etc. (see, Rothenfluh D. A., et al., Nat Mater. 2008, 7(3), 248-54), WTCSGDEYTWHC (SEQ ID NO: 40), WTCVGDHKTWKC (SEQ ID NO: 41), QWHCTTRFPHHYCLYG (SEQ ID NO: 42), etc. (see, U.S. 2007/0293656), STWTWNGSAWTWNEGGK (SEQ ID NO: 43), STWTWNGTNWTRNDGGK (SEQ ID NO: 44), etc. (see, WO/2014/059530), CVWLWEQC (SEQ ID NO: 45) (see, Depraetere H., et al., Blood. 1998, 92, 4207-4211; and Duncan R., Nat Rev Drug Discov, 2003, 2(5), 347-360), CMTSPWRC (SEQ ID NO: 46), etc. (see, Vanhoorelbeke, K., et al., J. Biol. Chem., 2003, 278, 37815-37821), CPGRVMHGLHLGDDEGPC (SEQ ID NO: 47) (see, Muzzard, J., et al., PLoS one. 4 (e 5585) 1-10), KLWLLPK (SEQ ID NO: 48) (see, Chan, J. M., et al., Proc Natl Acad Sci U.S.A., 2010, 107, 2213-2218), and CQDSETRTFY (SEQ ID NO: 7), etc. (see, U.S. 2013/0243700), wherein each is hereby incorporated by reference in its entirety.

As used herein, the term "sequence identity" refers to a level of amino acid residue or nucleotide identity between two peptides or between two nucleic acid molecules. When a position in the compared sequence is occupied by the same base or amino acid, then the molecules are identical at that position. A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure. Likewise, the present disclosure also includes sequences that have one, two, three, four, or five substitution, deletion or addition of amino acid residues or nucleotides as compared to the reference sequences.

In any of the embodiments described herein, any one or more of the synthetic peptides (e.g., the collagen binding peptide) may have a spacer sequence comprising from one to about five amino acids. It is contemplated that any amino acid, natural or unnatural, can be used in the spacer sequence, provided that the spacer sequence does not significantly interfere with the intended binding of the peptide. Exemplary spacers include, but are not limited to, short sequences comprising from one to five glycine units (e.g., G, GG, GGG, GGGG (SEQ ID NO: 54 or GGGGG (SEQ ID NO: 55)), optionally comprising cysteine (e.g., GC, GCG, GSGC (SEQ ID NO: 56), or GGC) and/or serine (e.g., GSG (SEQ ID NO: 1), or GSGSG (SEQ ID NO: 57)), or from one to five arginine units (e.g., R, RR, RRR, etc.). The spacer can also comprise non-amino acid moieties, such as polyethylene glycol (PEG), 6-aminohexanoic acid, or combinations thereof, with or without an amino acid spacer. The spacer can be attached to either the C-terminus or the N-terminus of the peptide to provide a point of attachment for a glycan or a glycan-linker conjugate.

The glycan (e.g., glycosaminoglycan, abbreviated GAG, or polysaccharide) attached to the synthetic peptide can be selected from the group consisting alginate, agarose, dextran, chondroitin, dermatan, dermatan sulfate, heparan, heparin, keratin, and hyaluronan. In one embodiment, the glycan is selected from the group consisting of dermatan sulfate, dextran, and heparin. In another illustrative embodiment the glycan is dermatan sulfate. The collagen-binding synthetic proteoglycan in any of these embodiments can be used to inhibit platelet binding to exposed collagen of the denuded endothelium, platelet activation, thrombosis, inflammation resulting from dysfunction endothelial cells, intimal hyperplasia, and vasospasm during a vascular intervention procedure. The collagen-binding synthetic peptidoglycans described herein can also stimulate endothelial cell proliferation and can bind to collagen, thereby inhibiting the production of selectins on exposed endothelial cells.

In one aspect the disclosure is used to inhibit dysfunctional endothelial cells to treat, inhibit, or attenuate inflammatory diseases. Dysfunctional endothelial cells are associated with inflammation and other inflammatory diseases as evidenced by Ley, "The role of selectins in inflammation and disease", Vol. 9, Elsevier Science, (2003). Examples of other inflammatory diseases and autoimmune diseases include atherosclerosis, coronary artery disease, diabetes mellitus, hypertension, hypercholesterolemia, rheumatoid arthritis, systemic lupus erythematosus, glaucoma, uremia, sepsis, and organ failure. By inhibiting the production of selectin receptors and masking VCAM/ICAM receptors, the invention may be used to treat patients suffering from these transient or chronic diseases. Evidence of selectin inhibition associated with inhibiting or attenuating these diseases is supported in Ridings et al., "A dual-binding antibody to E- and L-selectin attenuates sepsis-induced lung injury", Vol. 152, American Journal of Respiratory and Critical Care Medicine, (1995), Weyrich et al., "In Vivo Neutralization of P-Selectin Protects Feline Heart and Endothelium in Myocardial Ischemia and Reperfusion Injury", Vol. 91, The American Society for Clinical Investigation, (1993), each of which is incorporated herein by reference. It is well known in the art that some cancers are also associated with inflammation and chronic inflammation, and therefore the invention may be used to treat, inhibit, or attenuate neoplastic cell growth.

In one illustrative aspect, the collagen-binding synthetic peptidoglycan may be sterilized. As used herein "sterilization" or "sterilize" or "sterilized" means disinfecting the collagen-binding synthetic peptidoglycans by removing unwanted contaminants including, but not limited to, endotoxins and infectious agents.

In various illustrative embodiments, the collagen-binding synthetic peptidoglycan can be disinfected and/or sterilized using conventional sterilization techniques including propylene oxide or ethylene oxide treatment, gas plasma sterilization, gamma radiation, electron beam, and/or sterilization with a peracid, such as peracetic acid. Sterilization techniques which do not adversely affect the structure and biotropic properties of the collagen-binding synthetic peptidoglycan can be used. Illustrative sterilization techniques are exposing the collagen-binding synthetic peptidoglycan to peracetic acid, 1-4 Mrads gamma irradiation (or 1-2.5 Mrads of gamma irradiation), ethylene oxide treatment, sterile filtration, or gas plasma sterilization. In one embodiment, the collagen-binding synthetic peptidoglycan can be subjected to one or more sterilization processes. Another illustrative embodiment is subjecting the collagen-binding synthetic proteoglycan to sterile filtration. The collagen-binding synthetic peptidoglycan may be wrapped in any type of container including a plastic wrap or a foil wrap, and may be further sterilized.

In various embodiments described herein, the collagen-binding synthetic peptidoglycans can be combined with minerals, amino acids, sugars, peptides, proteins, vitamins (such as ascorbic acid), or laminin, collagen, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic.

In various embodiments described herein, a kit is provided comprising one or more collagen-binding synthetic peptidoglycans. The kit itself can be within a container of any type, and the kit can contain instructions for use of the components of the kit. In one embodiment, the kit comprises a vessel, vial, container, bag, or wrap, for example, containing a collagen-binding synthetic peptidoglycan. In another embodiment, the kit comprises a vessel or separate vessels (e.g., a vial, container, bag, or wrap), each containing one of the following components: a buffer and one or more types of collagen-binding synthetic peptidoglycans. In any of these embodiments, the kits can further comprise a buffer, a sterilizing or disinfecting agent, non-collagenous proteins or polysaccharides, and/or instructional materials describing methods for using the kit reagents. In any of these embodiments, the kit can contain a component selected from the group consisting of a catheter, a stent, a balloon, and a combination thereof. The collagen-binding synthetic peptidoglycan can be lyophilized, for example, in a buffer or in water.

In any of the embodiments herein described, the collagen-binding synthetic peptidoglycan can be a compound of any of the following formulas A) $P_nG_x$ wherein n is 1 to 50;
 wherein x is 1 to 10;
 wherein P is a synthetic peptide of about 5 to about 40 amino acids comprising a sequence of a collagen-binding domain; and
 wherein G is a glycan.
OR
B) $(P_nL)_xG$ wherein n is 1 to 7;
 wherein x is 1 to 10;
 wherein P is a synthetic peptide of about 5 to about 40 amino acids comprising a sequence of a collagen-binding domain;
 wherein L is a linker; and
 wherein G is a glycan.
OR
C) $P(LG_n)_x$ wherein n is 1 to 5;
 wherein x is 1 to 10;
 wherein P is a synthetic peptide of about 5 to about 40 amino acids comprising a sequence of a collagen-binding domain;
 wherein L is a linker; and
 wherein G is a glycan.

In any of the above described formulas, n can be 1 to 5, 1 to 10, 1 to 15, 1 to 20, 1 to 25, 1 to 30, 1 to 35, 1 to 40, 1 to 45, 1 to 50, 10 to 25, 15 to 25, 15 to 20, 18, or about 20. In alternative embodiments, the collagen-binding synthetic peptidoglycan can be a compound of any of the following formulas A) $P_nG_x$ wherein n is MWG/1000;
   wherein MWG is the molecular weight of G rounded to the nearest 1 kDa;
   wherein x is 1 to 10;
   wherein P is a synthetic peptide of about 5 to about 40 amino acids comprising a sequence of a collagen-binding domain; and
   wherein G is a glycan.
OR
B) $(P_nL)_xG$ wherein n is 1 to 7;
   wherein x is MWG/1000;
   wherein MWG is the molecular weight of G rounded to the nearest 1 kDa;
   wherein P is a synthetic peptide of about 5 to about 40 amino acids comprising a sequence of a collagen-binding domain;
   wherein L is a linker; and
   wherein G is a glycan.

In various embodiments described herein, a collagen-binding synthetic peptidoglycan comprising a synthetic peptide of about 5 to about 40 amino acids with amino acid sequence homology to a collagen binding peptide (e.g. a portion of an amino acid sequence of a collagen binding protein or proteoglycan) conjugated to alginate, agarose, dextran, chondroitin, dermatan, dermatan sulfate, heparan, heparin, keratin, and hyaluronan. In one embodiment, the glycan is selected from the group consisting of dermatan sulfate, dextran, hyaluronan, and heparin. In another illustrative embodiment the glycan is dermatan sulfate. In yet another embodiment, the glycan is dermatan sulfate with 20 peptides of the sequence RRANAALKAGELYKSILYGC (SEQ ID NO: 17) linked to the glycan (i.e., DS-SILY$_{20}$). In yet another embodiment, the glycan is dermatan sulfate with 20 peptides comprising the sequence RRANAALKAGE-LYKSILY (SEQ ID NO: 2) linked to the glycan. The collagen-binding synthetic proteoglycan in any of these embodiments can be used to inhibit platelet binding to exposed collagen of the denuded endothelium, inhibit binding of other cells in blood to exposed collagen of the denuded epithelium, inhibit platelet activation, inhibit thrombosis, inhibit inflammation resulting from dysfunction endothelial cells, inhibit intimal hyperplasia, and/or inhibit vasospasm. The collagen-binding synthetic peptidoglycans described herein can also stimulate endothelial cell proliferation and can also inhibit inflammatory responses by inhibiting the production of selectins or ICAMs/VCAMs in dysfunctional endothelial cells. In any of these embodiments, these aforementioned effects can occur during a vascular intervention procedure, such as a catheter-based procedure. In any of these embodiments, any of the above-described compounds can be used.

In another illustrative embodiment, any of the compounds described above as embodiments A, B, or C or alternative embodiments A or B can inhibit platelet binding to exposed collagen of the denuded endothelium, platelet activation, thrombosis, inflammation resulting from denuding the endothelium, intimal hyperplasia, and/or vasospasm, or can stimulate endothelial cell proliferation or inhibit inflammatory responses by inhibiting the production of selectins or ICAMs/VCAMs in dysfunctional endothelial cells. In another illustrative embodiment, during a vascular intervention procedure, any of the compounds described above as embodiments A, B, or C or alternative embodiments A or B, can inhibit platelet binding to exposed collagen of the denuded endothelium, platelet activation, thrombosis, inflammation resulting from denuding the endothelium, intimal hyperplasia, and/or vasospasm, or can stimulate endothelial cell proliferation or inhibit inflammatory responses by inhibiting the production of selectins or ICAMs/VCAMs in dysfunctional endothelial cells.

In another illustrative embodiment, DS-SILY$_{18}$ can inhibit platelet binding to exposed collagen of the denuded endothelium, platelet activation, thrombosis, inflammation resulting from denuding the endothelium, intimal hyperplasia, and/or vasospasm, or can stimulate endothelial cell proliferation or can bind to collagen in a denuded vessel. In another illustrative embodiment, during a vascular intervention procedure, DS-SILY$_{18}$ can inhibit platelet binding to exposed collagen of the denuded endothelium, platelet activation, thrombosis, inflammation resulting from denuding the endothelium, intimal hyperplasia, and/or vasospasm, or can stimulate endothelial cell proliferation or inhibit inflammatory responses by inhibiting the production of selectins in dysfunctional endothelial cells. In another illustrative embodiment, during a vascular intervention procedure, DS-SILY$_{18}$ can inhibit platelet binding to exposed collagen of the denuded endothelium, platelet activation, intimal hyperplasia, and/or vasospasm, or can bind to collagen in a denuded vessel.

Accordingly, in certain embodiments, the synthetic peptide is RYPISRPRKRGSG (SEQ ID NO: 49), RRA-NAALKAGELYKSILYGC (SEQ ID NO: 17), or GELYK-SILYGC (SEQ ID NO: 26).

In any of the embodiments described herein, a synthetic peptide (e.g., a collagen binding peptide) comprises any amino acid sequence described in the preceding paragraph or an amino acid sequence having at least about 80%, or at least about 83%, or at least about 85%, or at least about 90%, or at least about 95%, or at least about 98%, or at least about 100% homology to any of these amino acid sequences. In various embodiments, the peptide components of the synthetic peptidoglycan described herein can be modified by the inclusion of one or more conservative amino acid substitutions. As is well-known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in Table 1.

TABLE 1

| For Amino Acid | Replace With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In the various conservative amino acid substitution embodiments described herein, a collagen-binding synthetic peptidoglycan comprising a synthetic peptide of about 5 to about 40 amino acids with amino acid sequence homology to a collagen binding peptide (e.g., a portion of an amino acid sequence of a collagen binding protein or proteoglycan) conjugated to a glycan selected from the group consisting of alginate, agarose, dextran, chondroitin, dermatan, dermatan sulfate, heparan, heparin, keratin, and hyaluronan can be used. In one embodiment, the glycan is selected from the group consisting of dermatan sulfate, dextran, hyaluronan, and heparin. In another illustrative embodiment the glycan is dermatan sulfate. In yet another embodiment, the glycan is dermatan sulfate with about 18 peptides of the sequence RRANAALKAGELYKSILYGC (SEQ ID NO: 17) linked to the glycan and this sequence can be conservatively substituted. The collagen-binding synthetic proteoglycan in any of these conservative substitution embodiments can be used to inhibit platelet binding to exposed collagen of the denuded endothelium, platelet activation, thrombosis, inflammation resulting from denuding the endothelium, intimal hyperplasia, and/or vasospasm. The collagen-binding synthetic peptidoglycans described herein with conservative amino acid substitutions can also stimulate endothelial cell proliferation and can bind to collagen in a denuded vessel. In any of these embodiments, these aforementioned effects can occur during a vascular intervention procedure, such as a catheter-based procedure. In any of these conservative substitution embodiments, any of the above-described compounds can be used.

In another illustrative embodiment, any of the compounds selected from the group consisting of RRANAALKAGELYKSILYGC (SEQ ID NO: 17), RLDGNEIKRGC (SEQ ID NO: 18), AHEEISTTNEGVMGC (SEQ ID NO: 19), NGVFKYRPRYFLYKHAYFYPPLKRFPVQGC (SEQ ID NO: 20), CQDSETRTFY (SEQ ID NO: 7), TKKTLRTGC (SEQ ID NO: 21), GLRSKSKKFRRPDIQYPDATDEDITSHMGC (SEQ ID NO: 22), SQNPVQPGC (SEQ ID NO: 23), SYIRIADTNITGC (SEQ ID NO: 24), SYIRIADTNIT (SEQ ID NO: 11), KELNLVYT (SEQ ID NO: 12), KELNLVYTGC (SEQ ID NO: 25), GSITTIDVPWNV (SEQ ID NO: 14), GELYKSILYGC (SEQ ID NO: 26), GSITTIDVPWNVGC (SEQ ID NO: 13), and GCGGELYKSILY (SEQ ID NO: 27) having conservative amino acid substitutions can be used. In any of these embodiments the compounds with conservative amino acid substitutions can inhibit platelet binding to exposed collagen of the denuded endothelium, platelet activation, thrombosis, inflammation resulting from denuding the endothelium, intimal hyperplasia, and/or vasospasm, or can stimulate endothelial cell proliferation or can bind to collagen in a denuded vessel. In another illustrative embodiment, during a vascular intervention procedure, any of these compounds with conservative amino acid substitutions can inhibit platelet binding to exposed collagen of the denuded endothelium, platelet activation, thrombosis, inflammation resulting from denuding the endothelium, intimal hyperplasia, and/or vasospasm, or can stimulate endothelial cell proliferation or can bind to collagen in a denuded vessel. In another illustrative embodiment, during a vascular intervention procedure, any of the compounds with conservative amino acid substitutions described in this paragraph can inhibit platelet binding to exposed collagen of the denuded endothelium, platelet activation, intimal hyperplasia, and/or vasospasm, or inhibit inflammatory responses by inhibiting the production of selectins or ICAMs/VCAMs in dysfunctional endothelial cells.

As used herein, the term "extracellular matrix" refers to the extracellular part of tissue that provides structural and biochemical support to the surrounding cells.

As used herein, the term "linker" refers to chemical bond, atom, or group of atoms that connects two adjacent chains of atoms in a large molecule such as a peptide, synthetic peptidoglycan, protein or polymer. In various embodiments, the linker comprises two or more chemically orthogonal functionalities on a rigid scaffold (e.g., any suitable bifunctional linker, such as N-[β-maleimidopropionic acid]hydrazide (BMPH), 3-(2-pyridyldithio)propionyl hydrazide (PDPH)), or the peptide GSG (SEQ ID NO: 1).

In various embodiments of the methods disclosed herein, the glycan is dextran, chondroitin, chondroitin sulfate, dermatan, dermatan sulfate, heparan sulfate, heparin, keratin, keratan sulfate, or hyaluronic acid. In some embodiments the glycan can be any glycan (e.g., glycosaminoglycan or polysaccharide). In some embodiments, the glycan is dextran. In some embodiments, the glycan is chondroitin. In other embodiments, the glycan is chondroitin sulfate. In some embodiments, the glycan is dermatan. In some embodiments, the glycan is dermatan sulfate. In other embodiments, the glycan is heparan sulfate. In other embodiments, the glycan is heparin. In other embodiments, the glycan is keratin. In some embodiments, the glycan is keratan sulfate. In other embodiments, the glycan is hyaluronic acid. Various glycans may be employed including, a wide range of molecular weights, such as from about 1 kDa to about 2 MDa, or from about 10 kDa to about 2 MDa. In some embodiments, the glycan is from about 3 to about 5 MDa. In some embodiments, the glycan is up to about 3 MDa, or up to about 5 MDa, or up to about 60 MDa.

The peptide(s) can be bonded to the glycan directly or via a linker. In some embodiments, the linker can be any suitable bifunctional linker, e.g., N-[β-maleimidopropionic acid]hydrazide (BMPH), 3-(2-pyridyldithio)propionyl hydrazide (PDPH), and the like. In any of the various embodiments described herein, the sequence of the peptide may be modified to include a glycine-cysteine (GC) attached to the C-terminus of the peptide and/or a glycine-cysteine-glycine (GCG) attached to the N-terminus to provide an attachment point for a glycan or a glycan-linker conjugate. In certain embodiments, the linker is N-[β-maleimidopropionic acid] hydrazide (BMPH). In certain embodiments, the linker is 3-(2-pyridyldithio)propionyl hydrazide (PDPH). In some embodiments, the peptide to linker ratio is from about 1:1 to about 5:1. In other embodiments, the peptide to linker ratio is from about 1:1 to about 10:1. In other embodiments, the peptide to linker ratio is from about 1:1 to about 2:1, from about 1:1 to about 3:1, from about 1:1 to about 4:1, from about 1:1 to about 5:1, from about 1:1 to about 6:1, from about 1:1 to about 7:1, from about 1:1 to about 8:1, from about 1:1 to about 9:1. In one embodiment, the peptide linker ratio is about 1:1. In one embodiment, the peptide linker ratio is about 2:1. In one embodiment, the peptide linker ratio is about 3:1. In one embodiment, the peptide linker ratio is about 4:1. In one embodiment, the peptide linker ratio is about 5:1. In one embodiment, the peptide linker ratio is about 6:1. In one embodiment, the peptide linker ratio is about 7:1. In one embodiment, the peptide linker ratio is about 8:1. In one embodiment, the peptide linker ratio is about 9:1. In one embodiment, the peptide linker ratio is about 10:1.

Depending on the desired properties of the synthetic peptidoglycan, the total number of peptides bonded to the glycan can be varied. In certain embodiments, the total number of peptides present in the synthetic peptidoglycan is from about 1 or 2 to about 160, from about 10 to about 160, from about 20 to about 160, from about 30 to about 160, from about 40 to about 160, from about 40 to about 150, from about 40 to about 140, from about 10 to about 120, or from about 20 to about 110, or from about 20 to about 100, or from about 20 to about 90, or from about 30 to about 90, or from about 40 to about 90, or from about 50 to about 90, or from about 50 to about 80, or from about 60 to about 80, or about 10, or about 20, or about 30, or about 40, or about 50, or about 60, or about 70, or about 80, or about 90, or about 100, or about 110, or about 120. In certain embodiments, the synthetic peptidoglycan comprises less than about 50 peptides. In various embodiments, the synthetic peptidoglycan comprises from about 5 to about 40 peptides. In some embodiments, the synthetic peptidoglycan comprises from about 10 to about 40 peptides. In other embodiments, the synthetic peptidoglycan comprises from about 5 to about 20 peptides. In various embodiments, the synthetic peptidoglycan comprises from about 4 to about 18 peptides. In certain embodiments, the synthetic peptidoglycan comprises less than about 20 peptides. In certain embodiments, the synthetic peptidoglycan comprises less than about 18 peptides. In certain embodiments, the synthetic peptidoglycan comprises less than about 15 peptides. In certain embodiments, the synthetic peptidoglycan comprises less than about 10 peptides. In certain embodiments, the synthetic peptidoglycan comprises about 20 peptides. In certain embodiments, the synthetic peptidoglycan comprises about 40 peptides. In certain embodiments, the synthetic peptidoglycan comprises about 18 peptides. In certain embodiments, the synthetic peptidoglycan comprises from about 5 to about 40, or from about 10 to about 40, or from about 5 to about 20, or from about 4 to about 18, or about 10, or about 11, or about 18, or about 20 peptides.

Suitable collagen binding peptides are known (see, e.g., US 2013/0190246, US 2012/0100106, and US 2011/0020298, the disclosures of which are incorporated herein by reference in their entirety) or can be found by methods known in the art. In certain embodiments, the collagen binding peptide comprises from about 5 to about 40 amino acids. In some embodiments, these peptides have homology to the amino acid sequence of a small leucine-rich peptidoglycan, a platelet receptor sequence, or a protein that regulates collagen fibrillogenesis.

In various embodiments, the collagen binding peptide comprises an amino acid sequence selected from:

i) RRANAALKAGELYKSILY (SEQ ID NO: 2), RLDGNEIKR (SEQ ID NO: 3), AHEEISTTNEGVM (SEQ ID NO: 4), GELYKSILY (SEQ ID NO: 5), NGVFKYRPRYFLYKHAYFYPPLKRFPVQ (SEQ ID NO: 6), CQDSETRTFY (SEQ ID NO: 7), TKKTLRT (SEQ ID NO: 8), GLRSKSKKFRRPDIQYPDATDEDITSHM (SEQ ID NO: 9), SQNPVQP (SEQ ID NO: 10), SYIRIADTNIT (SEQ ID NO: 11), KELNLVYT (SEQ ID NO: 12), GSITTIDVPWNVGC (SEQ ID NO: 13), or GSITTIDVPWNV (SEQ ID NO: 14); or ii) a peptide comprising a sequence with at least about 80% sequence identity to the amino acid sequence of i) and capable of binding to collagen.

In certain embodiments, the collagen binding peptide(s) is RRANAALKAGELYKSILY (SEQ ID NO: 2) or a peptide having at least about 80% sequence to RRANAALKAGELYKSILY (SEQ ID NO: 2) and capable of binding to collagen. In some embodiments, the peptide sequence comprises a sequence with at least about 80% sequence identity, or at least about 83% sequence identity, or at least about 85% sequence identity, or at least about 90% sequence identity, or at least about 95% sequence identity, or at least about 98% sequence identity to the amino acid sequence of i) and capable of binding to collagen. In certain embodiments, the collagen binding peptide is at least about 80%, or at least about 83%, or at least about 85%, or at least about 90%, or at least about 95%, or at least about 98%, or at least about 100% homologous with the collagen binding domain(s) of the von Willebrand factor or a platelet collagen receptor as described in Chiang, T. M. et al. J. Biol. Chem., 2002, 277: 34896-34901; Huizinga, E. G. et al., Structure, 1997, 5: 1147-1156; Romijn, R. A. et al., J. Biol. Chem., 2003, 278: 15035-15039; and Chiang, et al., Cardio. & Haemato. Disorders-Drug Targets, 2007, 7: 71-75, each incorporated herein by reference.

In various embodiments, the collagen binding peptide comprises an amino acid spacer. Accordingly, in certain embodiments, the collagen binding peptide comprises an amino acid sequence selected from:

i) RRANAALKAGELYKSILYGC (SEQ ID NO: 17), RLDGNEIKRGC (SEQ ID NO: 18), AHEEISTTNEGVMGC (SEQ ID NO: 19), GCGGELYKSILY (SEQ ID NO: 27), NGVFKYRPRYFLYKHAYFYPPLKRFPVQGC (SEQ ID NO: 20), CQDSETRTFYGC (SEQ ID NO: 50), TKKTLRTGC (SEQ ID NO: 21), GLRSKSK-

KFRRPDIQYPDATDEDITSHMGC (SEQ ID NO: 22), SQNPVQPGC (SEQ ID NO: 23), SYIRIADTNITGC (SEQ ID NO: 24), KELNLVYTGC (SEQ ID NO: 25), GSITTI-DVPWNVGC (SEQ ID NO: 13), GCGGELYKSILYGC (SEQ ID NO: 51) or GELYKSILYGC (SEQ ID NO: 26); or ii) a peptide comprising a sequence with at least about 80% sequence identity to the amino acid sequence of i) and capable of binding to collagen. In some embodiments, the peptide sequence comprises a sequence with at least about 80% sequence identity, or at least about 83% sequence identity, or at least about 85% sequence identity, or at least about 90% sequence identity, or at least about 95% sequence identity, or at least about 98% sequence identity to the amino acid sequence of i) and capable of binding to collagen.

In one embodiment, the synthetic peptidoglycan comprises dermatan sulfate having from about 5 to about 40 collagen binding peptide(s) bonded thereto and wherein the collagen binding peptide(s) is RRANAALKAGELYKSILY (SEQ ID NO: 2) or a peptide having at least about 80% sequence identity to RRANAALKAGELYKSILY (SEQ ID NO: 2) and capable of binding to collagen.

Similarly for a collagen binding peptide, a synthetic peptide derived from a phage display library selected for collagen binding can be generated. The peptide can be synthesized and evaluated for binding to collagen by any of the techniques such as SPR, ELISA, ITC, affinity chromatography, or others known in the art. An example could be a biotin modified peptide sequence (e.g., $SILY_{biotin}$) that is incubated on a microplate containing immobilized collagen. A dose response binding curve can be generated using a streptavidin-chromophore to determine the ability of the peptide to bind to collagen.

In various embodiments described herein, the peptides described herein can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Non-conservative substitutions may too be possible, provided that they do not substantially affect the binding activity of the peptide (i.e., collagen binding affinity).

4. Synthesis of Synthetic Peptidoglycans

The peptides used in the method described herein (i.e., the collagen binding peptide) may be purchased from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification. Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan.

In certain embodiments, the peptides are covalently bonded to the glycan directly (i.e., without a linker). In such embodiments, the synthetic peptidoglycan may be formed by covalently bonding the peptides to the glycan through the formation of one or more amide, ester or imino bonds between an acid, aldehyde, hydroxy, amino, or hydrazo group on the glycan. All of these methods are known in the art. See, e.g., Hermanson G. T., Bioconjugate Techniques, Academic Press, pp. 169-186 (1996), incorporated herein by reference. As shown in Scheme 1, the glycan (e.g., chondroitin sulfate "CS") can be oxidized using a periodate reagent, such as sodium periodate, to provide aldehyde functional groups on the glycan (e.g., "ox-CS") for covalently bonding the peptides to the glycan. In such embodiments, the peptides may be covalently bonded to a glycan by reacting a free amino group of the peptide with an aldehyde functional groups of the oxidized glycan, e.g., in the presence of a reducing agent, utilizing methods known in the art.

In embodiments where the peptides are covalently bonded to the glycan via a linker, the oxidized glycan (e.g., "ox-CS") can be reacted with a linker (e.g., any suitable bifunctional liker, such as 3-(2-pyridyldithio)propionyl hydrazide (PDPH) or N-[β-maleimidopropionic acid]hydrazide (BMPH)) prior to contacting with the peptides. The linker typically comprises about 1 to about 30 carbon atoms, or about 2 to about 20 carbon atoms. Lower molecular weight linkers (i.e., those having an approximate molecular weight of about 20 to about 500) are typically employed. In addition, structural modifications of the linker are contemplated. For example, amino acids may be included in the linker, including but not limited to, naturally occurring amino acids as well as those available from conventional synthetic methods, such as beta, gamma, and longer chain amino acids.

As shown in Scheme 1, in one embodiment, the peptides are covalently bonded to the glycan (e.g., chondroitin sulfate "CS") by reacting an aldehyde function of the oxidized glycan (e.g., "ox-CS") with N-[β-maleimidopropionic acid] hydrazide (BMPH) to form an glycan intermediate (e.g., "BMPH-CS") and further reacting the glycan intermediate with peptides containing at least one free thiol group (i.e., —SH group) to yield the synthetic peptidoglycan. In yet another embodiment, the sequence of the peptides may be modified to include an amino acid residue or residues that act as a spacer between the HA- or Collagen-binding peptide sequence and a terminating cysteine (C). For example a glycine-cysteine (GC) or a glycine-glycine-glycine-cysteine (GGGC) (SEQ ID NO: 58) or glycine-serine-glycine-cysteine (GSGC) (SEQ ID NO: 56) segment may be added to provide an attachment point for the glycan intermediate.

Scheme 1. Synthesis of CS-BMPH-Peptide$_n$

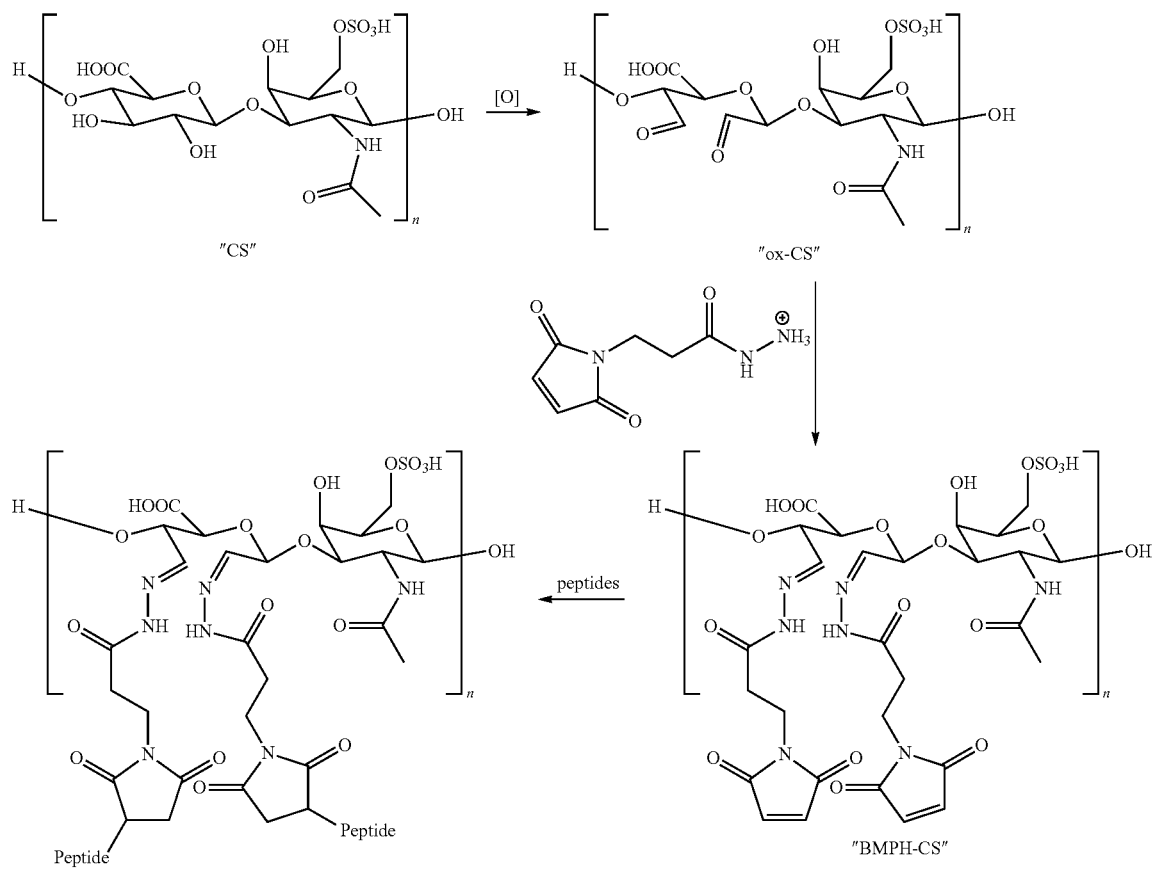

5. Compositions and Formulations

In one embodiment, the synthetic peptidoglycan is administered in a composition. The present disclosure provides compositions comprising a synthetic peptidoglycan and a pharmaceutically acceptable carrier. Pharmaceutically acceptable carriers are known to one having ordinary skill in the art may be used, including water or saline. As is known in the art, the components as well as their relative amounts are determined by the intended use and method of delivery.

The compositions provided in accordance with the present disclosure can be formulated, such as solutions, gels, or tablets, according to the disease to be treated and location of the disease or the dysfunctional endothelium.

In one embodiment, the composition is formulated as a solution. Diluent or carriers employed in the compositions can be selected so that they do not diminish the desired effects of the synthetic peptidoglycan. Examples of suitable compositions include aqueous solutions, for example, a solution in isotonic saline, 5% glucose. Other well-known pharmaceutically acceptable liquid carriers such as alcohols, glycols, esters and amides, may be employed. In certain embodiments, the composition further comprises one or more excipients, such as, but not limited to ionic strength modifying agents, solubility enhancing agents, sugars such as mannitol or sorbitol, pH buffering agent, surfactants, stabilizing polymer, preservatives, and/or co-solvents. In certain embodiments, the composition is an aqueous solution. Aqueous solutions are suitable for use in composition formulations based on ease of formulation, as well as an ability to easily administer such compositions by means of instilling the solution in.

In certain embodiments, the compositions are suspensions, viscous or semi-viscous gels, or other types of solid or semi-solid compositions. In some embodiments, the composition is in the form of foams, ointments, liquid wash, gels, sprays and liposomes, which are well known in the art. Alternatively, the topical administration is an infusion of the provided synthetic peptidoglycan to the disease site via a device selected from a pump-catheter system, a continuous or selective release device, or an adhesion barrier. In certain embodiments, the composition is a solution that is directly applied to or contacts the internal wall of a vein or artery of the affected vessel. In some embodiments, the composition comprises a polymer matrix. In other embodiments, the composition is absorbable. In certain embodiments, the composition comprises a pH buffering agent. In some embodiments, the composition contains a lubricity enhancing agent.

In certain embodiments, a polymer matrix or polymeric material is employed as a pharmaceutically acceptable carrier or support for the anti-adhesion composition. The polymeric material described herein may comprise natural or unnatural polymers, for example, such as sugars, peptides, protein, laminin, collagen, hyaluronic acid, ionic and non-ionic water soluble polymers; acrylic acid polymers; hydrophilic polymers such as polyethylene oxides, polyoxyethylene-polyoxypropylene copolymers, and polyvinylalcohol;

cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic. In certain embodiments, the anti-adhesion compositions provided herein is formulated as films, gels, foams, or and other dosage forms.

Suitable ionic strength modifying agents include, for example, glycerin, propylene glycol, mannitol, glucose, dextrose, sorbitol, sodium chloride, potassium chloride, and other electrolytes.

In certain embodiments, the solubility of the synthetic peptidoglycan may need to be enhanced. In such cases, the solubility may be increased by the use of appropriate formulation techniques, such as the incorporation of solubility-enhancing compositions such as mannitol, ethanol, glycerin, polyethylene glycols, propylene glycol, poloxomers, and others known in the art.

In certain embodiments, the composition contains a lubricity enhancing agent. As used herein, lubricity enhancing agents refer to one or more pharmaceutically acceptable polymeric materials capable of modifying the viscosity of the pharmaceutically acceptable carrier. Suitable polymeric materials include, but are not limited to: ionic and non-ionic water soluble polymers; hyaluronic acid and its salts, chondroitin sulfate and its salts, dextrans, gelatin, chitosans, gellans, other peptidoglycans or polysaccharides, or any combination thereof; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; collagen and modified collagens; galactomannans, such as guar gum, locust bean gum and tara gum, as well as polysaccharides derived from the foregoing natural gums and similar natural or synthetic gums containing mannose and/or galactose moieties as the main structural components (e.g., hydroxypropyl guar); gums such as tragacanth and xanthan gum; gellan gums; alginate and sodium alginate; chitosans; vinyl polymers; hydrophilic polymers such as polyethylene oxides, polyoxyethylene-polyoxypropylene copolymers, and polyvinylalcohol; carboxyvinyl polymers or crosslinked acrylic acid polymers such as the "carbomer" family of polymers, e.g., carboxypolyalkylenes that may be obtained commercially under the Carbopol™ trademark; and various other viscous or viscoelastomeric substances. In one embodiment, a lubricity enhancing agent is selected from the group consisting of hyaluronic acid, dermatan, chondroitin, heparin, heparan, keratin, dextran, chitosan, alginate, agarose, gelatin, hydroxypropyl cellulose, hydroxyethyl cellulose, hydroxypropyl methylcellulose, hydroxypropyl methylcellulose phthalate, methyl cellulose, carboxymethyl cellulose, and etherified cellulose, polyvinyl alcohol, polyvinylpyrrolidinone, povidone, carbomer 941, carbomer 940, carbomer 971P, carbomer 974P, or a pharmaceutically acceptable salt thereof. In one embodiment, a lubricity enhancing agent is applied concurrently with the synthetic peptidoglycan. Alternatively, in one embodiment, a lubricity enhancing agent is applied sequentially to the synthetic peptidoglycan. In one embodiment, the lubricity enhancing agent is chondroitin sulfate. In one embodiment, the lubricity enhancing agent is hyaluronic acid. The lubricity enhancing agent can change the viscosity of the composition.

For further details pertaining to the structures, chemical properties and physical properties of the above lubricity enhancing agents, see e.g., U.S. Pat. Nos. 5,409,904, 4,861,760 (gellan gums), U.S. Pat. No. 4,255,415, 4,271,143 (carboxyvinyl polymers), WO 94/10976 (polyvinyl alcohol), WO 99/51273 (xanthan gum), and WO 99/06023 (galactomannans). Typically, non-acidic lubricity enhancing agents, such as a neutral or basic agent are employed in order to facilitate achieving the desired pH of the formulation.

In some embodiments, the synthetic peptidoglycans can be combined with minerals, amino acids, sugars, peptides, proteins, vitamins (such as ascorbic acid), or laminin, collagen, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly (glycolic acid), copolymers of lactic and glycolic acids, or other polymeric agents both natural and synthetic.

Suitable pH buffering agents for use in the anti-adhesion compositions herein include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES. In certain embodiments, an appropriate buffer system (e.g., sodium phosphate, sodium acetate, sodium citrate, sodium borate or boric acid) is added to the composition to prevent pH drift under storage conditions. In some embodiments, the buffer is a phosphate buffered saline (PBS) solution (i.e., containing sodium phosphate, sodium chloride and in some formulations, potassium chloride and potassium phosphate). The particular concentration will vary, depending on the agent employed. In certain embodiments, the pH buffer system (e.g., sodium phosphate, sodium acetate, sodium citrate, sodium borate or boric acid) is added to maintain a pH within the range of from about pH 4 to about pH 8, or about pH 5 to about pH 8, or about pH 6 to about pH 8, or about pH 7 to about pH 8. In some embodiments, the buffer is chosen to maintain a pH within the range of from about pH 4 to about pH 8. In some embodiments, the pH is from about pH 5 to about pH 8. In some embodiments, the buffer is a saline buffer. In certain embodiments, the pH is from about pH 4 and about pH 8, or from about pH 3 to about pH 8, or from about pH 4 to about pH 7. In some embodiments, the composition is in the form of a film, gel, patch, or liquid solution which comprises a polymeric matrix, pH buffering agent, a lubricity enhancing agent and a synthetic peptidoglycan wherein the composition optionally contains a preservative; and wherein the pH of said composition is within the range of about pH 4 to about pH 8.

Surfactants are employed in the composition to deliver higher concentrations of synthetic peptidoglycan. The surfactants function to solubilize the inhibitor and stabilize colloid dispersion, such as micellar solution, microemulsion, emulsion and suspension. Suitable surfactants comprise c polysorbate, poloxamer, polyosyl 40 stearate, polyoxyl castor oil, tyloxapol, triton, and sorbitan monolaurate. In one embodiment, the surfactants have hydrophile/lipophile/balance (HLB) in the range of 12.4 to 13.2 and are acceptable for ophthalmic use, such as TritonX114 and tyloxapol.

In certain embodiments, stabilizing polymers, i.e., demulcents, are added to the composition. The stabilizing polymer should be an ionic/charged example, more specifically a polymer that carries negative charge on its surface that can exhibit a zeta-potential of (−)10-50 mV for physical stability and capable of making a dispersion in water (i.e. water soluble). In one embodiment, the stabilizing polymer comprises a polyelectrolyte or polyectrolytes if more than one, from the family of cross-linked polyacrylates, such as carbomers and Pemulen®, specifically Carbomer 974p (polyacrylic acid), at a range of about 0.1% to about 0.5% w/w.

In one embodiment, the composition comprises an agent which increases the permeability of the synthetic peptidoglycan to the extracellular matrix of blood vessels. Preferably the agent which increases the permeability is selected from benzalkonium chloride, saponins, fatty acids, polyoxyethylene fatty ethers, alkyl esters of fatty acids, pyrrolidones, polyvinylpyrrolidone, pyruvic acids, pyroglutamic acids or mixtures thereof.

The synthetic peptidoglycan may be sterilized to remove unwanted contaminants including, but not limited to, endotoxins and infectious agents. Sterilization techniques which do not adversely affect the structure and biotropic properties of the synthetic peptidoglycan can be used. In certain embodiments, the synthetic peptidoglycan can be disinfected and/or sterilized using conventional sterilization techniques including propylene oxide or ethylene oxide treatment, sterile filtration, gas plasma sterilization, gamma radiation, electron beam, and/or sterilization with a peracid, such as peracetic acid. In one embodiment, the synthetic peptidoglycan can be subjected to one or more sterilization processes. Alternatively, the synthetic peptidoglycan may be wrapped in any type of container including a plastic wrap or a foil wrap, and may be further sterilized.

In some embodiments, preservatives are added to the composition to prevent microbial contamination during use. Suitable preservatives added to the anti-adhesion compositions comprise benzalkonium chloride, benzoic acid, alkyl parabens, alkyl benzoates, chlorobutanol, chlorocresol, cetyl alcohols, fatty alcohols such as hexadecyl alcohol, organometallic compounds of mercury such as acetate, phenylmercury nitrate or borate, diazolidinyl urea, diisopropyl adipate, dimethyl polysiloxane, salts of EDTA, vitamin E and its mixtures. In certain embodiments, the preservative is selected from benzalkonium chloride, chlorobutanol, benzododecinium bromide, methyl paraben, propyl paraben, phenylethyl alcohol, edentate disodium, sorbic acid, or polyquarternium-1. In certain embodiments, the ophthalmic compositions contain a preservative. In some embodiments, the preservatives are employed at a level of from about 0.001% to about 1.0% w/v. In certain embodiments, the ophthalmic compositions do not contain a preservative and are referred to as "unpreserved". In some embodiments, the unit dose compositions are sterile, but unpreserved.

In some embodiments, separate or sequential administration of the synthetic peptidoglycan and other agent is necessary to facilitate delivery of the composition into the AVF. In certain embodiments, the synthetic peptidoglycan and the other agent can be administered at different dosing frequencies or intervals. For example, the synthetic peptidoglycan can be administered daily, while the other agent can be administered less frequently. Additionally, as will be apparent to those skilled in the art, the synthetic peptidoglycan and the other agent can be administered using the same route of administration or different routes of administration.

Any effective regimen for administering the synthetic peptidoglycan can be used. For example, the synthetic peptidoglycan can be administered as a single dose, or as a multiple-dose daily regimen. Further, a staggered regimen, for example, one to five days per week can be used as an alternative to daily treatment.

In various embodiments, the synthetic peptidoglycan can be administered topically, such as by film, gel, patch, or liquid solution. In some of the embodiments, the compositions provided are in a buffered, sterile aqueous solution. In certain embodiments, the solutions have a viscosity of from about 1 to about 100 centipoises (cps), or from about 1 to about 200 cps, or from about 1 to about 300 cps, or from about 1 to about 400 cps. In some embodiments, the solutions have a viscosity of from about 1 to about 100 cps. In certain embodiments, the solutions have a viscosity of from about 1 to about 200 cps. In certain embodiments, the solutions have a viscosity of from about 1 to about 300 cps. In certain embodiments, the solutions have a viscosity of from about 1 to about 400 cps. In certain embodiments, the solution is in the form of an injectable liquid solution. In other embodiments, the compositions are formulated as viscous liquids, i.e., viscosities from several hundred to several thousand cps, gels or ointments. In these embodiments, the synthetic peptidoglycan is dispersed or dissolved in an appropriate pharmaceutically acceptable carrier.

Exemplary compositions for use with the synthetic peptidoglycans for catheter-based delivery may comprise: a) a synthetic peptidoglycan as described herein; b) a pharmaceutically acceptable carrier; c) a polymer matrix; d) a pH buffering agent to provide a pH in the range of about pH 4 to about pH 8; and e) a water soluble lubricity enhancing agent in the concentration range of about 0.25% to about 10% total formula weight or any individual component a), b), c), d) ore), or any combinations of a), b), c), d) or e).

Formulations contemplated by the present disclosure may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In making pharmaceutical compositions that include synthetic peptidoglycans described herein, the active ingredient is usually diluted by an excipient or carrier and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of films, gels, patches, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin films, gels, patches, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

Films used for drug delivery are well known in the art and comprise non-toxic, non-irritant polymers devoid of leachable impurities, such as polysaccharides (e.g., cellulose, maltodextrin, etc.). In some embodiments, the polymers are hydrophilic. In other embodiments, the polymers are hydrophobic. The film adheres to tissues to which it is applied, and is slowly absorbed into the body over a period of about a week. Polymers used in the thin-film dosage forms described herein are absorbable and exhibit sufficient peel, shear and tensile strengths as is well known in the art. In some embodiments, the film is injectable. In certain embodiments, the film is administered to the patient prior to, during or after surgical intervention.

Gels are used herein refer to a solid, jelly-like material that can have properties ranging from soft and weak to hard and tough. As is well known in the art, a gel is a non-fluid colloidal network or polymer network that is expanded throughout its whole volume by a fluid. A hydrogel is a type of gel which comprises a network of polymer chains that are hydrophilic, sometimes found as a colloidal gel in which water is the dispersion medium. Hydrogels are highly absorbent and can contain a high degree of water, such as, for example greater than 90% water. In some embodiments, the gel described herein comprises a natural or synthetic polymeric network. In some embodiments, the gel comprises a hydrophilic polymer matrix. In other embodiments, the gel comprises a hydrophobic polymer matrix. In some embodiments, the gel possesses a degree of flexibility very similar to natural tissue. In certain embodiments, the gel is biocompatible and absorbable. In certain embodiments, the gel is administered to the patient prior to, during or after surgical intervention.

Liquid solution as used herein refers to solutions, suspensions, emulsions, drops, ointments, liquid wash, sprays, liposomes which are well known in the art. In some embodiments, the liquid solution contains an aqueous pH buffer agent which resists changes in pH when small quantities of acid or base are added. In certain embodiments, the liquid solution is administered to the patient prior to, during or after surgical intervention.

Exemplary formulations may comprise: a) synthetic peptidoglycan as described herein; b) pharmaceutically acceptable carrier; c) polymer matrix; and d) pH buffering agent to provide a pH in the range of about pH 4 to about pH 8, wherein said solution has a viscosity of from about 3 to about 30 cps for a liquid solution. In certain embodiments, the solutions have a viscosity of from about 1 to about 100 centipoises (cps), or from about 1 to about 200 cps, or from about 1 to about 300 cps, or from about 1 to about 400 cps. In some embodiments, the solutions have a viscosity of from about 1 to about 100 cps. In certain embodiments, the solutions have a viscosity of from about 1 to about 200 cps. In certain embodiments, the solutions have a viscosity of from about 1 to about 300 cps. In certain embodiments, the solutions have a viscosity of from about 1 to about 400 cps.

Alternatively, exemplary formulations may comprise: a) synthetic peptidoglycan as described herein; b) pharmaceutically acceptable carrier; and c) hydrophilic polymer as matrix network, wherein said compositions are formulated as viscous liquids, i.e., viscosities from several hundred to several thousand cps, gels or ointments. In these embodiments, the synthetic peptidoglycan is dispersed or dissolved in an appropriate pharmaceutically acceptable carrier.

In various embodiments described herein, formulations for parenteral administration may be formulated to be for immediate and/or modified release. Modified release formulations include delayed, sustained, pulsed, controlled, targeted and programmed release formulations. Thus, a collagen-binding synthetic peptidoglycan may be formulated as a solid, semi-solid, or thixotropic liquid for administration as an implanted depot providing modified release of the active compound. Illustrative examples of such formulations include drug-coated stents and copolymeric(dl-lactic, glycolic)acid (PGLA) microspheres. In another embodiment, collagen-binding synthetic peptidoglycans or compositions comprising collagen-binding synthetic peptidoglycan may be continuously administered, where appropriate.

In any of the embodiments described herein, the collagen-binding synthetic peptidoglycan can be administered intravascularly into the patient (e.g., into an artery or vein) in any suitable way. In various embodiments described herein, the collagen-binding synthetic peptidoglycan can be administered into a vessel of a patient prior to, during, or after vascular intervention. In various embodiments, vascular interventions, such as percutaneous coronary intervention (PCI), can include, for example, stenting, atherectomy, grafting, and angioplasty, such as balloon angioplasty. Illustratively, the vascular intervention can be one which involves temporarily occluding an artery, such as a coronary artery or a vein (e.g., balloon angioplasty), or it can be one which does not involve temporarily occluding an artery or a vein (e.g., non-balloon angioplasty procedures, stenting procedures that do not involve balloon angioplasty, etc.).

Illustrative modes of delivery can include a catheter, parenteral administration, a coating on a ballon, through a porous ballon, a coated stent, and any combinations thereof or any other known methods of delivery of drugs during a vascular intervention procedure. In one illustrative embodiment, the target vessel can include a coronary artery, e.g., any blood vessel which supplies blood to the heart tissue of a patient, including native coronary arteries as well as those which have been grafted into the patient, for example, in an earlier coronary artery bypass procedure.

In any of the embodiments described herein, the target vessel into which the collagen-binding synthetic peptidoglycan is to be administered and on which the vascular intervention procedure is to be performed may contain a blockage, such as a stenosis or some other form of complete or partial blockage which causes reduced blood flow through the vessel. Thus, the collagen-binding synthetic peptidoglycan can be delivered to the vessel via a catheter (e.g., a dilatation catheter, an over-the-wire angioplasty balloon catheter, an infusion catheter, a rapid exchange or monorail catheter, or any other catheter device known in the art) which is percutaneously inserted into the patient and which is threaded through the patient's blood vessels to the target vessel. Various catheter-based devices are known in the art, including those described in U.S. Pat. No. 7,300,454, incorporated herein by reference. In various embodiments described herein where a catheter is used, the catheter used to deliver the collagen-binding synthetic peptidoglycan can be the same catheter through which the vascular intervention is to be performed, or it can be a different catheter (e.g., a different catheter which is percutaneously inserted into the patient via the same or a different cutaneous incision and/or which is threaded through the patient's blood vessels to the target vessel via the same or a different route). In another embodiment, the collagen-binding synthetic peptidoglycan can be injected directly into the target vessel. In another embodiment, the collagen-binding synthetic peptidoglycan can be delivered systemically (i.e., not delivered directly to the target vessel, but delivered by parenteral administration without catheter-based delivery).

In the case where the vessel contains a blockage (e.g., a stenosis), administration can be carried out by delivering the collagen-binding synthetic peptidoglycan directly to the target vessel at the site of the blockage or distal to the blockage or both. In another embodiment, the collagen-binding synthetic peptidoglycan can be delivered to one or more sites proximal to the blockage. Illustratively, the catheter tip can be maintained stationary while the collagen-binding synthetic peptidoglycan is being delivered, or the catheter tip can be moved while the collagen-binding synthetic peptidoglycan is being delivered (e.g., in a proximal direction from a position that is initially distal to the blockage, to or through the blockage, or to a position which is proximal to the blockage).

As indicated above, in one embodiment, the collagen-binding synthetic peptidoglycan can be administered directly into the patient's vessel at a time prior to vascular intervention, e.g., percutaneous coronary intervention. For example, delivery of the collagen-binding synthetic peptidoglycan can be carried out just prior to vascular intervention (e.g., within about 1 hour, such as within about 30 minutes, within about 15 minutes, and/or within about 5 minutes prior to vascular intervention). Optionally, delivery of the collagen-binding synthetic peptidoglycan directly to the target vessel can be continued during all or part of the vascular intervention procedure and/or subsequent to completion of such procedure, or delivery of the collagen-binding synthetic peptidoglycan directly to the target vessel can be stopped prior to the commencement of the vascular intervention procedure and not subsequently re-commenced. In any of the embodiments described herein, delivery of the collagen-binding synthetic peptidoglycan can be continuous or it can be effected through a single or multiple administrations. Prior to, during, and/or after the collagen-binding synthetic peptidoglycan is administered to the target vessel, the same collagen-binding synthetic peptidoglycan or one or more different collagen-binding synthetic peptidoglycans can be administered.

In any of the embodiments described herein, the collagen-binding synthetic peptidoglycan can be administered alone or in combination with suitable pharmaceutical carriers or diluents. Diluent or carrier ingredients used in the collagen-binding synthetic peptidoglycan formulation can be selected so that they do not diminish the desired effects of the collagen-binding synthetic peptidoglycan. The collagen-binding synthetic peptidoglycan formulation may be in any suitable form. Examples of suitable dosage forms include aqueous solutions of the collagen-binding peptidoglycan, for example, a solution in isotonic saline, 5% glucose or other well-known pharmaceutically acceptable liquid carriers such as alcohols, glycols, esters and amides.

Suitable dosages of the collagen-binding synthetic peptidoglycan can be determined by standard methods, for example by establishing dose-response curves in laboratory animal models or in clinical trials. Illustratively, suitable dosages of collagen-binding synthetic peptidoglycan (administered in a single bolus or over time) include from 1 ng/kg to about 10 mg/kg, 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In other illustrative aspects, effective doses can range from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose.

Vascular intervention, such as percutaneous coronary intervention, can be carried out by any conventional procedure prior to, during, or after administration of the collagen-binding synthetic peptidoglycan. Examples of vascular intervention procedures contemplated for use in conjunction with the method of the present disclosure include stenting, atherectomy, and angioplasty, such as balloon angioplasty. The vascular intervention procedure can be one which involves temporarily occluding the vessel (e.g., balloon angioplasty), or it can be one which does not involve temporarily occluding the vessel (e.g., non-balloon angioplasty procedures, stenting procedures that do not involve balloon angioplasty, etc.). Illustrative modes of delivery can include a catheter, parenteral administration, a coating on a ballon, through a porous ballon, a coated stent, and any combinations thereof or any other known methods of delivery of drugs during a vascular intervention procedure.

In any of the embodiments herein described, kits for carrying out vascular intervention, such as the kits described above, are contemplated. The kits can include a catheter or a stent and a collagen-binding synthetic peptidoglycan. The collagen-binding synthetic peptidoglycan can be provided in any of the formulations discussed above and in an amount needed to carry our a single vascular intervention, such as from 1 ng/kg to about 10 mg/kg, 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In various embodiments herein described, effective doses provided in the formulations can range from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. Articles of manufacture are also contemplated for any of these embodiments.

In any of the kit or article of manufacture embodiments described herein, the kit or article of manufacture can comprise a dose or multiple doses of the collagen-binding synthetic peptidoglycan. The collagen-binding synthetic peptidoglycan can be in a primary container, for example, a glass vial, such as an amber glass vial with a rubber stopper and/or an aluminum tear-off seal. In another embodiment, the primary container can be plastic or aluminum, and the primary container can be sealed. In another embodiment, the primary container may be contained within a secondary container to further protect the composition from light.

In any of the embodiments described herein, the kit or article of manufacture can contain instructions for use. Other suitable kit or article of manufacture components include excipients, disintegrants, binders, salts, local anesthetics (e.g., lidocaine), diluents, preservatives, chelating agents, buffers, tonicity agents, antiseptic agents, wetting agents, emulsifiers, dispersants, stabilizers, and the like. These components may be available separately or admixed with the collagen-binding synthetic peptidoglycan. Any of the composition embodiments described herein can be used to formulate the kit or article of manufacture.

In various embodiments herein described, the kit can contain more than one catheter or a stent and a plurality of separate containers, each containing sterilized collagen-binding synthetic peptidoglycan formulations in an amount needed to carry out a single or multiple vascular interventions. Any type of stent or catheter may be included with the kit, including, for example, dilatation catheters, over-the-wire angioplasty balloon catheters, infusion catheters, rapid exchange or monorail catheters, and the like.

It is also contemplated that any of the formulations described herein may be used to administer the collagen-binding synthetic peptidoglycan (e.g., one or more types) either in the absence or the presence of a catheter-based device. The collagen-binding synthetic proteoglycan can be formulated in an excipient. In any of the embodiments described herein, the excipient can have a concentration ranging from about 0.4 mg/ml to about 6 mg/ml. In various embodiments, the concentration of the excipient may range from about 0.5 mg/ml to about 10 mg/ml, about 0.1 mg/ml to about 6 mg/ml, about 0.5 mg/ml to about 3 mg/ml, about 1 mg/ml to about 3 mg/ml, about 0.01 mg/ml to about 10 mg/ml, and about 2 mg/ml to about 4 mg/ml.

6. Dosing

Suitable dosages of the synthetic peptidoglycan can be determined by standard methods, for example by establishing dose-response curves in laboratory animal models or in clinical trials and can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, a dose ranges from about 0.0001 mg to about 10 mg. In other illustrative aspects, effective doses ranges from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. In any of the various embodiments described herein, effective doses ranges from about 0.01 µg to about 1000 mg per dose, 1 µg to about 100 mg per dose, about 100 µg to about 1.0 mg, about 50 µg to about 600 µg, about 50 µg to about 700 µg, about 100 µg to about 200 µg, about 100 µg to about 600 µg, about 100 µg to about 500 µg, about 200 µg to about 600 µg, or from about 100 µg to about 50 mg per dose, or from about 500 µg to about 10 mg per dose or from about 1 mg to about 10 mg per dose. In other illustrative embodiments, effective doses can be about 1 µg, about 10 µg, about 25 µg, about 50 µg, about 75 µg, about 100 µg, about 125 µg, about 150 µg, about 200 µg, about 250 µg, about 275 µg, about 300 µg, about 350 µg, about 400 µg, about 450 µg, about 500 µg, about 550 µg, about 575 µg, about 600 µg, about 625 µg, about 650 µg, about 675 µg, about 700 µg, about 800 µg, about 900 µg, 1.0 mg, about 1.5 mg, about 2.0 mg, about 10 mg, about 100 mg, or about 100 mg to about 30 grams. In certain embodiments, the dose is from about 0.01 mL to about 10 mL.

In some embodiments, the synthetic peptidoglycan is administered to the patient to achieve a desired plasma concentration proximate the dysfunctional endothelium. In one aspect, the desired plasma concentration, determined in terms of molar amount of individual collagen binding peptides, is at least 20 µM, or at least 40 µM, 60 µM, 80 µM, 100 µM, 150 µM, 200 µM, 300 µM, or 400 µM. In one aspect, the desired plasma concentration, determined in terms of molar amount of individual collagen binding peptides, is not higher than 100 µM, or not higher than 200 µM, 300 µM, 400 µM, 500 µM, 600 µM, 700 µM, 800 µM, 900 µM, 1000 µM, 2000 µM, or 5000 µM. In some embodiments, the desired plasma concentration, determined in terms of molar amount of individual collagen binding peptides, is from 20 to 2000 µM, from 20 or 40 to 1000 µM, from 20, 40 or 100 to 500 µM, from 50 or 100 to 500 µM, or from 100 to 200 or 250 µM.

In some embodiments, the compositions are packaged in multidose form. Preservatives are thus required to prevent microbial contamination during use. In certain embodiments, suitable preservatives as described above can be added to the compositions. In some embodiments, the composition contains a preservative. In certain embodiments the preservatives are employed at a level of from about 0.001% to about 1.0% w/v. In some embodiments, the unit dose compositions are sterile, but unpreserved.

EXPERIMENTAL EXAMPLES

In the following illustrative examples, the terms "synthetic peptidoglycan" and "conjugate" are used synonymously with the term "collagen binding synthetic peptidoglycan."

Example 1

Peptide Synthesis

All peptides were synthesized using a Symphony peptide synthesizer (Protein Technologies, Tucson, Ariz.), utilizing an FMOC protocol on a Knorr resin. The crude peptide was released from the resin with TFA and purified by reverse phase chromatography on an AKTAexplorer (GE Healthcare, Piscataway, N.J.) utilizing a Grace-Vydac 218TP C-18 reverse phase column and a gradient of water/acetonitrile 0.1% TFA. Dansyl-modified peptides were prepared by adding an additional coupling step with dansyl-Gly (Sigma) before release from the resin. Peptide structures were confirmed by mass spectrometry. The following peptides were prepared as described above: RRANAALKAGELYKSILYGC (SEQ ID NO: 17), SYIRIADTNIT (SEQ ID NO: 11), Dansyl-GRRANAALKAGELYKSILYGC (SEQ ID NO: 52), and Dansyl-GSYIRIADTNIT (SEQ ID NO: 53). These peptides are abbreviated SILY, SYIR, Z-SILY, and Z-SYIR. A biotin-labeled Z-SYIR peptide has also been synthesized using protocols known in the art and the peptide is amide terminated. Additional peptides, KELNLVYTGC (abbreviated KELN) (SEQ ID NO: 25) and GSITTIDVPWNVGC (abbreviated GSIT) (SEQ ID NO: 13) were prepared as described above or purchased (GenScript, Piscataway, N.J.).

Example 2

Cell Culture and Selectin Knockdown with DS-SILY

This example demonstrates that the synthetic peptidoglycan DS-SILY inhibits the expression of E-selectin and P-selectin in human endothelial cells.

Figure 1B:
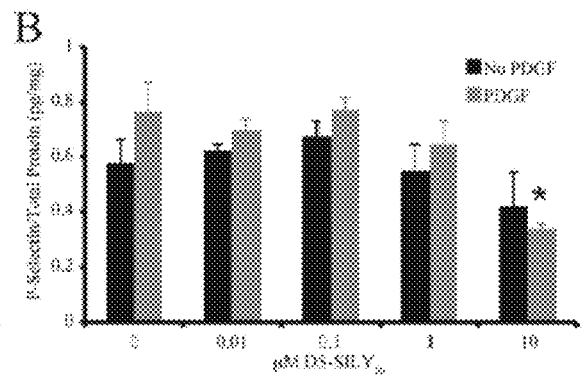

Referring to FIGS. 1A and 1B, human aortic endothelial cells (HAEC) (Invitrogen) were cultured in growth medium (Medium 200 supplemented with low serum growth supplement; Invitrogen). Cells from passages 3-5 were used for all experiments. Growth medium was used for all experiments unless otherwise noted. HAECs were seeded at $1 \times 10^5$ cells/$cm^2$ in growth medium on to Ibidi angiogenesis μ-slides (Ibidi) and allowed to adhere for 24 hrs. Growth medium was aspirated and cells were incubated in growth medium containing 0.01, 0.1, 1, and 10 μM DS-SILY$_{20}$ with or without 10 ng/mL platelet-derived growth factor (PDGF) for 24 hrs. Cells were washed twice with ice cold PBS and solubilized in lysis buffer (9 M urea, 4% CHAPS, and phosphatase inhibitor cocktail-1 in Millipore water). Lysates were processed at 4° C. for 30 mins prior to centrifugation for 20 mins at 18, to remove membrane components. A BCA assay protein kit (Pierce) was used to quantify total protein. A Vascular Injury Marker I kit (Meso Scale Discovery) was used to analyze E-selectin and P-selectin, production in HAECs according to manufacturer's instructions. Plates were imaged using a Sector Imager 2400A; data were analyzed using the MSD Discovery Workbench Software.

As shown in FIGS. 1A and 1B, incubation with SILY$_{20}$ dose-dependently decreased the expression of E-selectin (1A) and P-selectin (1B) in the presence (gray bars) or absence (black bars) of PDGF.

Example 3

DS-SILY Promotes Endothelial Cell Health

This example demonstrates that the synthetic peptidoglycan DS-SILY increases EC proliferation and migration, while attenuating IL-6 secretion and the production of vascular injury markers, even in the presence of PDGF. Further, in hyperplastic and quiescent EC-smooth muscle cells (SMC) co-cultures, DS-SILY decreases pro-inflammatory cytokine secretion and reduces E-selectin and P-selectin expression.

Cell Culture

Human aortic endothelial cells (EC, Invitrogen) were cultured in Media 200 (M200, Invitrogen), supplemented with (all from Invitrogen) 2% fetal bovine serum (FBS), 1 μg/mL hydrocortisone, 10 ng/mL epidermal growth factor (EGF), 3 ng/mL basic fibroblast growth factor (FGF), and 10 μg/mL heparin. Unless otherwise noted, cells were initially seeded at $3 \times 10^5$ cells/$cm^2$ in Ibidi angiogenesis μ-slide (Ibidi) and allowed to proliferate for 24 hrs to establish a confluent monolayer, prior to the application of treatments to the EC cultures. Cells were used between passage numbers 3 and 8 for all assays and maintained at 37° C. with 5% $CO_2$.

To better mimic the physiology of the vessel wall and further investigate the effects of therapeutics on ECs in a biologically relevant manner, two EC-SMC co-culture models, designed to mimic either healthy or diseased vasculature, were established. ECs were cultured as stated previously. Human coronary artery smooth muscle cells (SMC, Invitrogen) were cultured in Media 231 (M231, Invitrogen), supplemented with (all from Invitrogen) 4.9% FBS, 2 ng/mL FGF, 0.5% EGF, 5 ng/mL heparin, 5 μg/mL insulin, and 0.2 μg/mL bovine serum albumin. SMCs were seeded at $5 \times 10^4$ cells/$cm^2$ in Ibidi angiogenesis μ-slide and allowed to proliferate for 24 hrs to allow the formation of multilayered cell constructs. Media was removed and cultures were treated either with proliferative media, as described above, or contractile media to induce a quiescent phenotype, for 24 hrs.

Addition of contractile media, consisting of M231 supplemented with 1% FBS and 30 μg/mL heparin, induced SMCs to transition from a proliferative state to a more differentiated, contractile state due to low serum and introduction of heparin. After 24 hrs, ECs were seeded at $3 \times 10^5$ cells/$cm^2$ in co-culture media, consisting of M200 supplemented with 2% FBS, 1 μg/mL hydrocortisone, and 30 μg/mL heparin, to either the hyperplastic or quiescent SMC sublayer. ECs formed a monolayer atop of the SMC sublayers after 24 hrs and treatments were then applied to the co-cultures. All cells were used between passage numbers 3 and 8 for all assays and maintained at 37° C. with 5% $CO_2$.

Metabolic Activity

Cultures were incubated in the presence of 0, 0.01, 0.1, 1, or 10 μM DS-SILY$_{20}$, with and without 10 ng/mL PDGF, for 24 hrs. The metabolic activity of the cells was determined using the CellTiter 96 AQ$_{ueous}$ One Solution Cell Proliferation Assay (Promega). Briefly, media was mixed with 3-(4, 5-dimethylthiazol-2-yl)-5-(3-carboxymethoxyphenyl)-2-(4-sulfophenyl)-2H-tetrazolium, inner salt (MTS) and cultures were re-incubated for 2 hrs at 37° C. with 5% $CO_2$. The media containing MTS was then transferred into a 96-well plate and absorbance at 490 nm was measured.

Cell Viability

Cultures were incubated in the presence of 0, 0.01, 0.1, 1, or 10 μM DS-SILY$_{20}$, with and without 10 ng/mL PDGF, for 24 hrs. To test cytotoxicity of DS-SILY$_{20}$, EC viability was analyzed using LIVE/DEAD Viability/Cytotoxicity Assay Kit (Invitrogen) according to the manufacturer's instruction. Briefly, cultures were rinsed with PBS following treatment and 50 μL of mixed solution of 2 μM Calcein AM and 2 μM ethidium homodimer-1 was added directly to cells. Following incubation for 30 mins at room temperature, fluorescent intensity of the cultures was assessed via spectrophotometer to determine cell viability.

EC Proliferation

Cultures were incubated in the presence of DS-SILY$_{20}$ with or without 10 ng/mL PDGF for 24 hrs. Cells were nuclei stained with Hoescht 33342 and absorbance was measured via spectrophotometer to determine the effect of DS-SILY$_{20}$ and PDGF on cell proliferation.

EC Migration

Fibrillar collagen was coated in wells of 96-well Oris Cell Migration Kit (Platypus Technologies, Madison). Stoppers were inserted into the plate to block an inner circular portion of the well. ECs were seeded at 5×10$^3$ cells/well and grown to confluence in the outer portion of the well. After 48 hrs, the stoppers in the wells were removed and ECs were stained with cell tracker green (Invitrogen). To determine the effects of treatments on migration alone, ECs were dosed with 25 µg/mL mitomycin C (Sigma) for 30 mins to inhibit proliferation. Various DS-SILY$_{20}$ concentrations, solubilized in M200+LSGS, were then incubated on the exposed collagen surface in the inner portion of the well for 15 min at 37° C. Unbound DS-SILY$_{20}$ was rinsed from the surface and cell media, with or without 10 ng/mL PDGF, was returned to the wells. ECs were allowed to migrate from the outer to the inner portion of the wells for 48 hrs. At 48 hrs, fluorescence measurements of the center of each well were measured using a mask provided with the migration kit such that only the treated inner circular portion of the well was measured.

Pro-Inflammatory Cytokine Expression

Cells were incubated in the presence of DS-SILY$_{20}$ with or without 10 ng/mL PDGF for 24 hrs. Media was removed from the cultures and a Pro-Inflammatory I kit (Meso Scale Discovery) was used to analyze cytokine production from EC monolayers, hyperplastic co-cultures, and quiescent co-cultures according to manufacturer's instructions. Briefly, plates were warmed to room temperature and incubated with 25 µL of samples and standards for 2 hrs at room temperature with vigorous shaking. The detection antibody was then added to the plate and incubated for 2 hrs at room temperature with vigorous shaking. After washing three times with PBS with 0.05% Tween-20, 2× read buffer was added to the plate and imaged using a Sector Imager 2400A (Meso Scale Discovery). The pro-inflammatory markers interferon-γ (IFN-γ), interleukin-1β (IL-1β), interleukin-6 (IL-6), and tumor necrosis factor-α (TNF-α) were examined in this study. Data were analyzed using the MSD Discovery Workbench Software.

Production of Vascular Injury Markers

Following treatment with DS-SILY$_{20}$ with or without 10 ng/mL PDGF for 24 hrs, cells were washed twice with ice cold PBS and solubilized in lysis buffer (9 M urea, 4% CHAPS, and phosphatase inhibitor cocktail-1 in Millipore water). Lysates were processed at 4° C. for 30 mins prior to centrifugation for 20 mins at 18,000×g to remove membrane components. A BCA assay protein kit (Pierce) was used to quantify total protein. A Vascular Injury Marker I kit (Meso Scale Discovery) was used to analyze E-selectin, P-selectin, and thrombomodulin production from EC monolayers, hyperplastic co-cultures, and quiescent co-cultures according to manufacturer's instructions. Briefly, plates were warmed to room temperature and incubated with 10 µL of samples and standards for 2 hrs at room temperature with vigorous shaking. Following gentle rinsing of the wells, the detection antibody was then added and incubated for 1 hr at room temperature with vigorous shaking. After washing three times with PBS with 0.05% Tween-20, 2× Read buffer was added to the plate and imaged using a Sector Imager 2400A. Data were analyzed using the MSD Discovery Workbench Software.

MAPK Phosphorylation

The phosphorylation of mitogen-activated protein kinases (MAPK), including extracellular signal-related kinase (ERK) and p38 MAPK (p38), was examined. Cells were incubated in the presence of DS-SILY$_{20}$ with or without 10 ng/mL PDGF for 10 prior to washing with ice cold tris buffered saline (TBS) and solubilized in lysis buffer (150 mM NaCl, 20 mM Tris, 1 mM EDTA, 1 mM EGTA, 1% Triton-X-100, plus protease inhibitors and phosphatase inhibitors). Lysates were processed at 4° C. for 30 mins prior to centrifugation for 20 mins at 18,000×g to remove membrane components. Phospho-p38 (Thr180/Tyr182) and phospho-ERK-1/2 (Thr/Tyr: 202/204; 185/187) levels were evaluated using the MAP Kinase Whole Cell Lysate kit (Meso Scale Discovery); Total p38 and total ERK-1/2 were determined via MAP Kinase (Total Protein) Whole Cell Lysate Kit (Meso Scale Discovery), according to manufacturer's instructions. Briefly, plates were warmed to room temperature and incubated with 25 µL of samples for 3 hrs at room temperature with vigorous shaking. Following gentle rinsing of the wells, the detection antibody was then added and incubated for 1 hr at room temperature with vigorous shaking. After washing three times with TBS, 2× read buffer was added to the plate and imaged using a Sector Imager 2400A. Data were analyzed using the MSD Discovery Workbench Software. The relative amount of phosphorylated p38 and ERK-1/2 were normalized to total p38 and ERK-1/2 for each sample.

PDGFRβ Phosphorylation

Cells were incubated in the presence of DS-SILY$_{20}$ with and without 10 ng/mL PDGF for 60 mins prior to washing with ice cold TBS and the addition of lysis buffer prior to washing with ice cold TBS and solubilized in lysis buffer (1% NP-40 Alternative, 20 mM Tris, 137 mM NaCl, 10% glycerol, 2 mM EDTA, 1 mM activated sodium orthovanadate, 10 µg/mL Aprotinin, and 10 µg/mL Leupeptin). Lysates were processed at 4° C. for 30 mins prior to centrifugation for 5 mins at 2000×g to remove membrane components. Sandwich ELISAs (all from R&D systems) were utilized to measure total PDGF receptor β (PDGFRβ) and total phosphotyrosine PDGFRβ. All assays were performed following the manufacturer's protocol.

Statistical Analysis

Results are expressed as means±standard error. Statistical analysis was performed using SAS software (SAS Institute). All results were analyzed using ANOVA with Tukey HSD post-hoc test. The threshold for statistical significance was set at p<0.05.

Results

EC and EC-SMC Co-Culture Metabolic Activity

EC metabolic activity was assessed via the CellTiter 96 AQ$_{ueous}$ One Solution Cell Proliferation Assay. Low concentrations of DS-SILY$_{20}$ did not alter the metabolic activity of ECs, compared to no treatment controls (FIG. 2A). However, metabolic activity in ECs significantly decreased following treatment with 10 µM DS-SILY$_{20}$. The addition of 10 ng/mL PDGF alone did not influence the metabolic activity of ECs. Similar to results seen when ECs where treated with DS-SILY$_{20}$ alone, a significant decrease in metabolism was observed when PDGF-stimulated ECs were treated with 10 µM DS-SILY$_{20}$. However, no changes in metabolic activity were observed in PDGF-treated cultures stimulated with lower concentrations of DS-SILY$_{20}$.

DS-SILY$_{20}$, at every concentration tested, did not alter the metabolic activity of either the hyperplastic or quiescent co-cultures, compared to no treatment controls (FIGS. 2B and C). Further, the metabolic activity of the co-cultures was not impacted via PDGF stimulation alone or with the subsequent addition of DS-SILY$_{20}$.

Viability of ECs and EC-SMC Co-Cultures

To further explore the impact of DS-SILY$_{20}$ on EC monolayers, hyperplastic co-cultures, and quiescent co-cultures, a cell viability assay was completed (FIG. 2D-F). After 24 hrs of stimulation, 96.0%±0.8% of ECs were found viable in no treatment control cultures. Both hyperplastic and quiescent co-cultures exhibited less viability compared to ECs, where 73.2%±1.0% and 76.1%±1.5% of cells remained viable after 24 hrs of treatment, respectively. The addition of any concentration of DS-SILY$_{20}$, with or without added PDGF, did not significantly alter cell viability in EC monolayer cultures or in either co-culture system.

PDGFRβ Phosphorylation in ECs

Figure 3:
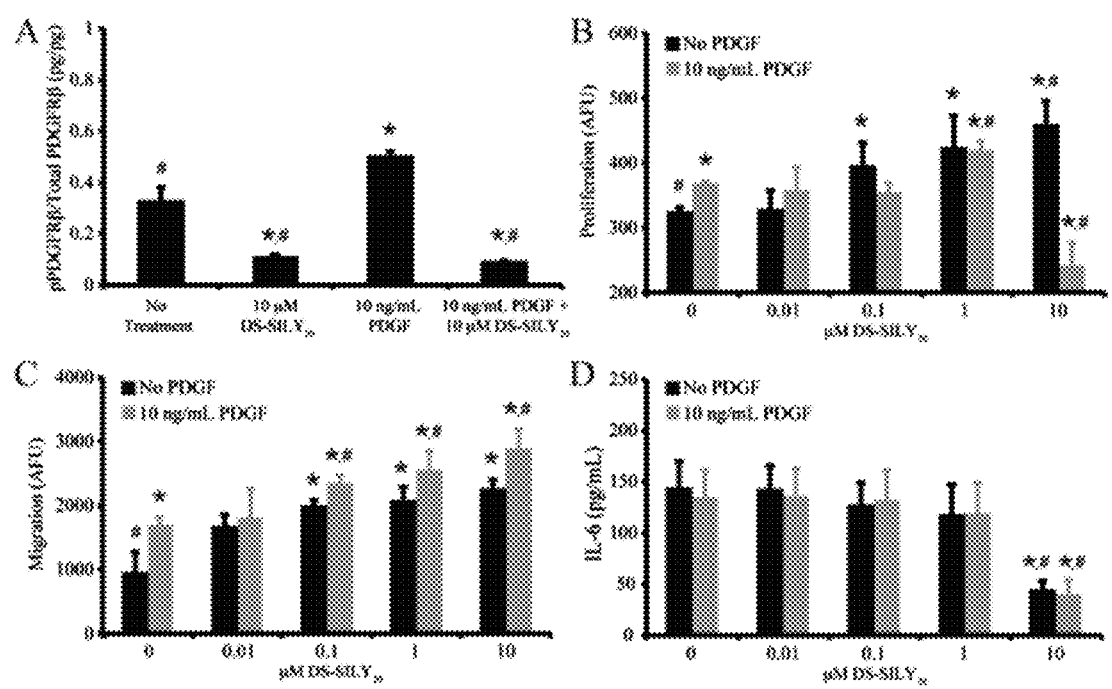
FIG. 3A-D shows that DS-SILY$_{20}$ regulates phosphorylation of PDGFRβ, proliferation, migration, and IL-6 production in ECs. (A) Relative phosphorylated PDGFRβ produced in ECs treated with 10 μM DS-SILY$_{20}$ and 10 ng/mL PDGF. The relative amount of phosphorylated PDGFRβ was normalized to total PDGFRβ for each sample. (B) Proliferation of ECs in response to DS-SILY$_{20}$ treatment, with and without PDGF stimulation. (C) EC migration in response to DS-SILY$_{20}$ treatment, with and without PDGF stimulation. (D) EC production of IL-6 in response to DS-SILY$_{20}$ treatment, with and without PDGF stimulation. * represents significance from control non-treated cells; # represents significance PDGF-treated cultures. (N>3).

To assess the ability of DS-SILY$_{20}$ to influence PDGF signaling in EC monolayers, phosphorylation of PDGFRO was investigated. The addition of 10 μM DS-SILY$_{20}$ to EC monolayers significantly decreased phospho-PDGFRβ compared to no treatment controls (FIG. 3A). Conversely, phospho-PDGFRβ levels were significantly increased in EC monolayers with PDGF treatment. However, the addition of DS-SILY$_{20}$ to PDGF-stimulated ECs resulted in significantly decreased phosphorylation of PDGFRβ, compared to both EC cultures stimulated with PDGF alone and to no treatment control cultures.

EC Proliferation is Enhanced By DS-SILY$_{20}$

EC proliferation was assessed by examining changes in absorbance of nuclei-stained cells following treatment for 24 hrs. The addition of DS-SILY$_{20}$ increased EC proliferation in a dose-dependent manner, where the addition of 10 μM DS-SILY$_{20}$ resulted in a 1.5-fold increase in proliferation compared to no treatment controls (FIG. 3B). PDGF also significantly increased proliferation in monolayer EC cultures. The co-addition of PDGF and low concentrations of DS-SILY$_{20}$ did not result in a synergistic increase in proliferation; rather, proliferation in PDGF-stimulated ECs treated with 0.01 or 0.1 μM DS-SILY$_{20}$ remained similar to that of cultures treated with PDGF alone. However, significantly increased proliferation was observed in PDGF-stimulated ECs treated with 1 μM DS-SILY$_{20}$, as compared to ECs treated with PDGF alone. Interestingly, EC proliferation was observed to decrease significantly when cells were simultaneously treated with 10 μM DS-SILY$_{20}$ and 10 ng/mL PDGF.

3.5 DS-SILY$_{20}$ encourages EC Migration

The effect of DS-SILY$_{20}$ and PDGF on EC migration across collagen-coated surfaces was examined via Oris Cell Migration Kit. Mitomycin C was utilized to growth-arrest ECs prior to treatments, thus isolating cell migration measurement with each treatment condition. A dose dependent increase in EC migration was observed with corresponding increases in DS-SILY$_{20}$ concentrations, ultimately culminating in a ~2.2-fold increase in migration for cultures treated with 10 μM DS-SILY$_{20}$ (FIG. 3C). PDGF stimulation also significantly enhanced EC migration by 40.3%. Similar to the trend observed in ECs treated with DS-SILY$_{20}$ alone, the addition of DS-SILY$_{20}$ to PDGF-stimulated cultures resulted in a dose-dependent increase in migration. Migration was increased ~3-fold in PDGF-stimulated ECs treated with 10 μM DS-SILY$_{20}$.

DS-SILY$_{20}$ Attenuates IL-6 Expression in ECs

Following exposure to DS-SILY$_{20}$ and PDGF treatments for 24 hrs, expression of IFN-γ, IL-1β, IL-6, and TNF-α from EC monolayers was examined via MSD Sector Imager. Examination of control, non-treated EC monolayers revealed that ECs exhibited 130.4±11.6 pg/mL of IL-6 (FIG. 3D). The addition of 10 ng/mL PDGF to ECs did not alter IL-6 production, as compared to no treatment controls. While no reduction in IL-6 production was observed when ECs were treated with low concentrations of DS-SILY$_{20}$, the addition of 10 μM DS-SILY$_{20}$ resulted in significantly decreased IL-6 expression, where reductions of ~50%, where observed in both PDGF-stimulated and unstimulated EC cultures. IFN-γ, IL-1β, and TNF-α produced by EC monolayers remained undetectable, likely produced at minute concentrations.

Effect of DS-SILY$_{20}$ on EC Vascular Injury Marker Expression

Figure 4:
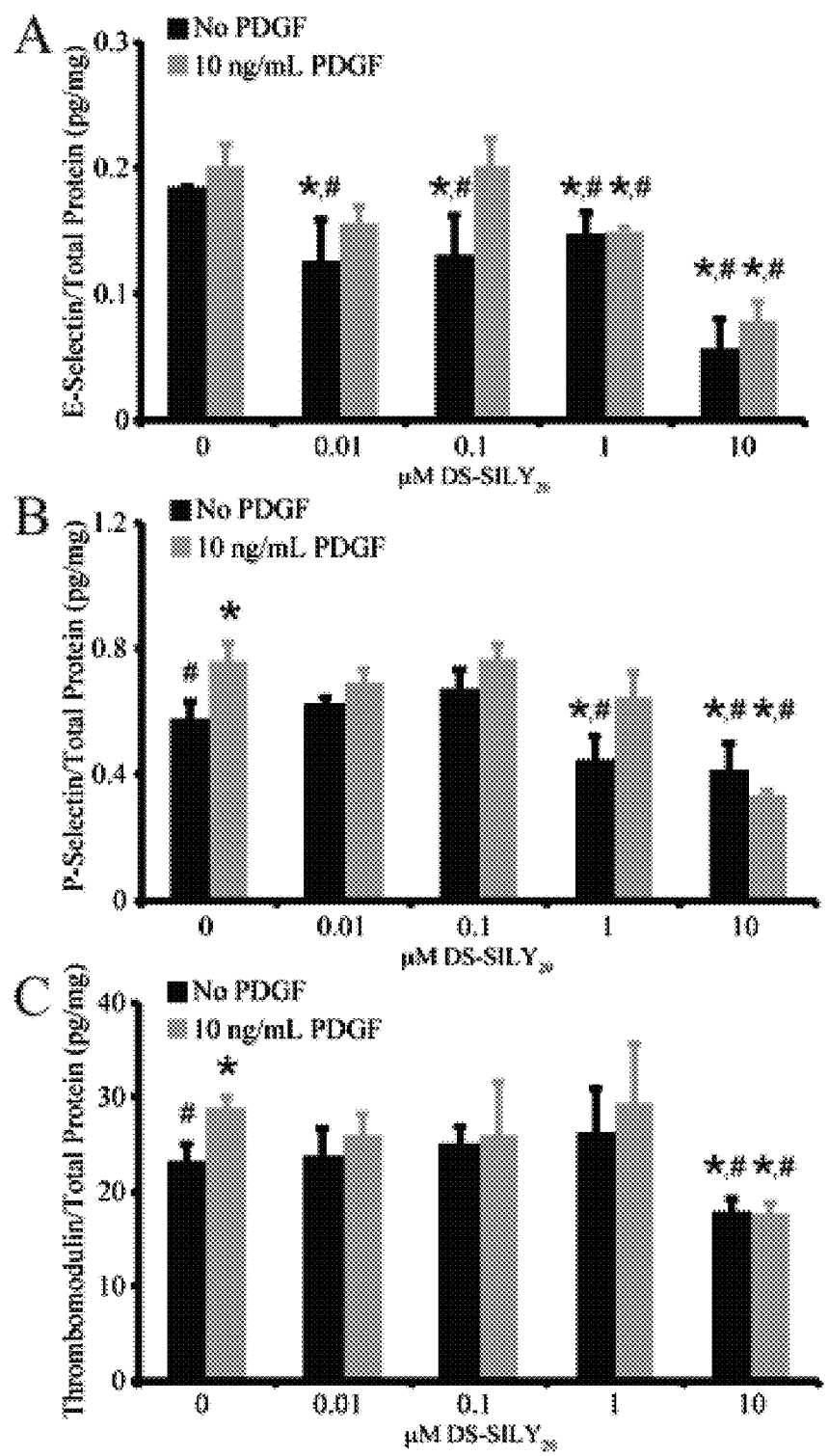
FIG. 4A-C show that the expression of E-selectin, P-selectin, and thrombomodulin in ECs is regulated by DS-SILY$_{20}$. Expression of (A) E-selectin (B) P-selectin, and (C) thrombomodulin in ECs treated with DS-SILY$_{20}$, with and without PDGF stimulation. E-selectin, P-selectin, and thrombomodulin produced by cultured ECs was measured 24 hrs post-treatment following cell lysis. * represents significance from control non-treated cells; # represents significance PDGF-treated cultures. (N>6).

To determine the effect of DS-SILY$_{20}$ and PDGF on vascular injury markers, E-selectin, P-selectin, and thrombomodulin produced by EC monolayers in vitro were analyzed via an MSD Sector Imager (FIG. 4). Control non-treated ECs monolayers exhibited 0.2 pg/mg, 0.6 pg/mg, and 23.6 pg/mg of E-selectin, P-selectin, and thrombomodulin, respectively. Production of all three vascular injury markers decreased in EC monolayers with increasing DS-SILY$_{20}$ concentrations, ultimately culminating in a 3.2, 1.4, and 1.4-fold reduction in E-selectin, P-selectin, and thrombomodulin expression, respectively. The addition of 10 ng/mL PDGF to ECs did not alter E-selectin production compared to no treatment controls. However, PDGF induced both P-selectin and thrombomodulin expression in EC monolayers. The addition of DS-SILY$_{20}$ to PDGF-stimulated EC monolayers resulted in significantly decreased E-selectin, P-selectin, and thrombomodulin production, where expression was decreased by ~60%, 56%, and 38%, respectively, following treatment with 10 μM DS-SILY$_{20}$.

Phosphorylation of ERK and p38 MAPK in ECs

Figure 5:
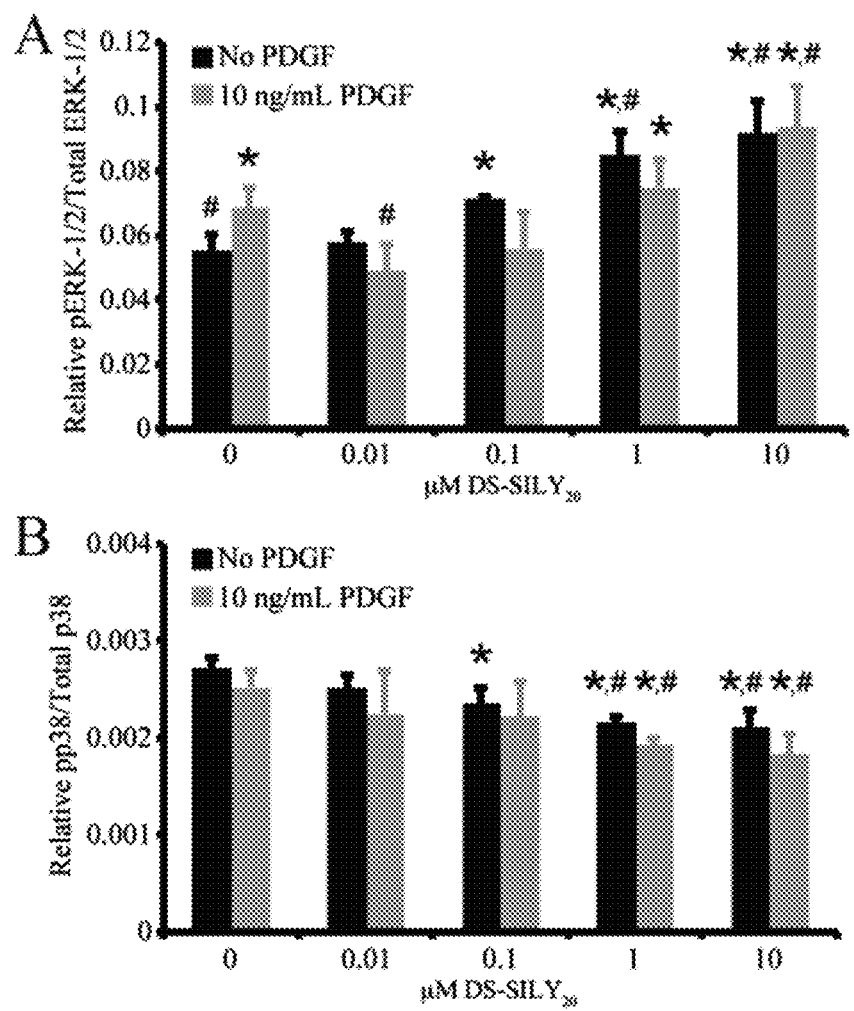
FIG. 5A-B show that DS-SILY$_{20}$ regulates ERK-1/2 and p38 phosphorylation in ECs. Relative phosphorylated (A) ERK-1/2 and (B) p38 produced in ECs treated with DS-SILY$_{20}$, with and without 10 ng/mL PDGF. The relative amount of phosphorylated ERK and p38 was normalized to total ERK and total p38 for each sample, respectively. * represents significance from control non-treated cells; # represents significance from PDGF-treated cultures. (N>3)

MAPKs, including ERK and p38, are important intracellular transduction pathways involved in vascular remodeling and disease. Phosphorylation of ERK-1/2 correlates with increased EC proliferation and migration, and p38 phosphorylation correlates with increased inflammatory cytokine expression. Thus, this example sought to correlate the changes observed in proliferation and migration (FIGS. 3B and C) or cytokine expression (FIG. 3D) with ERK-1/2 or p38 phosphorylation levels. To determine the relative amount of phosphorylated ERK-1/2 (pERK-1/2) and p38 (pp38), EC monolayers were stimulated with DS-SILY$_{20}$, with or without 10 ng/mL PDGF, for 10 mins. Cell lysates were then analyzed via MSD Sector Imager to determine the relative phosphorylation levels of the intracellular signaling molecules (FIG. 5).

After 10 mins of stimulation, a dose-dependent increase in relative pERK-1/2 levels occurred with increasing concentrations of DS-SILY$_{20}$ (FIG. 3A). ERK-1/2 phosphorylation was increased in EC monolayers stimulated with 10 ng/mL PDGF, compared to no treatment controls. Further, the addition of increased DS-SILY$_{20}$ concentrations corresponded to a dose-dependent increase in relative pERK-1/2 levels in PDGF-stimulated EC monolayers.

The addition of DS-SILY$_{20}$ resulted in a dose-dependent inhibition of relative pp38 levels in monolayer ECs, compared to no treatment controls, after 10 mins of stimulation (FIG. 5B). PDGF did not alter the phosphorylation of p38 in EC monolayers; however, the addition of DS-SILY$_{20}$ to PDGF-stimulated ECs resulted in a similar dose-dependent decrease in pp38.

Cytokine Production in EC-SMC Co-Cultures

Figure 6:
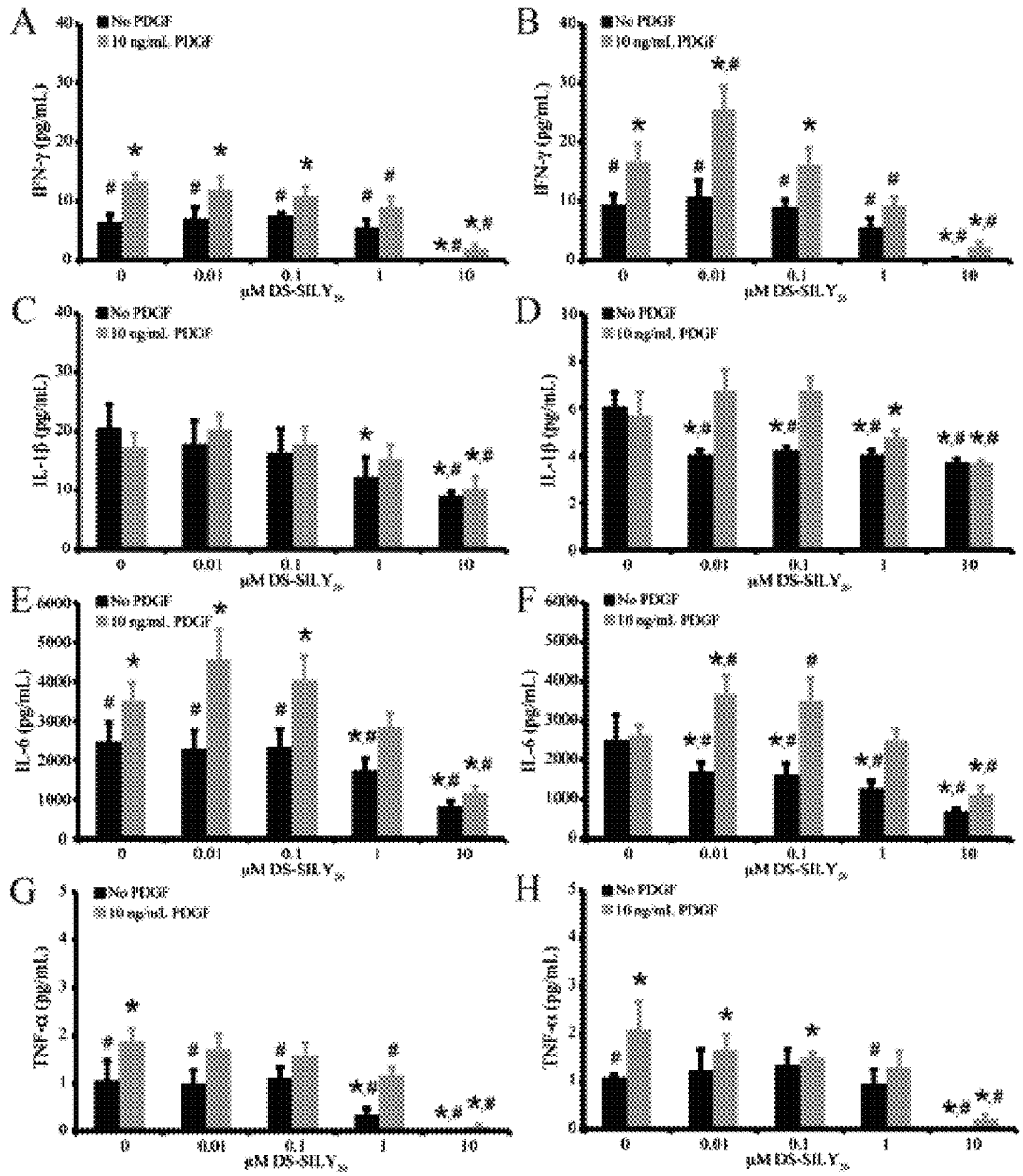
FIG. 6A-G show that DS-SILY$_{20}$ attenuates PDGF stimulated cytokine secretion in ECs. Cytokine produced (A, C, E, G) hyperplastic and (B, D, F, H) quiescent co-cultures in response to DS-SILY$_{20}$ treatment, with and without PDGF stimulation. The amount of (A, B) IFN-γ, (C, D) IL-1β, (E, F) IL-6, and (G, H) TNF-α produced by co-cultures was measured 24 hrs post-treatment. * represents significance from control non-treated cells, # represents significance from PDGF-treated cultures. (N>6).

Following DS-SILY$_{20}$ and PDGF treatments for 24 hrs, expression of IFN-γ, IL-1β, IL-6, and TNF-α from EC-SMC co-cultures was examined via MSD Sector Imager, in both the hyperplastic and quiescent co-cultures (FIG. 6). Examination of control, non-treated cultures revealed that hyperplastic co-cultures exhibited increased levels of IL-1β compared to quiescent co-cultures; however, the two cultures produced similar levels of IFN-γ, IL-6, and TNF-α (FIGS. 6C and D).

The effect of DS-SILY$_{20}$ on the production of the four pro-inflammatory cytokines was evaluated in both hyperplastic and quiescent co-cultures. For hyperplastic co-cultures, a dose-dependent decrease of pro-inflammatory cytokine production was observed as the concentration of DS-SILY$_{20}$ increased. The addition of 10 µM DS-SILY$_{20}$ decreased IL-1β and IL-6 secretion in hyperplastic co-cultures by ~55% and 66%, respectively. Further, both IFN-γ and TNF-α secretions were reduced by approximately 98% following treatment with 10 µM DS-SILY$_{20}$ in hyperplastic co-cultures. A significant reduction in IFN-γ expression was exhibited in quiescent co-cultures with 1 and 10 µM DS-SILY$_{20}$ treatment, while TNF-α expression was significantly decreased with the addition of 10 µM DS-SILY$_{20}$. Interestingly, significant decreases in IL-1β and IL-6 production were achieved at all concentrations of DS-SILY$_{20}$ tested.

The addition of 10 ng/mL PDGF significantly increased production of IFN-γ, IL-6, and TNF-α in hyperplastic co-cultures, as well as IFN-γ and TNF-α in quiescent co-cultures, compared to no treatment controls. However, a general trend was observed such that as the concentration of DS-SILY$_{20}$ increased, cytokine production in PDGF-stimulated hyperplastic co-cultures decreased. Significant reductions in IFN-γ, IL-1β, IL-6, and TNF-α expression were observed at the highest levels of DS-SILY$_{20}$ tested in hyperplastic co-cultures, compared to co-cultures treated with PDGF alone. Interestingly, quiescent co-cultures exhibited increased IFN-γ and IL-6 production following treatment with 10 ng/mL PDGF and either 0.01 or 0.1 µM DS-SILY$_{20}$. However, at high concentrations of DS-SILY$_{20}$, expression of IFN-γ and IL-6 in PDGF-stimulated quiescent co-cultures was significantly reduced compared to co-cultures stimulated with PDGF alone.

Moreover, while TNF-α and IL-1β production in PDGF-stimulated quiescent co-cultures was not altered when cultures were treated with low concentrations of DS-SILY$_{20}$, significant reductions in expression of TNF-α and IL-1β were only observed at 10 µM DS-SILY$_{20}$.

Vascular Injury Marker Expression in Co-Cultures

Figure 7:
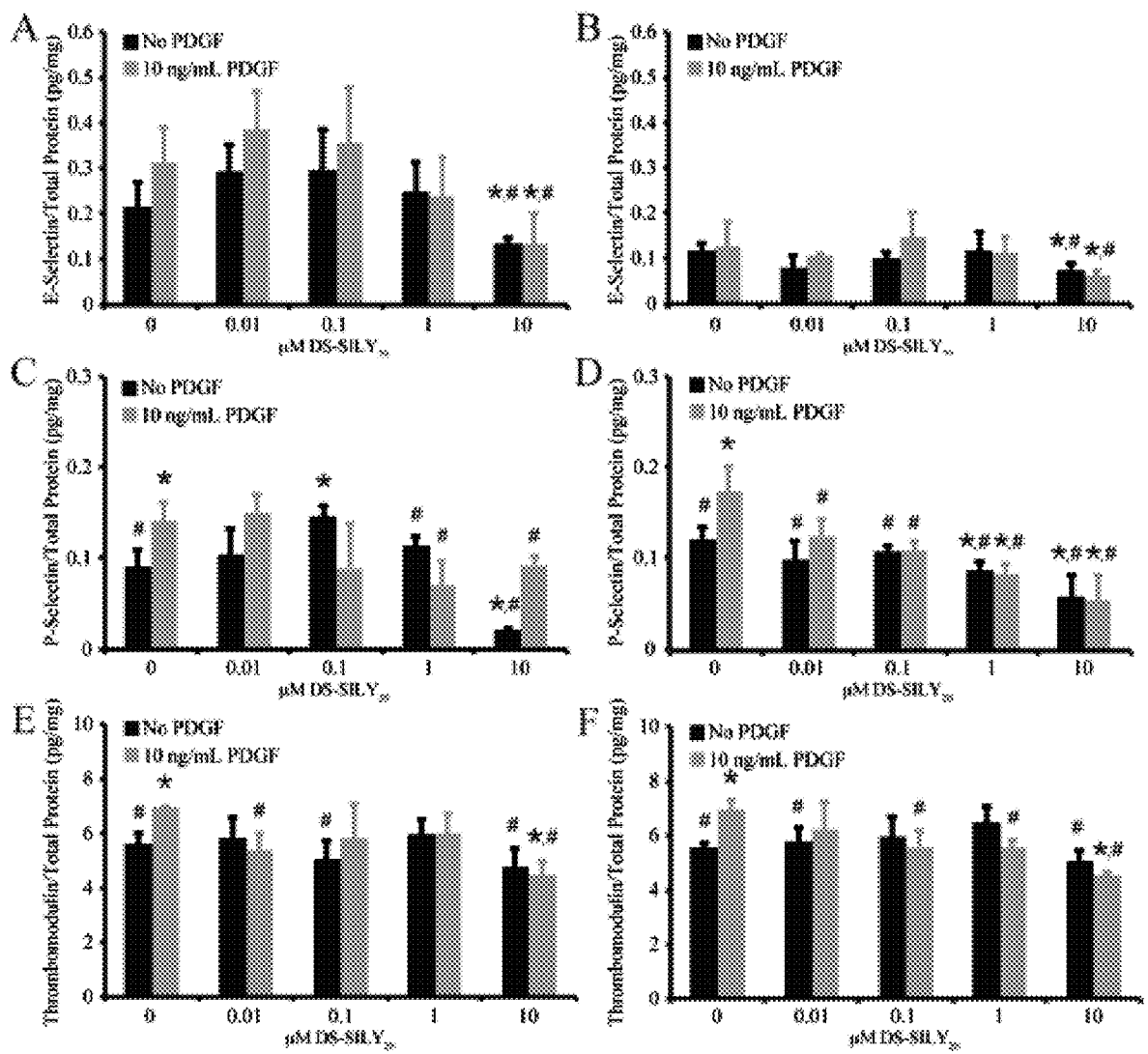
FIG. 7A-F show that DS-SILY$_{20}$ modulates E-selectin, P-selectin, and thrombomodulin expression in EC-SMC co-cultures. Expression of (A) E-selectin (B) P-selectin, and (C) thrombomodulin in (A, C, E) hyperplastic and (B, D, F) quiescent co-cultures treated with DS-SILY$_{20}$, with and without PDGF stimulation. E-selectin, P-selectin, and thrombomodulin produced by co-cultures was measured 24 hrs post-treatment following cell lysis. * represents significance from control non-treated cells; # represents significance PDGF-treated cultures. (N>6).

To determine the effect of DS-SILY$_{20}$ and PDGF on vascular injury markers, E-selectin, P-selectin, and thrombomodulin produced by EC-SMC co-cultures in vitro were analyzed via MSD Sector Imager (FIG. 7). Control non-treated hyperplastic co-cultures exhibited 0.2 pg/mg E-selectin; however, quiescent co-cultures produced significantly less E-selectin when compared to hyperplastic co-cultures (FIGS. 7A and B). Despite differences in initial levels of E-selectin production, the addition of 10 µM DS-SILY$_{20}$ to either co-culture model resulted in significantly decreased E-selectin expression, where a ~40% decrease was observed in hyperplastic and quiescent co-cultures. PDGF did not stimulate E-selectin expression in either co-culture system; however, the addition of 10 µM DS-SILY$_{20}$ to PDGF-stimulated co-cultures significantly decreased E-selectin production.

Hyperplastic and quiescent co-cultures exhibited similar amounts of P-selectin, each expressing ~0.1 pg/mg (FIGS. 7C and D). Low concentrations of DS-SILY$_{20}$ elicited increased production of P-selectin in the hyperplastic co-culture model, where a significant increase was observed with 0.1 µM DS-SILY$_{20}$ treatment. However, treatment with 10 µM DS-SILY$_{20}$ resulted in a significant reduction in P-selectin expression in hyperplastic co-cultures. Changes in P-selectin production were not observed in quiescent co-cultures treated with low concentrations of DS-SILY$_{20}$, while the addition of 1 and 10 µM DS-SILY$_{20}$ resulted in decreased P-selectin expression. The addition of PDGF significantly increased P-selectin production in both the hyperplastic and quiescent co-cultures. However, the addition of DS-SILY$_{20}$ to PDGF-stimulated co-cultures resulted in a dose dependent decrease in P-selectin production, where P-selectin was significantly decreased in hyperplastic co-cultures with both 1 and 10 µM DS-SILY$_{20}$ treatments and in quiescent co-cultures at all concentrations of DS-SILY$_{20}$ tested, as compared to co-cultures stimulated with PDGF alone.

Similar amounts of thrombomodulin were expressed in both the hyperplastic and quiescent co-cultures (FIGS. 7E and F). Thrombomodulin production was not altered with the addition of any DS-SILY$_{20}$ concentration tested in either the hyperplastic or quiescent co-culture models. However, the addition of PDGF alone significantly increased thrombomodulin production in both the hyperplastic and quiescent co-cultures. Expression of thrombomodulin was decreased in PDGF-stimulated co-cultures with 10 µM DS-SILY$_{20}$ treatment.

Endothelial denudation following PCI temporarily alters the differentiated SMC phenotype, which can trigger the restenotic cascade leading to intimal hyperplasia. The non-specific cytotoxins currently utilized as therapeutics to prevent restenosis following PCI affect not only SMCs, but also neighboring vascular ECs and inhibit formation of an intact endothelium following vessel injury. As EC proliferation and migration following PCI-induced injury is imperative for complete vessel healing, the need for new candidate therapeutics is critical. Utilizing our in vitro models, including EC monolayers, as well as both hyperplastic and quiescent EC-SMC co-cultures, we investigated the ability of DS-SILY$_{20}$ to promote EC health, even in the presence of PDGF, a growth factor known to stimulate maladaptive SMC behavior.

Figure 2:
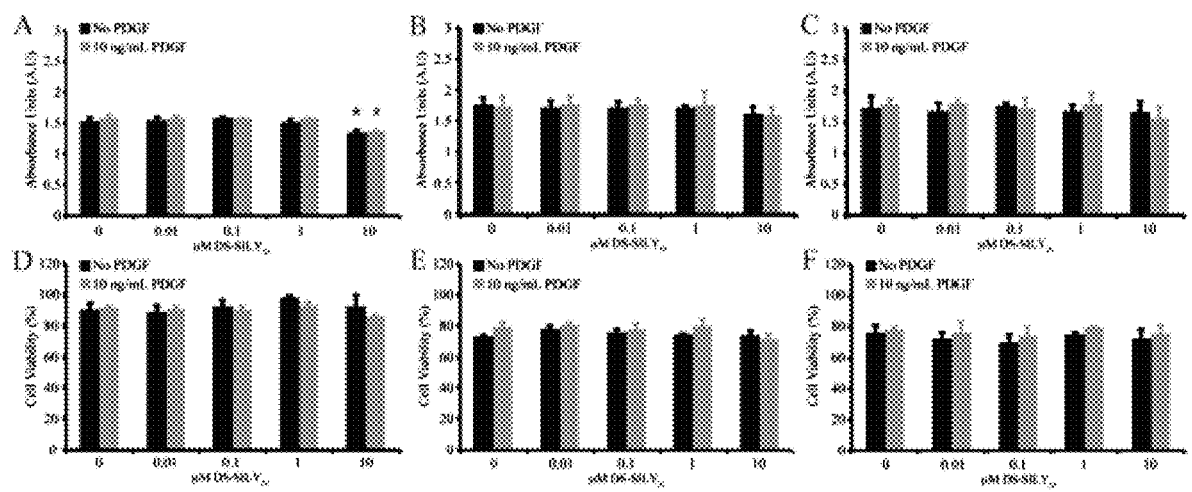
FIG. 2A-F show effect of DS-SILY$_{20}$ and PDGF on EC monolayers and EC-SMC co-cultures. (A, B, C) Metabolic activity and (D, E, F) cell viability in (A, D) EC monolayers, (B, E) hyperplastic co-cultures, and (C, F) quiescent co-cultures treated with DS-SILY$_{20}$, with or without 10 ng/mL PDGF. Cell metabolism and viability was measured 24 hrs post-treatment. * represents significance from control non-treated cells; # represents significance PDGF-treated cultures. (N>6).

This example first set out to assess potential deleterious effects of DS-SILY$_{20}$ and PDGF on the EC monolayers and co-culture systems. While metabolic activity remained constant for ECs treated with low concentrations of DS-SILY$_{20}$, with or without PDGF, decreased metabolism occurred when EC monolayers were treated with high concentrations of DS-SILY$_{20}$, regardless of PDGF treatment (FIG. 2). As no measurable changes in cell viability were observed in EC monolayers following treatment, the decrease in EC metabolism with 10 µM DS-SILY$_{20}$ did not provide any cause for concern. Interestingly, metabolic activity and cell viability were not altered in hyperplastic or quiescent co-cultures treated with any DS-SILY$_{20}$ concentration, independent of PDGF stimulation, nor were changes seen in monocultures of quiescent and proliferative SMCs as published previously. This suggests that the EC-SMC interactions may inherently protect ECs and highlight the importance of cell-cell communication in cell culture models.

In conclusion, this example demonstrates that DS-SILY$_{20}$ is able to induce proliferation and migration in ECs, while minimizing pro-inflammatory cytokine and vascular injury marker production. The in vitro models, including EC monolayers, as well as both hyperplastic and quiescent EC-SMC co-cultures, further emphasize the importance of cell-cell signaling in culture systems.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for treating a patient not undergoing or recovering from a vascular intervention procedure, and suffering from a disease associated with endothelial dysfunction at a site of inflammation, the method comprising administering to the patient an effective amount of a synthetic peptidoglycan $P_nG$ wherein n is 15 to 25 and peptide P has amino acid sequence RRANAALKAGELYKSILYGC (SEQ ID NO: 17); and wherein the glycan G is dermatan sulfate; wherein the disease associated with endothelial dysfunction is selected from the group consisting of atherosclerosis, coronary artery disease, diabetes mellitus, hypertension, hypercholesterolemia, rheumatoid arthritis, systemic lupus erythematosus, glaucoma, uremia, sepsis, and organ failure.

2. The method of claim 1, wherein the administration is intravenous, intraperitoneal, topical or through an implanted device.

3. The method of claim 1, wherein the peptide(s) are covalently bonded to the glycan via a linker.

4. The method of claim 3, wherein the linker is N-[β-maleimidopropionic acid]hydrazide (BMPH), 3-(2-pyridyldithio)propionyl hydrazide (PDPH) or the peptide GSG (SEQ ID NO: 1).

5. The method of claim 1, wherein the synthetic peptidoglycan is administered to achieve a plasma concentration of collagen binding peptide from 20 μM to 1000 μM proximate the dysfunctional endothelium.

6. The method of claim 5, wherein the synthetic peptidoglycan is administered to achieve a plasma concentration of collagen binding peptide from 100 μM to 400 μM proximate the dysfunctional endothelium.

7. A method for reducing inflammation at a vascular site in a patient, wherein the site (a) comprises permeated endothelial lining or damaged endothelial cells, and (b) is not undergoing or recovering from a vascular intervention procedure, the method comprising administering to the patient an effective amount of a synthetic peptidoglycan $P_nG$ wherein n is 15 to 25 and peptide P has amino acid sequence RRANAALKAGELYKSILYGC (SEQ ID NO: 17); and wherein the glycan G is dermatan sulfate.

* * * * *